United States Patent
Roger et al.

(10) Patent No.: US 10,155,082 B2
(45) Date of Patent: Dec. 18, 2018

(54) ENHANCED SIGNAL DETECTION FOR ACCESS DISCONNECTION SYSTEMS

(75) Inventors: Rodolfo G. Roger, Clearwater, FL (US); Thomas P. Hartranft, Clearwater, FL (US); Ramesh Wariar, Tampa, FL (US); Angel M. Lasso, Tampa, FL (US); George Lamberson, New Port Richey, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 795 days.

(21) Appl. No.: 11/676,110

(22) Filed: Feb. 16, 2007

(65) Prior Publication Data

US 2008/0065006 A1 Mar. 13, 2008

Related U.S. Application Data

(63) Continuation-in-part of application No. 10/760,849, filed on Jan. 19, 2004, now abandoned, which is a
(Continued)

(51) Int. Cl.
*A61M 37/00* (2006.01)
*A61M 1/34* (2006.01)
(Continued)

(52) U.S. Cl.
CPC ............... *A61M 1/34* (2013.01); *A61M 1/16* (2013.01); *A61M 1/3653* (2013.01);
(Continued)

(58) Field of Classification Search
CPC ............ C02F 1/44; A61M 37/00; A61M 1/34; A61M 1/3656; A61M 1/16; A61M 39/10;
(Continued)

(56) References Cited

U.S. PATENT DOCUMENTS 3,618,602 A 11/1971 Shaw
3,659,591 A 5/1972 Doll et al.
(Continued)

FOREIGN PATENT DOCUMENTS

AU 199896231 3/1999
CA 2 175 903 5/1995
(Continued)

OTHER PUBLICATIONS

Notification Concerning Transmittal of International Preliminary Report on Patentability for International Application No. PCT/US2008/051289 dated Aug. 27, 2009.
(Continued)

*Primary Examiner* — Andrew J Mensh
(74) *Attorney, Agent, or Firm* — K&L Gates LLP

(57) ABSTRACT

An access disconnection system includes an extracorporeal circuit; first and second contacts provided in the extracorporeal circuit; a current source communicating with the first contact and configured to generate a current within fluid flowing through the extracorporeal circuit; and an apparatus positioned to apply a signal at multiple points along a path from the extracorporeal circuit, the signals tending to prevent at least a portion of the current from traveling through a ground path in parallel to the extracorporeal circuit.

18 Claims, 35 Drawing Sheets

Related U.S. Application Data continuation-in-part of application No. 10/121,006, filed on Apr. 10, 2002, now Pat. No. 7,138,088.

(51) Int. Cl.

| | | |
|---|---|---|
| *A61M 1/16* | (2006.01) | |
| *A61M 1/36* | (2006.01) | |
| *G01N 27/07* | (2006.01) | |
| *G01N 27/10* | (2006.01) | |
| *A61M 5/168* | (2006.01) | |
| *A61M 39/10* | (2006.01) | |
| *G01N 33/49* | (2006.01) | |

(52) U.S. Cl.
CPC ......... *A61M 1/3656* (2014.02); *G01N 27/07* (2013.01); *G01N 27/10* (2013.01); *A61M 5/16831* (2013.01); *A61M 39/10* (2013.01); *A61M 2205/13* (2013.01); *A61M 2205/3569* (2013.01); *A61M 2205/3592* (2013.01); *A61M 2205/50* (2013.01); *G01N 33/49* (2013.01)

(58) Field of Classification Search
CPC ............ A61M 5/16831; A61M 1/3653; A61M 2205/3569; A61M 2205/13; A61M 2205/50; A61M 2205/3592; G01N 27/07; G01N 33/49
USPC ..................... 604/4.01, 5.01, 6.08
See application file for complete search history.

(56) References Cited

U.S. PATENT DOCUMENTS

| | | |
|---|---|---|
| 3,682,162 A | 8/1972 | Colyer |
| 3,682,172 A | 8/1972 | Freedman et al. |
| 3,699,960 A | 10/1972 | Freedman |
| 3,722,504 A | 3/1973 | Sawyer |
| 3,731,685 A | 5/1973 | Eidus |
| 3,744,636 A | 7/1973 | Commarmot |
| 3,759,247 A | 9/1973 | Doll et al. |
| 3,759,261 A | 9/1973 | Wang |
| 3,778,570 A | 12/1973 | Shuman |
| 3,809,078 A | 5/1974 | Mozes |
| 3,810,140 A | 5/1974 | Finley |
| 3,814,249 A | 6/1974 | Eaton |
| 3,832,067 A | 8/1974 | Kopf et al. |
| 3,832,993 A | 9/1974 | Clipp |
| 3,864,676 A | 2/1975 | Macias et al. |
| 3,867,688 A | 2/1975 | Koski |
| 3,878,095 A | 4/1975 | Frasier et al. |
| 3,882,861 A | 5/1975 | Kettering et al. |
| 3,900,396 A | 8/1975 | Lamadrid |
| 3,946,731 A | 3/1976 | Lichtenstein |
| 3,953,790 A | 4/1976 | Ebling et al. |
| 3,979,665 A | 9/1976 | Ebling et al. |
| 4,010,749 A | 3/1977 | Shaw |
| 4,017,190 A | 4/1977 | Fischel |
| 4,022,211 A | 5/1977 | Timmons et al. |
| 4,026,800 A | 5/1977 | Friedrich et al. |
| 4,055,496 A | 10/1977 | Friedrich et al. |
| 4,060,485 A | 11/1977 | Eaton |
| 4,085,047 A | 4/1978 | Thompson |
| 4,087,185 A | 5/1978 | Lamadrid |
| 4,160,946 A | 7/1979 | Frigato |
| 4,162,490 A | 7/1979 | Fu et al. |
| 4,166,961 A | 9/1979 | Dam et al. |
| 4,167,038 A | 9/1979 | Hennessy |
| 4,181,610 A | 1/1980 | Shintani et al. |
| 4,191,950 A | 3/1980 | Levin et al. |
| 4,192,311 A | 3/1980 | Felfoldi |
| 4,193,068 A | 3/1980 | Ziccardi |
| 4,194,974 A | 3/1980 | Jonsson |
| 4,231,366 A | 11/1980 | Schael |
| 4,231,370 A | 11/1980 | Mroz et al. |
| 4,294,263 A | 10/1981 | Hochman |
| 4,295,475 A | 10/1981 | Torzala |
| 4,303,887 A | 12/1981 | Hill et al. |
| 4,324,687 A | 4/1982 | Louderback et al. |
| 4,327,731 A | 5/1982 | Powell |
| 4,353,368 A | 10/1982 | Slovák et al. |
| 4,354,504 A | 10/1982 | Bro |
| 4,366,051 A | 12/1982 | Fischel |
| 4,399,823 A | 8/1983 | Donnelly |
| 4,399,824 A | 8/1983 | Davidson |
| 4,450,527 A | 5/1984 | Sramek |
| 4,469,593 A | 9/1984 | Ishihara et al. |
| 4,484,135 A | 11/1984 | Ishihara et al. |
| 4,484,573 A | 11/1984 | Yoo |
| 4,501,583 A | 2/1985 | Troutner |
| 4,534,756 A | 8/1985 | Nelson |
| 4,539,559 A | 9/1985 | Kelly et al. |
| 4,559,496 A | 12/1985 | Harnden, Jr. et al. |
| 4,566,990 A | 1/1986 | Liu et al. |
| 4,583,546 A | 4/1986 | Garde |
| 4,648,869 A | 3/1987 | Bobo, Jr. |
| 4,661,096 A | 4/1987 | Teeple |
| 4,710,163 A | 12/1987 | Butterfield |
| 4,734,198 A | 3/1988 | Harm et al. |
| 4,739,492 A | 4/1988 | Cochran |
| 4,740,755 A | 4/1988 | Ogawa |
| 4,741,343 A | 5/1988 | Bowman et al. |
| 4,791,932 A | 12/1988 | Margules |
| 4,792,328 A | 12/1988 | Beck et al. |
| 4,796,014 A | 1/1989 | Chia |
| 4,846,792 A | 7/1989 | Bobo, Jr. et al. |
| 4,862,146 A | 8/1989 | McCoy et al. |
| 4,881,413 A | 11/1989 | Georgi et al. |
| 4,898,587 A | 2/1990 | Mera |
| 4,923,613 A | 5/1990 | Chevallet |
| 4,931,051 A | 6/1990 | Castello |
| 4,936,834 A | 6/1990 | Beck et al. |
| 4,938,079 A | 7/1990 | Goldberg |
| 4,959,060 A | 9/1990 | Shimomura et al. |
| 4,965,554 A | 10/1990 | Darling |
| 4,966,729 A | 10/1990 | Carmona et al. |
| 4,976,698 A | 12/1990 | Stokley |
| 4,977,906 A | 12/1990 | DiScipio |
| 4,979,940 A | 12/1990 | Bobo, Jr. et al. |
| 4,981,467 A | 1/1991 | Bobo, Jr. et al. |
| 5,004,459 A | 4/1991 | Peabody et al. |
| 5,015,958 A | 5/1991 | Masia et al. |
| 5,024,756 A | 6/1991 | Sternby |
| 5,026,348 A | 6/1991 | Venegas |
| 5,030,487 A | 7/1991 | Rosenzweig |
| 5,030,497 A | 7/1991 | Claessen |
| 5,036,859 A | 8/1991 | Brown |
| 5,039,970 A | 8/1991 | Cox |
| 5,084,026 A | 1/1992 | Shapiro |
| 5,088,990 A | 2/1992 | Hivale et al. |
| 5,100,374 A | 3/1992 | Kageyama |
| 5,121,630 A | 6/1992 | Calvin |
| 5,137,033 A | 8/1992 | Norton |
| 5,139,482 A | 8/1992 | Simeon et al. |
| 5,145,645 A | 9/1992 | Zakin et al. |
| 5,146,414 A | 9/1992 | McKown et al. |
| 5,197,958 A | 3/1993 | Howell |
| 5,200,627 A | 4/1993 | Chevallet |
| 5,202,261 A | 4/1993 | Musho et al. |
| 5,211,201 A | 5/1993 | Kamen et al. |
| 5,247,434 A | 9/1993 | Peterson et al. |
| 5,248,934 A | 9/1993 | Roveti |
| 5,250,439 A | 10/1993 | Musho et al. |
| 5,264,830 A | 11/1993 | Kline et al. |
| 5,266,928 A | 11/1993 | Johnson |
| 5,291,181 A | 3/1994 | DePonte |
| 5,310,507 A | 5/1994 | Zakin et al. |
| 5,314,410 A | 5/1994 | Marks |
| 5,341,127 A | 8/1994 | Smith |
| 5,350,357 A | 9/1994 | Kamen |
| 5,354,289 A | 10/1994 | Mitchell et al. |
| 5,389,093 A | 2/1995 | Howell |
| 5,392,032 A | 2/1995 | Kline et al. |
| 5,395,358 A | 3/1995 | Lu |
| 5,399,295 A | 3/1995 | Gamble et al. |

(56) References Cited

U.S. PATENT DOCUMENTS

| | | |
|---|---|---|
| 5,416,027 A | 5/1995 | Baudin et al. |
| 5,431,496 A | 7/1995 | Balteau et al. |
| 5,435,010 A | 7/1995 | May |
| 5,439,442 A | 8/1995 | Bellifemine |
| 5,454,374 A | 10/1995 | Omachi |
| 5,468,236 A | 11/1995 | Everhart et al. |
| 5,469,145 A | 11/1995 | Johnson |
| 5,486,286 A | 1/1996 | Peterson et al. |
| 5,487,827 A | 1/1996 | Peterson et al. |
| 5,509,822 A | 4/1996 | Negus et al. |
| 5,510,716 A | 4/1996 | Buffaloe, IV et al. |
| 5,510,717 A | 4/1996 | Buffaloe, IV et al. |
| 5,522,809 A | 6/1996 | Larsonneur |
| 5,533,412 A | 7/1996 | Jerman et al. |
| 5,542,932 A | 8/1996 | Daugherty |
| 5,557,263 A | 9/1996 | Fisher et al. |
| 5,567,320 A | 10/1996 | Goux et al. |
| 5,568,128 A | 10/1996 | Nair |
| 5,570,026 A | 10/1996 | Buffaloe, IV et al. |
| 5,570,082 A | 10/1996 | Mahgereffeh et al. |
| 5,571,401 A | 11/1996 | Lewis et al. |
| 5,579,765 A | 12/1996 | Cox et al. |
| 5,603,902 A | 2/1997 | Maltais et al. |
| 5,644,240 A | 7/1997 | Brugger |
| 5,645,734 A | 7/1997 | Kenley et al. |
| 5,649,914 A | 7/1997 | Glaug et al. |
| 5,675,000 A | 8/1997 | Ellingboe |
| 5,670,050 A | 9/1997 | Brose et al. |
| 5,674,390 A | 10/1997 | Matthews et al. |
| 5,674,404 A | 10/1997 | Kenley et al. |
| 5,674,752 A | 10/1997 | Buckley et al. |
| 5,681,298 A | 10/1997 | Brunner et al. |
| 5,685,989 A | 11/1997 | Krivitski et al. |
| 5,690,610 A | 11/1997 | Ito et al. |
| 5,690,624 A | 11/1997 | Sasaki et al. |
| 5,690,821 A | 11/1997 | Kenley et al. |
| 5,698,089 A | 12/1997 | Lewis et al. |
| 5,702,376 A | 12/1997 | Glaug et al. |
| 5,702,377 A | 12/1997 | Collier, IV et al. |
| 5,718,692 A | 2/1998 | Schon et al. |
| 5,730,418 A | 3/1998 | Feith et al. |
| 5,744,027 A | 4/1998 | Connell et al. |
| 5,760,694 A | 6/1998 | Nissim et al. |
| 5,762,805 A | 6/1998 | Truitt et al. |
| 5,766,212 A | 6/1998 | Jitoe et al. |
| 5,779,657 A | 7/1998 | Daneshvar |
| 5,788,833 A | 8/1998 | Lewis et al. |
| 5,790,035 A | 8/1998 | Ho |
| 5,790,036 A | 8/1998 | Fisher et al. |
| 5,796,345 A | 8/1998 | Leventis et al. |
| 5,797,892 A | 8/1998 | Glaug et al. |
| 5,800,386 A | 9/1998 | Bellifemine |
| 5,802,814 A | 9/1998 | Sano |
| 5,803,915 A | 9/1998 | Kremenchugsky et al. |
| 5,813,432 A | 9/1998 | Elsdon et al. |
| 5,817,076 A | 10/1998 | Ford |
| 5,838,240 A | 11/1998 | Johnson |
| 5,842,998 A | 12/1998 | Gopakumaran et al. |
| 5,845,644 A | 12/1998 | Hughes et al. |
| 5,847,639 A | 12/1998 | Yaniger |
| 5,862,804 A | 1/1999 | Ketchum |
| 5,863,421 A * | 1/1999 | Peter et al. .................. 210/134 |
| 5,868,723 A | 2/1999 | Al-Sabah |
| 5,885,264 A | 3/1999 | Matsushita |
| 5,891,398 A | 4/1999 | Lewis et al. |
| 5,900,726 A | 5/1999 | Brugger et al. |
| 5,900,817 A | 5/1999 | Olmassakian |
| 5,903,222 A | 5/1999 | Kawarizadeh et al. |
| 5,904,671 A | 5/1999 | Navot et al. |
| 5,908,411 A | 6/1999 | Matsunari |
| 5,910,252 A | 6/1999 | Truitt et al. |
| 5,911,706 A | 6/1999 | Estabrook et al. |
| 5,911,872 A | 6/1999 | Lewis et al. |
| 5,931,801 A | 8/1999 | Burbank et al. |
| 5,931,802 A | 8/1999 | Yoshida et al. |
| 5,932,110 A | 8/1999 | Shah et al. |
| 5,938,038 A | 8/1999 | Ziberna |
| 5,938,938 A | 8/1999 | Bosetto et al. |
| 5,941,248 A | 8/1999 | Wheeler |
| 5,947,943 A | 9/1999 | Lee |
| 5,954,691 A | 9/1999 | Prosl |
| 5,954,951 A | 9/1999 | Nuccio |
| 5,959,535 A | 9/1999 | Remsburg |
| 6,009,339 A | 12/1999 | Bentsen et al. |
| 6,015,386 A | 1/2000 | Kenley et al. |
| 6,015,387 A | 1/2000 | Schwartz et al. |
| 6,038,914 A | 3/2000 | Carr et al. |
| 6,044,691 A | 4/2000 | Kenley et al. |
| 6,063,042 A | 5/2000 | Navot et al. |
| 6,066,261 A | 5/2000 | Spickermann et al. |
| 6,075,178 A | 6/2000 | La Wilhelm et al. |
| 6,075,367 A | 6/2000 | Brugger |
| 6,077,443 A | 6/2000 | Goldau |
| 6,090,048 A | 7/2000 | Hertz et al. |
| 6,093,869 A | 7/2000 | Roe et al. |
| 6,097,297 A | 8/2000 | Ford |
| 6,113,577 A | 9/2000 | Hakky |
| 6,117,099 A | 9/2000 | Steuer et al. |
| 6,123,847 A | 9/2000 | Bene |
| 6,136,201 A | 10/2000 | Shah et al. |
| 6,139,748 A | 10/2000 | Ericson et al. |
| 6,143,181 A | 11/2000 | Falkvall et al. |
| 6,149,636 A | 11/2000 | Roe et al. |
| 6,153,109 A | 11/2000 | Krivitski |
| 6,160,198 A | 12/2000 | Roe et al. |
| 6,166,639 A | 12/2000 | Pierce et al. |
| 6,167,765 B1 | 1/2001 | Weitzel |
| 6,169,225 B1 | 1/2001 | Otsubo |
| 6,171,289 B1 | 1/2001 | Millot et al. |
| 6,183,437 B1 | 2/2001 | Walker |
| 6,187,199 B1 | 2/2001 | Goldau |
| 6,189,388 B1 | 2/2001 | Cole et al. |
| 6,200,250 B1 | 3/2001 | Janszen |
| 6,206,851 B1 | 3/2001 | Prosl |
| 6,208,880 B1 | 3/2001 | Bentsen et al. |
| 6,210,591 B1 | 4/2001 | Kriritski |
| 6,217,539 B1 | 4/2001 | Rainer |
| 6,221,040 B1 | 4/2001 | Kleinekofort |
| 6,255,396 B1 | 7/2001 | Ding et al. |
| 6,284,131 B1 | 9/2001 | Hogard et al. |
| 6,309,673 B1 | 10/2001 | Duponchelle et al. |
| 6,319,243 B1 | 11/2001 | Becker et al. |
| 6,325,774 B1 | 12/2001 | Bene et al. |
| 6,331,244 B1 | 12/2001 | Lewis et al. |
| 6,372,848 B1 | 4/2002 | Yang et al. |
| 6,386,050 B1 | 5/2002 | Yin et al. |
| 6,387,329 B1 | 5/2002 | Lewis et al. |
| 6,397,661 B1 | 6/2002 | Grimes et al. |
| 6,402,207 B1 | 6/2002 | Segal et al. |
| 6,406,460 B1 | 6/2002 | Hogan |
| 6,431,175 B1 * | 8/2002 | Penner .................. A61N 5/1048 128/899 |
| 6,445,304 B1 | 9/2002 | Bandeian et al. |
| 6,452,371 B1 | 9/2002 | Brugger |
| 6,461,329 B1 | 10/2002 | Van Antwerp et al. |
| 6,500,154 B1 | 12/2002 | Hakky et al. |
| 6,514,225 B1 | 2/2003 | Utterberg et al. |
| 6,565,525 B1 | 5/2003 | Burbank et al. |
| 6,572,576 B2 | 6/2003 | Brugger et al. |
| 6,575,927 B1 | 6/2003 | Weitzel et al. |
| 6,582,397 B2 | 6/2003 | Alesi et al. |
| 6,585,675 B1 | 7/2003 | O'Mahony et al. |
| 6,595,942 B2 | 7/2003 | Kleinekofort |
| 6,595,943 B1 | 7/2003 | Burbank |
| 6,595,944 B2 | 7/2003 | Balschat et al. |
| 6,607,697 B1 | 8/2003 | Muller |
| 6,610,367 B2 | 8/2003 | Lewis et al. |
| 6,612,624 B1 | 9/2003 | Segal et al. |
| 6,614,212 B2 | 9/2003 | Brugger et al. |
| 6,623,443 B1 | 9/2003 | Polaschegg |
| 6,623,638 B2 | 9/2003 | Watkins |
| 6,663,585 B1 * | 12/2003 | Ender .................. 604/6.08 |
| 6,664,104 B2 | 12/2003 | Pourahmadi et al. |
| 6,683,679 B2 | 1/2004 | Belenkii |

(56) References Cited

U.S. PATENT DOCUMENTS

| | | |
|---|---|---|
| 6,691,040 B2 | 2/2004 | Bosetto et al. |
| 6,730,233 B2 | 5/2004 | Pedrazzi |
| 6,736,789 B1 | 5/2004 | Spickermann |
| 6,736,811 B2 | 5/2004 | Panescu et al. |
| 6,749,567 B2 | 6/2004 | Davis et al. |
| 6,752,785 B2 | 6/2004 | Van Antwerp et al. |
| 6,758,975 B2 | 7/2004 | Peabody et al. |
| 6,759,010 B2 | 7/2004 | Lewis et al. |
| 6,767,333 B1 | 7/2004 | Muller et al. |
| 6,779,396 B2 | 7/2004 | Muller et al. |
| 6,794,981 B2 | 9/2004 | Padmanabhan et al. |
| 6,804,991 B2 | 10/2004 | Balschat et al. |
| 6,806,947 B1 | 10/2004 | Ekdahl et al. |
| 6,827,698 B1 | 12/2004 | Kleinekofort |
| 6,880,404 B2 | 4/2005 | Uberreiter |
| 6,890,315 B1 | 5/2005 | Levin et al. |
| 6,893,879 B2 | 5/2005 | Petersen et al. |
| 6,912,917 B2 | 7/2005 | Brugger et al. |
| 6,924,733 B1 | 8/2005 | McTier et al. |
| 6,932,786 B2 * | 8/2005 | Giacomelli et al. .......... 604/6.08 |
| 6,979,306 B2 | 12/2005 | Moll |
| 7,011,855 B2 | 3/2006 | Martis et al. |
| 7,022,098 B2 | 4/2006 | Wariar et al. |
| 7,040,142 B2 | 5/2006 | Burbank |
| 7,052,480 B2 | 5/2006 | Han et al. |
| 7,053,059 B2 | 5/2006 | Zieske |
| 7,053,781 B1 | 5/2006 | Haire et al. |
| 7,056,316 B1 | 6/2006 | Burbank et al. |
| 7,060,047 B2 * | 6/2006 | Lodi et al. ................... 604/6.08 |
| 7,070,591 B2 | 7/2006 | Adams et al. |
| 7,077,819 B1 | 7/2006 | Goldau et al. |
| 7,087,033 B2 | 8/2006 | Brugger et al. |
| 7,115,107 B2 | 10/2006 | Delnevo et al. |
| 7,138,088 B2 | 11/2006 | Warier et al. |
| 7,147,615 B2 | 12/2006 | Warier et al. |
| 7,172,569 B2 | 2/2007 | Kleinekofort |
| 7,172,570 B2 | 2/2007 | Cavalcanti et al. |
| 7,176,344 B2 | 2/2007 | Gustafson et al. |
| 7,217,251 B2 | 5/2007 | Olsen et al. |
| 7,230,687 B2 | 6/2007 | O'Mahony et al. |
| 7,276,041 B2 | 10/2007 | Moll |
| 7,278,991 B2 | 10/2007 | Morris et al. |
| 7,291,123 B2 | 10/2007 | Baraldi et al. |
| 7,537,687 B2 * | 5/2009 | Toyoda et al. ................. 210/85 |
| 2001/0004523 A1 | 6/2001 | Bosetto et al. |
| 2002/0036375 A1 | 3/2002 | Matsuda |
| 2002/0042125 A1 | 4/2002 | Petersen et al. |
| 2002/0055167 A1 | 5/2002 | Pourahmadi et al. |
| 2002/0088752 A1 | 7/2002 | Balschat et al. |
| 2002/0120260 A1 | 8/2002 | Morris et al. |
| 2002/0120261 A1 | 8/2002 | Morris et al. |
| 2002/0121471 A1 | 9/2002 | Pedrazzi |
| 2002/0141901 A1 | 10/2002 | Lewis et al. |
| 2002/0162778 A1 | 11/2002 | Peabody et al. |
| 2002/0173731 A1 | 11/2002 | Martin et al. |
| 2002/0188206 A1 | 12/2002 | Davis et al. |
| 2002/0190839 A1 | 12/2002 | Padmanabhan et al. |
| 2002/0197390 A1 | 12/2002 | Lewis et al. |
| 2002/0198483 A1 | 12/2002 | Wariar et al. |
| 2003/0009123 A1 | 1/2003 | Brugger et al. |
| 2003/0016002 A1 | 1/2003 | Brugger et al. |
| 2003/0036719 A1 | 2/2003 | Giacomelli et al. |
| 2003/0075498 A1 | 4/2003 | Watkins et al. |
| 2003/0083901 A1 | 5/2003 | Bosch et al. |
| 2003/0093069 A1 | 5/2003 | Panescu et al. |
| 2003/0094369 A1 | 5/2003 | Tolley et al. |
| 2003/0126910 A1 | 7/2003 | Burbank |
| 2003/0128125 A1 | 7/2003 | Burbank et al. |
| 2003/0128126 A1 | 7/2003 | Burbank et al. |
| 2003/0138501 A1 | 7/2003 | Elisabettini et al. |
| 2003/0152482 A1 | 8/2003 | O'Mahony et al. |
| 2003/0176829 A1 | 9/2003 | Lodi et al. |
| 2003/0194894 A1 | 10/2003 | Wariar et al. |
| 2003/0195453 A1 | 10/2003 | Han et al. |
| 2003/0195454 A1 | 10/2003 | Wariar et al. |
| 2004/0054352 A1 | 3/2004 | Adams et al. |
| 2004/0113801 A1 | 6/2004 | Gustafson et al. |
| 2004/0171977 A1 | 9/2004 | Paolini et al. |
| 2004/0185709 A1 | 9/2004 | Williams, Jr. et al. |
| 2004/0186409 A1 | 9/2004 | Cavalcanti et al. |
| 2004/0186415 A1 | 9/2004 | Burbank et al. |
| 2004/0201216 A1 | 10/2004 | Segal et al. |
| 2004/0243046 A1 | 12/2004 | Brugger et al. |
| 2004/0254513 A1 | 12/2004 | Shang et al. |
| 2005/0010118 A1 | 1/2005 | Toyoda et al. |
| 2005/0010157 A1 | 1/2005 | Baraldi et al. |
| 2005/0038325 A1 | 2/2005 | Moll |
| 2005/0096578 A1 | 5/2005 | Kleinekofort |
| 2005/0131332 A1 | 6/2005 | Kelly et al. |
| 2005/0230313 A1 | 10/2005 | O'Mahony et al. |
| 2005/0241387 A1 | 11/2005 | Miesel et al. |
| 2005/0242034 A1 | 11/2005 | Connell et al. |
| 2005/0245858 A1 | 11/2005 | Miesel et al. |
| 2005/0245887 A1 | 11/2005 | Olsen et al. |
| 2005/0256451 A1 | 11/2005 | Adams et al. |
| 2005/0256457 A1 | 11/2005 | Rome |
| 2006/0012774 A1 | 1/2006 | O'Mahony et al. |
| 2006/0064159 A1 | 3/2006 | Porter et al. |
| 2006/0069339 A1 | 3/2006 | Moll |
| 2006/0081517 A1 | 4/2006 | Toyoda et al. |
| 2006/0087120 A1 | 4/2006 | Segal et al. |
| 2006/0116623 A1 | 6/2006 | Han et al. |
| 2006/0130591 A1 | 6/2006 | Perkins |
| 2006/0166548 A1 | 7/2006 | Williams et al. |
| 2006/0184087 A1 | 8/2006 | Wariar et al. |
| 2007/0000847 A1 | 1/2007 | Ross et al. |
| 2007/0004996 A1 | 1/2007 | Lovejoy et al. |
| 2007/0010779 A1 | 1/2007 | Utterberg et al. |
| 2007/0066928 A1 | 3/2007 | Lannoy |
| 2008/0065006 A1 | 3/2008 | Roger |
| 2008/0195021 A1 | 8/2008 | Roger |
| 2008/0195060 A1 | 8/2008 | Roger |
| 2009/0079578 A1 | 3/2009 | Dvorsky |
| 2009/0080757 A1 | 3/2009 | Roger |
| 2009/0082646 A1 | 3/2009 | Bouton |
| 2009/0082647 A1 | 3/2009 | Busby |
| 2009/0082649 A1 | 3/2009 | Muller |
| 2009/0082653 A1 | 3/2009 | Rohde |
| 2009/0082676 A1 | 3/2009 | Bennison |
| 2009/0088612 A1 | 4/2009 | Bouton |
| 2009/0088613 A1 | 4/2009 | Marttila |
| 2009/0088683 A1 | 4/2009 | Roger |
| 2009/0105627 A1 | 4/2009 | Rohde |
| 2010/0022934 A1 | 1/2010 | Hogard |
| 2010/0022935 A1 | 1/2010 | Muller |

FOREIGN PATENT DOCUMENTS

| | | |
|---|---|---|
| CA | 2312746 | * 11/1998 |
| CA | 2519423 | 9/2004 |
| CA | 2535502 | 3/2005 |
| CA | 2 282 628 | 11/2006 |
| DE | 28 38 414 | 3/1980 |
| DE | 29 48 768 | 6/1981 |
| DE | 30 45 514 | 7/1982 |
| DE | 32 23 086 | 7/1983 |
| DE | 34 40 584 | 5/1986 |
| DE | 3639797 | 2/1988 |
| DE | 38 23 859 | 1/1990 |
| DE | 38 36 712 | 5/1990 |
| DE | 3909548 | 9/1990 |
| DE | 40 00 961 | 7/1991 |
| DE | 40 14 572 | 11/1991 |
| DE | 40 18 953 | 1/1992 |
| DE | 40 23 336 | 2/1992 |
| DE | 42 39 937 | 6/1994 |
| DE | 4239937 | 8/1995 |
| DE | 19739099 | 1/1998 |
| DE | 19 74 6367 | 6/1998 |
| DE | 19 72 8031 | 1/1999 |
| DE | 19823836 | 12/1999 |
| DE | 19 90 1078 | 2/2000 |
| DE | 10 10 0146 | 7/2002 |
| EP | 0032906 | 8/1981 |

(56) References Cited

FOREIGN PATENT DOCUMENTS

| | | |
|---|---|---|
| EP | 0089875 | 9/1983 |
| EP | 0 270 048 | 6/1988 |
| EP | 0 272 414 | 6/1988 |
| EP | 0 287 485 | 10/1988 |
| EP | 0 328 162 | 8/1989 |
| EP | 0 328 163 | 8/1989 |
| EP | 0 332 330 | 9/1989 |
| EP | 0 259 551 | 9/1990 |
| EP | 0 542 140 | 5/1993 |
| EP | 0 551 043 | 7/1993 |
| EP | 0 472 798 | 3/1994 |
| EP | 0 584 557 | 3/1994 |
| EP | 0 590 810 | 4/1994 |
| EP | 0 611 228 | 8/1994 |
| EP | 688531 | 12/1995 |
| EP | 0705611 | 4/1996 |
| EP | 551043 | 7/1996 |
| EP | 0 745 400 | 12/1996 |
| EP | 0 820 776 | 1/1998 |
| EP | 0 835 669 | 4/1998 |
| EP | 0 846 470 | 6/1998 |
| EP | 845273 | 6/1998 |
| EP | 590810 | 7/1998 |
| EP | 0 895 787 | 2/1999 |
| EP | 0 898 975 | 3/1999 |
| EP | 0 898 976 | 3/1999 |
| EP | 0 911 044 | 4/1999 |
| EP | 0 930 080 | 7/1999 |
| EP | 0 943 369 | 9/1999 |
| EP | 0980513 | 2/2000 |
| EP | 1019118 | 7/2000 |
| EP | 1156841 | 11/2001 |
| EP | 1395314 | 3/2004 |
| EP | 1 401 518 | 3/2006 |
| EP | 1706731 | 10/2006 |
| EP | 10075427 | 12/2010 |
| FR | 2 680 678 | 5/1993 |
| FR | 2 737 124 | 1/1997 |
| GB | 2 069 702 | 8/1981 |
| GB | 2069702 | 8/1981 |
| GB | 2 145 859 | 3/1985 |
| GB | 2145859 | 4/1985 |
| GB | 2 177 247 | 1/1987 |
| GB | 2177247 | 1/1987 |
| GB | 2 250 121 | 5/1992 |
| GB | 2250121 | 5/1992 |
| JP | 55-031407 | 3/1980 |
| JP | 56-080257 | 7/1981 |
| JP | 57-044845 | 3/1982 |
| JP | 62-042047 | 2/1987 |
| JP | 62-54157 | 3/1987 |
| JP | 64-052473 | 2/1989 |
| JP | 01250733 | 10/1989 |
| JP | 4008361 | 1/1992 |
| JP | 5237184 | 9/1993 |
| JP | 6178789 | 6/1994 |
| JP | 8098881 | 4/1996 |
| JP | 9-28791 | 2/1997 |
| JP | 10-201842 | 4/1998 |
| JP | 10211278 | 8/1998 |
| JP | 11-104233 | 4/1999 |
| JP | 11-267197 | 10/1999 |
| JP | 11290452 | 10/1999 |
| JP | 11299889 | 11/1999 |
| JP | 2000-140092 | 5/2000 |
| JP | 2000131286 | 5/2000 |
| JP | 2001-208710 | 8/2001 |
| JP | 2001-515766 | 9/2001 |
| JP | 2003-518413 | 6/2003 |
| JP | 2004-521707 | 7/2004 |
| JP | 2004-521708 | 7/2004 |
| JP | 2006-507024 | 3/2006 |
| JP | 2006055588 | 3/2006 |
| JP | 2006-110120 | 4/2006 |
| JP | 2006-511244 | 4/2006 |
| JP | 2006-512101 | 4/2006 |
| JP | 2006110118 | 4/2006 |
| JP | 2007-000621 | 1/2007 |
| JP | 2007-020801 | 2/2007 |
| NZ | 337335 | 5/2001 |
| TW | 249204 | 6/1995 |
| WO | WO 81/00295 | 2/1981 |
| WO | WO 86/04710 | 8/1986 |
| WO | 89/12228 | 12/1989 |
| WO | WO 89/12228 | 12/1989 |
| WO | WO 94/02918 | 2/1994 |
| WO | WO 94/07224 | 3/1994 |
| WO | WO 95/12545 | 5/1995 |
| WO | WO 96/25904 | 8/1996 |
| WO | WO 9702057 | 1/1997 |
| WO | WO 97/03712 | 2/1997 |
| WO | WO 97/10013 | 3/1997 |
| WO | WO 98/32476 | 7/1998 |
| WO | WO 98/38485 | 9/1998 |
| WO | WO 99/12588 | 3/1999 |
| WO | WO 99/24145 | 5/1999 |
| WO | WO 99/26686 | 6/1999 |
| WO | WO 99/29356 | 6/1999 |
| WO | WO 99/42151 | 8/1999 |
| WO | WO 00/38761 | 7/2000 |
| WO | WO 01/06975 | 2/2001 |
| WO | WO 01/24854 | 4/2001 |
| WO | 01/47581 | 7/2001 |
| WO | WO 01/47581 | 7/2001 |
| WO | WO 02/098543 | 12/2002 |
| WO | 03/002174 | 1/2003 |
| WO | WO 03/000315 | 1/2003 |
| WO | WO 03/006944 | 1/2003 |
| WO | WO 03/086504 | 10/2003 |
| WO | WO 03/086505 | 10/2003 |
| WO | WO 03/086506 | 10/2003 |
| WO | WO 2004/082740 | 9/2004 |
| WO | WO 2004/084972 | 10/2004 |
| WO | WO 2004/108192 | 12/2004 |
| WO | WO 2004/108206 | 12/2004 |
| WO | 05/019416 | 3/2005 |
| WO | WO 2005/019416 | 3/2005 |
| WO | 05/046439 | 5/2005 |
| WO | WO 2005/046439 | 5/2005 |
| WO | WO 2005/105199 | 11/2005 |
| WO | WO 2005/105200 | 11/2005 |
| WO | WO 2006/001759 | 1/2006 |
| WO | 06/044677 | 9/2006 |
| WO | 06/138359 | 12/2006 |
| WO | 2008/100675 A1 | 9/2008 |

OTHER PUBLICATIONS

Office Action for Japanese Application No. 2010-55110 dated Apr. 26, 2013.
Office Action for Mexican Patent Application PA/a/2006/008140 dated May 21, 2012.
Extended European Search Report for European Application No. 10075482.9 dated Feb. 2, 2011.
Japanese Office Action for Application No. 2009-206484 dated Mar. 1, 2012.
Notification concerning transmittal of International Preliminary Report on Patentability for International Application No. PCT/US2008/051289 dated Aug. 19, 2009.
Office Action for Mexican Patent Application PA/a/2009/008502 dated Jun. 6, 2012.
Office Action for European Patent Application No. 03723889.6 dated May 23, 2012.
Office Action for European Divisional Patent Application No. 10075427.4 dated May 30, 2012.
Search Report for Divisional European Application No. 10075380.05 dated Jul. 16, 2012.
Office Action for European Patent Application No. 10075482.9 dated Jul. 27, 2012.
Office Action for European Patent Application No. 08727811.5 dated Jul. 18, 2012.

(56) References Cited

OTHER PUBLICATIONS

Office Action for Japanese Application No. 2009-206484 dated Aug. 22, 2012.
European Office Action dated Jun. 18, 2013 for Application No. 03 723 889.6-1662.
Office Action for Japanese Application No. 2009-549652 dated Sep. 14, 2012.
Japanese Office Action dated Nov. 21, 2013 for Application No. 2012-272276.
Japanese Office Action dated Dec. 2, 2013 for Application No. 2013-007007.
European Office Action dated Dec. 20, 2013 for Application No. 03 723 889.6-1662.
European Office Action for Application No. 10 075 427.4-2320 dated Jan. 25, 2013.
Office Action for Japanese Patent Application No. 2010-055110 dated May 30, 2012.
Publication for Opposition No. 4-22586 (Partially corresponding to U.S. Pat. No. 4469593).
Utility Model Publication for Opposition No. 63-9287.
Office Action for Japanese Application No. 2010-055110 dated Oct. 25, 2012.
Mexican Office Action dated Oct. 22, 2013 for Application No. MX/a/2011/012455.
European Office Action for App. No. 10 075 482.9-1662 dated Feb. 27, 2013.
European Search Report for Application No. 12170615.4-2320 dated Oct. 30, 2012.
Japanese Office Action dated Mar. 10, 2014 for Application No. 2013-007077.
Canadian Office Action dated Mar. 4, 2014 for Application No. 2,673,877.
European Office Action dated Mar. 21, 2014 for Application No. 10 075 380.5-1662.
European Office Action dated Oct. 17, 2014 for Application No. 10 075 380.5-1662.
Japanese Office Action dated Sep. 11, 2014 for Application No. 2013-034343.
European Communication dated Mar. 20, 2015 for Application No. 08 727 811.5-1654.
European Communication dated Sep. 19, 2016 for Application No. 16159018.7.
European Communication dated Feb. 27, 2017 for Application No. 12 170 620.4-1664.
European Communication dated Oct. 13, 2017 for Application No. 16 159 018.7-1651.

* cited by examiner

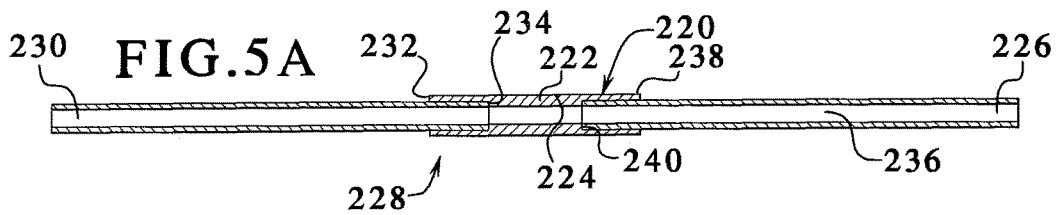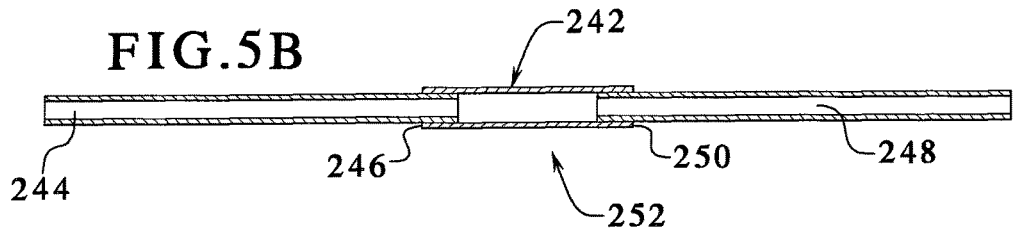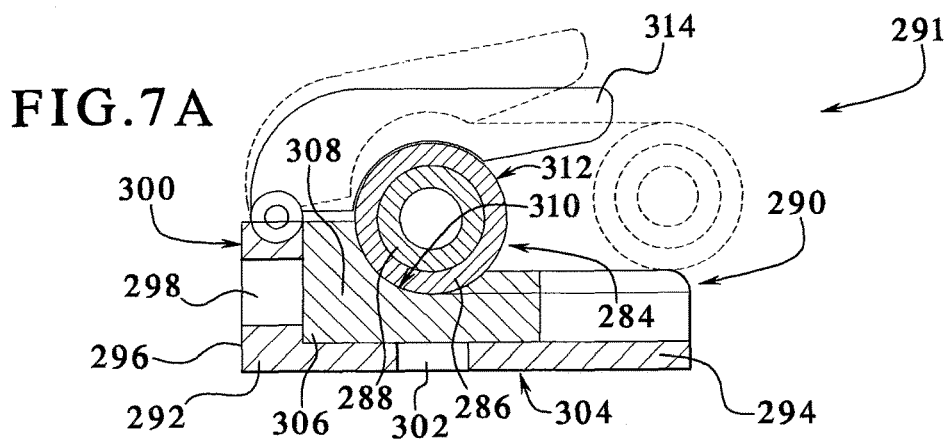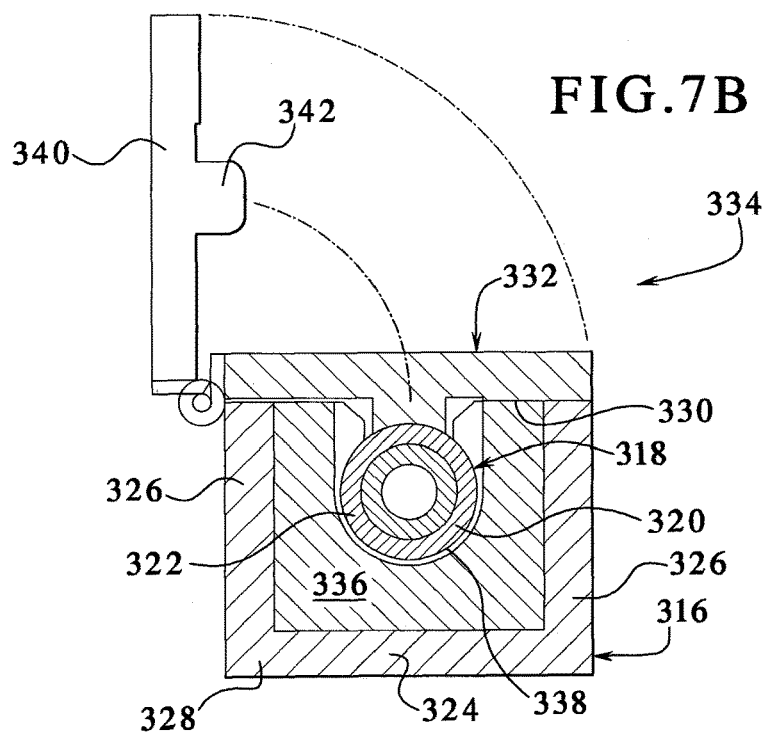

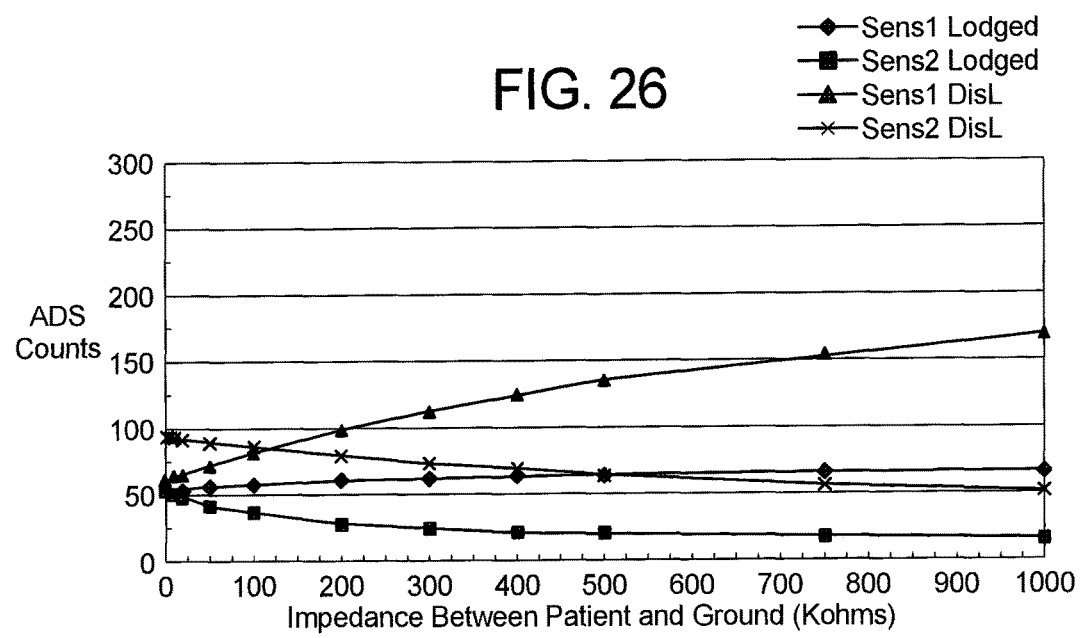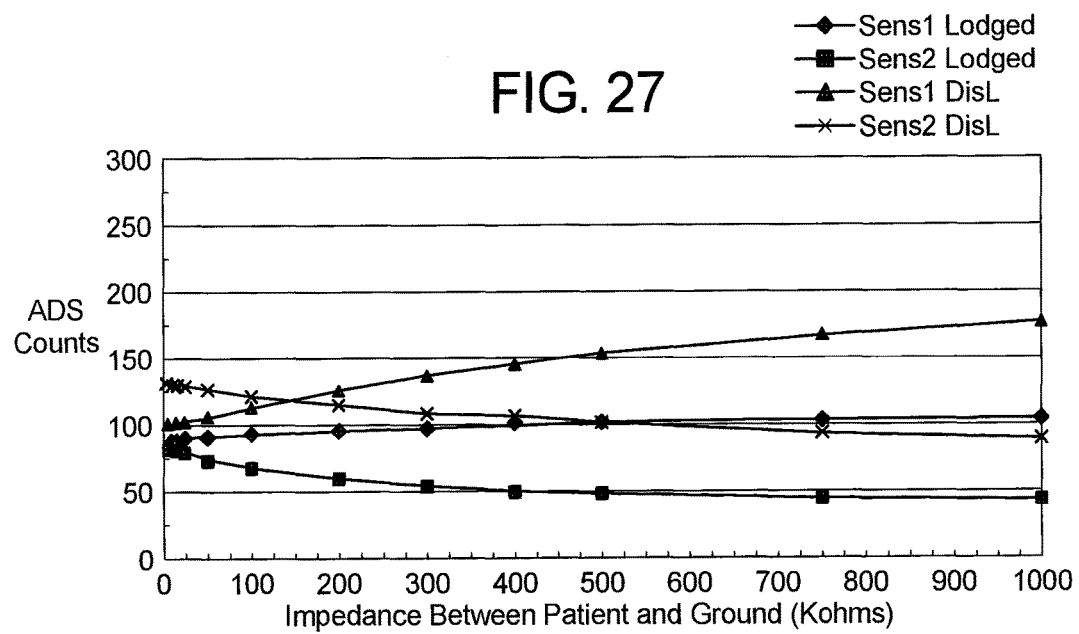

ENHANCED SIGNAL DETECTION FOR ACCESS DISCONNECTION SYSTEMS

PRIORITY CLAIM

This application claims priority to and the benefit as a continuation-in-part application of U.S. patent application "Conductive Polymer Materials And Applications Thereof Including Monitoring And Providing Effective Therapy", Ser. No. 10/760,849, filed Jan. 19, 2004, which is a continuation-in-part application of U.S. patent application "Access Disconnection Systems And Methods", Ser. No. 10/121,006, filed Apr. 10, 2002.

BACKGROUND

The present disclosure relates generally to patient access disconnection systems and methods for medical treatments. More specifically, the present disclosure relates to the detection of patient access disconnection, such as dislodgment of a patient access device during medical treatments or therapies including dialysis therapy.

A variety of different medical treatments relate to the delivery of fluid to and/or from a patient, such as the delivery of blood between a patient and an extracorporeal system connected to the patient via a needle or needles or any suitable access device inserted within the patient. For example, hemodialysis, hemofiltration and hemodiafiltration are all treatments that remove waste, toxins and excess water directly from the patient's blood. During these treatments, the patient is connected to an extracoporeal machine, and the patient's blood is pumped through the machine. Waste, toxins and excess water are removed from the patient's blood, and the blood is infused back into the patient. Needles or other suitable access devices are inserted into the patient's vascular access in order to transfer the patient's blood to and from the extracoporeal machine. Traditional hemodialysis, hemofiltration and hemodiafiltration treatments can last several hours and are generally performed in a treatment center about three to four times per week.

During any of these blood treatments, dislodgment of the access device can occur, such as dislodgment of a needle inserted into the patient's vascular access including an arterio-venous graft or fistula. If not detected immediately, this can produce a significant amount of blood loss to the patient. The risks associated with a needle dislodgment are considerable. Important criteria for monitoring blood loss include, for example, the sensitivity, specificity and response time with respect to the detection of needle dislodgment. With increased levels of sensitivity, specificity, and response time, the detection of needle dislodgment can be enhanced, and blood loss due to dislodgment can be minimized.

Typically, patients undergoing medical treatment, such as hemodialysis, hemofiltration or hemodiafiltration, are visually monitored in order to detect needle dislodgment. However, the needle may not be in plain view of the patient or medical staff (i.e., it may be covered by a blanket) such that it could delay detection and, thus, responsive actions to be taken in view of dislodgment, such as stopping the blood pump of the extracorporeal machine to minimize blood loss to the patient.

Moreover, in view of the increased quality of life, observed reductions in both morbidity and mortality and lower costs than in-center treatments, a renewed interest has arisen for self care and home hemodialysis therapies. Such home hemodialysis therapies (whether hemodialysis, hemofiltration or hemodiafiltration) allow for both nocturnal as well as daily treatments. During these self care and home hemodialysis sessions, especially during a nocturnal home hemodialysis session, when the patient is asleep, dislodgment risks are more significant because nurses or other attendants are not present to detect the dislodgment.

A need exists to make an access disconnection ("ADS") system operate as quickly as possible to minimize blood loss.

A need also exists to make the ADS system operate to without false triggers, which needlessly disrupt therapy and the patient.

A further need exists to provide such an ADS system readily and relatively inexpensively to machines already in use which may not have an ADS system or one that operate as well as the systems described herein.

SUMMARY

The present disclosure provides improved devices, apparatuses, systems, and methods for detecting dislodgment or disconnection of an access device, such as dislodgment of a needle inserted in a patient during dialysis therapy. The devices, apparatuses, systems and methods of the present disclosure utilize an electrical circuit with a number of electrical contacts which are in contact with the fluid circuit such that an electrical signal can be injected into at least a segment including, for example, a loop defined along at least a portion of the conducting fluid circuit. A direct-contact measurement can be used to provide immediate detection of a change in an electrical value in response to a change in access conditions, such as a change in impedance due to dislodgment of a needle or other access device from the patient during medical therapy including, for example, dialysis therapy and medication delivery.

The devices, apparatuses, systems and methods of the present disclosure in one embodiment are provided in a stand-alone, retrofit package that can be mounted to and made operable with an existing machine not having an ADS system or one that operates as well as the systems described herein. The stand-alone ADS system includes a detector module mounted to and operable with the blood tubing set and a protector module mounted to and made operable with the blood treatment, e.g., hemodialysis machine. The detector module and protector module communicate wirelessly, e.g., via radio frequency, in one embodiment. The detector module detects an access disconnection and sends a corresponding output to the protector module, which is configured then to clamp one or both the venous and arterial tubing. The clamping of the tubing will cause an increase in pressure, for example in the venous line, which is detected by the hemodialysis machine and causes the blood pump to shut down.

Described below are multiple systems for enhancing impedance signal output and reducing disposable cost. One problem with the impedance sensing systems is the effect of patient grounding. The dialysis system is connected to earth ground through the dialyzer and dialysate path for safety reasons. The patient can become electrically at the same potential as earth ground despite attempts to shield the patient. When this happens a ground current path can exist between the patient and the system's isolated ground even upon a needle dislodgment, making the system ineffective.

One apparatus and method for combating the effects of patient grounding is to use a two outputs of a signal source to create two points of equal potential on either side of a section of the dialysate or ground path. This causes a virtual open circuit to exist between the points, breaking the current path from earth ground to the system's isolated ground.

This technique is used alternatively or additionally to stop a portion of the signal current from flowing through the blood pump. In the systems below, current is induced into the blood using a voltage source and high resistance resistor. The current is normally split into two paths, one going through patient access, the other through the blood pump. It is desirable from a sensing standpoint for all of the current to go through the patient access path and none through the blood pump path. If too much current flows through the blood pump path, the increase in impedance due to a needle dislodgment may not be great enough to overcome a threshold. The above-described open circuit creating circuitry is accordingly placed in the blood pump path. This virtually precludes current from flowing through blood in the blood pump path, forcing virtually all the current through the patient access pathway.

Another apparatus and method for combating the effects of patient grounding is to move the blood circuit contacts as close to the patient as possible. It has been determined that reducing the impedance from the blood circuit contacts to the patient access is beneficial at least in part because it minimizes the effect of parallel current paths. This can be done by moving the blood circuit contacts as close to the patient as possible, minimizing the tubing lengths from the contacts to the patient access and thus the impedance in such tubing lengths.

A further apparatus and method for combating the effects of patient grounding is to place a second sensing circuitry in the ground current path, e.g., in the dialysate path. Here, a pair of contacts is added to the dialysate tubing. These contacts are not disposable and therefore do not add to disposable cost. The impedance in the ground path increases upon a needle dislodgement. A patient to earth ground path alone can be used to detect a patient access. If the patient is not grounded, the circuitry detects this condition and causes the system to use the blood circuit sensing circuitry instead for access disconnection detection. In a further alternative implementation, the system combines the signals from the blood circuit circuitry and the ground loop circuitry to detect and access disconnection.

Further described below is a system and method for detecting an access disconnection using the dialysate path. Here, multiple sets of contacts are placed in the to- and from-dialyzer dialysate tubing. The above-described open circuit creating circuitry is connected to two of the contact pairs, creating electrical opening circuits between the contacts. This forces all induced current induced into the dialysate circuit to flow through the dialyzer, the blood circuit and patient access to ground. The patient is grounded so that the current returns through earth ground to the system's isolated ground. The system provides a ground strap connected to the patient, e.g., through a blood pressure cuff. The ground strap can be connected to earth or system ground. This system is advantageous because it places the fluid contacts in the dialysate path where they do not have to be discarded after each therapy.

An advantage of the present disclosure is to provide an improved device, apparatus, system and/or method for detecting access disconnection.

A further advantage of the present disclosure is to provide an improved device, apparatus, system and/or method for detecting dislodgment of an access device from a patient during medical therapy including dialysis therapy.

Another advantage of the present disclosure is to provide an improved device, apparatus, method and/or system for detecting needle drop-out during dialysis therapy.

Yet another advantage of the present disclosure is to provide a sensitive, specific and responsive apparatus and/or device for detecting access disconnection during selfcare and home hemodialysis treatments.

Moreover, an advantage of the present disclosure is to provide a viable device or apparatus for allowing a patient or other non-medical personnel in a non-medical facility to administer a dialysis therapy that uses a portion of the patient's circulatory system.

Still further, an advantage of the present disclosure is to provide an improved apparatus for detecting access disconnection that uses a direct conductivity measurement.

Yet still further, an advantage of the present disclosure is to provide an access disconnection detection device, method and/or system that employs an electrical circuit in fluid and electrical contact with blood flowing through a blood circuit allowing direct conductivity measurements to be made.

Furthermore, an advantage of the present disclosure is to provide an improved device, system and method for monitoring and/or controlling blood loss from a patient.

Another advantage of the present disclosure is an improved method for dialysis that employs an apparatus, device, and/or system capable of detecting access disconnection, such as dislodgment of a needle inserted into a patient through which blood flows during dialysis therapy, and minimizing any resulting blood loss.

Yet another advantage of the present disclosure is an improved device for connecting an electrical contact to a fluid circuit allowing fluid and electrical communication between the electrical contact and fluid flowing through the fluid circuit.

Still another advantage of the present disclosure is an improved apparatus, device, system and/or method for detecting access disconnection, such as needle drop-out during dialysis therapy, with enhanced sensitivity, accuracy and responsiveness.

Yet still another advantage of the present disclosure are improved apparatuses, devices, systems and/or methods for the detection of fluid loss due to, for example, dislodgment of a single access device during medical therapies, for example, medication delivery and single needle hemodialysis therapies.

Yet still a further advantage of the present disclosure are improved apparatuses, devices, systems and/or methods for the detection of fluid loss due to, for example, dislodgment of a single access device during medical therapies, which can be retrofitted to an existing machine not having an ADS system or one that operates as well as the systems described herein.

A further still advantage of the present disclosure is to provide an access disconnection system that combats the effects of patient grounding and enhances the sensed impedance by creating an open circuit in the ground current path.

Another advantage of the present disclosure is to provide an access disconnection system that combats the effects of patient grounding by moving the blood contacts close to the patient.

A further advantage of the present disclosure is to provide an access disconnection system that combats the effects of patient grounding by placing a second sensing circuitry in the ground current loop.

Yet another advantage of the present disclosure is to provide an access disconnection system that places the fluid contacts in the dialysate circuit, such that the contacts are not disposable.

Additional features and advantages of the present disclosure are described in, and will be apparent from, the following Detailed Description and the figures.

BRIEF DESCRIPTION OF THE FIGURES

FIGS. 5A and 5B illustrate a coupler according to an embodiment of the present disclosure.

FIGS. 7A and 7B illustrate a sensor assembly according to an embodiment of the present disclosure.

FIGS. 24 to 27 are various plots of digitized sensed lodged versus dislodged impedance signals versus kOhms for both sensing circuitries of the system of FIG. 23.

DETAILED DESCRIPTION

Figure 1A:
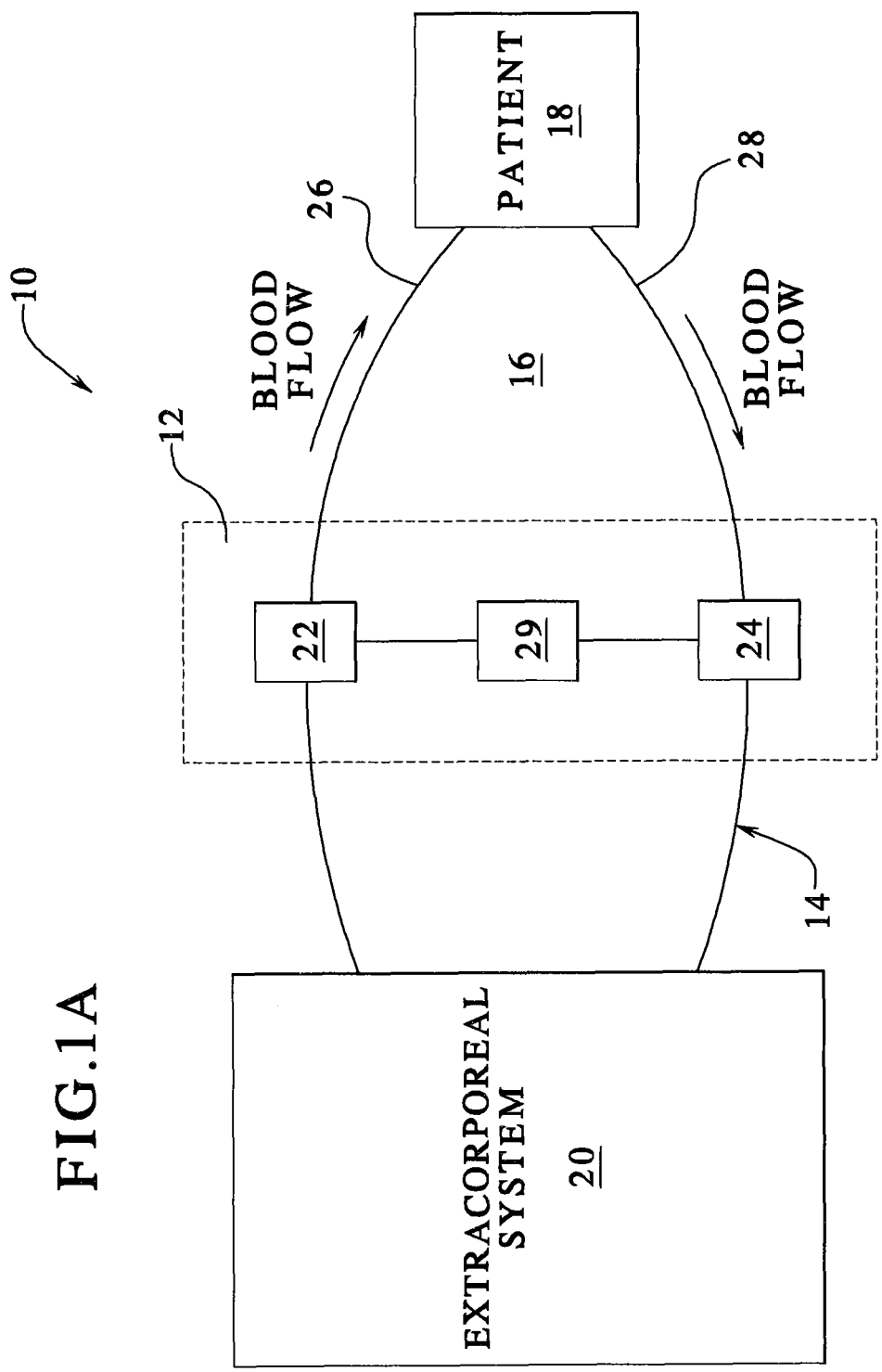
FIG. 1A illustrates a schematic view of an embodiment of the present disclosure showing two needles insertable within a patient through which blood flows to and from an extracorporeal system.

The present disclosure provides medical devices, apparatuses, systems and methods for detecting access disconnection. More specifically, the present disclosure provides medical devices, apparatuses, systems, and methods that employ, in part, an electrical circuit with electrical contacts in fluid contact and electrical communication with a fluid circuit allowing a direct conductivity measurement to be used such that dislodgment of a needle or other access device through which fluid flows between a patient and the fluid circuit can be immediately detected. Fluid loss (e.g., blood loss) due to, for example, dislodgment of a needle from a patient undergoing medical treatment, such as dialysis therapy, medication delivery or the like, can be controllably minimized.

It should be appreciated that the present disclosure is not limited to the detection of needle dislodgment but can be utilized to detect the dislodgment or disconnection of any suitable access device. As used herein, the term "access disconnection" or other like term can mean any suitable condition or event which can cause a loss or leak of an electrically conductive fluid flowing along a fluid circuit connected to the patient provided that a change in the electrical continuity between electrical contacts coupled to the fluid circuit can be detected. It should be appreciated that a change in the electrical continuity as measured by an electrical value, such as impedance, may be detected even in the absence of dislodgment of an access device from the patient. The term "access device" as used herein or other like term can mean a suitable device that can be inserted within a patient such that fluid, including blood, can pass to, through and/or from the patient via the access device. The access device can include a variety of different and suitable shapes, sizes and material make-up. Examples of an access device include needles, catheters and cannulas. The access device can be made of any suitable material including, for example, stainless steel, plastic or like biocompatible materials.

Although in the embodiment set forth below the apparatus and/or device is designed for use in a dialysis therapy, such as hemodialysis, hemofiltration or hemodiafiltration, it should be noted that the present disclosure can be used in a number of different medical therapies that employ a variety of different and suitable fluid systems, such as extracorporeal blood systems. For example, the systems of the present disclosure can be used during intravenous infusion that can employ the use of a single needle insertable within the patient for delivering a medical solution or drug, blood, blood products, processed blood or the like between the patient and the fluid system. In addition, the systems of the present disclosure can be used in plasma exchange therapies, in which a membrane is used to separate whole blood into plasma and cellular components.

With respect to dialysis therapy, the systems of the present disclosure can be used in a variety of different therapies to treat kidney failure. Dialysis therapy as the term or like terms are used throughout the text is meant to include and encompass any and all forms of therapies that utilize the patient's blood to remove waste, toxins and excess water from the patient. Dialysis therapies include hemodialysis, hemofiltration, hemodiafiltration, and continuous renal replacement therapy ("CRRT"). CRRT includes slow continuous ultrafiltration ("SCUF"), continuous veno-venous hemofiltration ("CVVH"), continuous veno-hemodialysis ("CVVHD") and continuous veno-venous hemodiafiltration ("CVVHDF"). Dialysis therapy can also include peritoneal dialysis, such a continuous ambulatory peritoneal dialysis, automated peritoneal dialysis and continuous flow peritoneal dialysis. Further, although the present disclosure, in an embodiment, can be utilized in methods providing a dialysis therapy for patients having chronic kidney failure or disease, it should be appreciated that the present disclosure can be used for acute dialysis needs, for example, in an emergency room setting. Last, the intermittent forms of therapy (i.e., hemofiltration, hemodialysis and hemodiafiltration) may be used in in-center, self/limited care as well and home settings.

In an embodiment, the systems of the present disclosure include an electrical circuit with a number of electrical contacts, such as a pair of electrical contacts, in fluid contact and electrical communication with the fluid circuit. The electrical contacts can include any suitable device through which electrical connection can be made with the fluid circuit to define a conductive pathway or conductor loop therein. Changes in an electrical value or any suitable parameter associated with the conductor loop can then be monitored in response to changes in access conditions as described below. In an embodiment, the electrical contact includes an electrode which can be coupled to the fluid circuit such that an electrical connection can be made in fluid contact with fluid flowing through the fluid circuit as discussed below.

For example, a constant current or other suitable electrical signal can be injected into the fluid circuit via an electrode pair in contact with the fluid flowing in between the electrodes to define a loop along at least a portion of the conducting fluid circuit. A change in an electrical value, e.g., impedance, can then be measured in response to access disconnection. This can provide a direct conductivity measurement capable of detecting a change in impedance or other suitable electrical parameter of the fluid, such as an electrically conductive fluid including blood, medical solutions or the like, as it flows between a patient and a fluid system (i.e., an extracorporeal blood system) via a needle, needles or other access device(s) inserted within the patient.

The systems of the present disclosure can effectively detect dislodgment of a needle (e.g., a venous needle and/or an arterial needle) or other access device through which blood or other suitable fluid can flow, for example, to, through, and from the patient, such as a blood circuit used during dialysis therapy. The detection capability of the present disclosure is believed to be immediate based on the measurable change in, for example, impedance of the electrically conductive fluid or fluids due to fluid loss resulting from disconnection of the access device from the patient.

The immediate detection capabilities of the present disclosure are important, particularly as applied to dialysis therapy where a significant amount of blood loss can occur within a relatively short period of time if delays in detection and responsive actions to stop the blood loss occur. Under typical dialysis conditions, if twenty seconds or more time elapses before blood loss due to dislodgment is detected and stopped, over one-hundred milliliters of blood can be lost based on typical blood flow rates of four-hundred milliliters/minute.

Applicants have discovered that the present disclosure can detect access disconnection, particularly in response to venous needle dislodgment during dialysis therapy, with a high degree of sensitivity and specificity in addition to its immediate detection capabilities. The direct-contact measurement of the present disclosure is capable of detecting a change of an electrical value, e.g., impedance, due to needle dislodgment or the like as the blood flows through the blood circuit during dialysis therapy. As used herein, the term "electrical value" or other like terms means any suitable electrical parameter such as, impedance, resistance, voltage, current, rates of change thereof and combinations thereof. The detection of a change in impedance or the like is an indication that the needle has become dislodged or other like condition has occurred. It is noted that the detection capabilities of the present disclosure can also effectively detect blood loss during medical therapy resulting from a disconnection in the fluid circuit, even if the needle or needles have not become dislodged. The systems of the present disclosure can controllably minimize blood loss from the patient based on the ability of the present disclosure to immediately measure a change in impedance or the like due to blood loss with a high degree of sensitivity and specificity.

The devices and apparatuses of the present disclosure can include a variety of different components and configurations depending on the applied medical therapy such that fluid loss, particularly blood loss due to needle dislodgment or the like, can be effectively monitored.

Multiple Access Disconnection

Referring now to FIG. 1A, an embodiment of the apparatus 10 of the present disclosure includes a pair of electrical contacts 12 in fluid contact with a blood tubing set 14 of a blood circuit 16. The blood circuit 16 connects a patient 18 to an extracorporeal blood system 20 as applied to, for example, dialysis therapy including hemodialysis, hemofiltration, hemodiafiltration, continuous renal replacement or the like or plasma therapies. The pair of electrical contacts 12 includes a first electrical contact 22 and a second electrical contact 24 which are attached to a respective first tube member 26 and second tube member 28 of the blood circuit 16. The first tube member 26 is connected to a venous needle or other suitable access device inserted into a vascular access region (not shown) of the patient. The second tube member 28 is connected to an arterial needle or the like also inserted into a vascular access region (not shown) of the patient. During dialysis therapy, for example, blood flows from the patient 18 through the arterial needle to the extracorporeal blood system 20 (e.g., a dialysis machine) via the second tube member 28 where the blood is treated and delivered to the patient 18 through the venous needle via the first tube member 26.

As the blood flows through the blood circuit during dialysis therapy, a controller 29 and associated electronics generates a constant electric current or the like, which is injected or passed into the flowing blood via the electrical contact pair 12, e.g., an electrode pair as described below. The electrode pair 12 connected to the controller 29 or other suitable electronic device can then be used to measure a voltage change across an unknown fluid (e.g., blood) impedance or other like electrical value to detect a change in impedance or the like across the vascular access region. In an embodiment, one electrode can be used to inject the electrical signal into the fluid circuit, while the other electrode of the pair can be used to sense a change in the electrical value and pass an electrical signal indicative of the same to the controller for processing and detection purposes. Upon dislodgment of at least one of the venous needle and arterial needle from the blood circuit or other suitable condition, an immediate and detectable increase in impedance or the like can be measured as compared to the impedance or other suitable parameter measured under normal operating conditions.

It should be appreciated that the present disclosure as embodied in FIG. 1A can be modified in a variety of suitable ways depending on the medical therapy as applied. For example, the venous and arterial needles can be inserted into the vascular access of the patient at any suitable part of the patient's body, such as the upper arm, lower arm, upper thigh area or the like during dialysis therapy. As previously discussed, the present disclosure can be applied to a variety of different medical therapies including intravenous infusions, plasma exchanges, medication delivery, drug delivery, blood delivery and dialysis therapies (i.e., hemofiltration, hemodialysis, hemodiafiltration and continuous renal replacement).

Figure 1B:
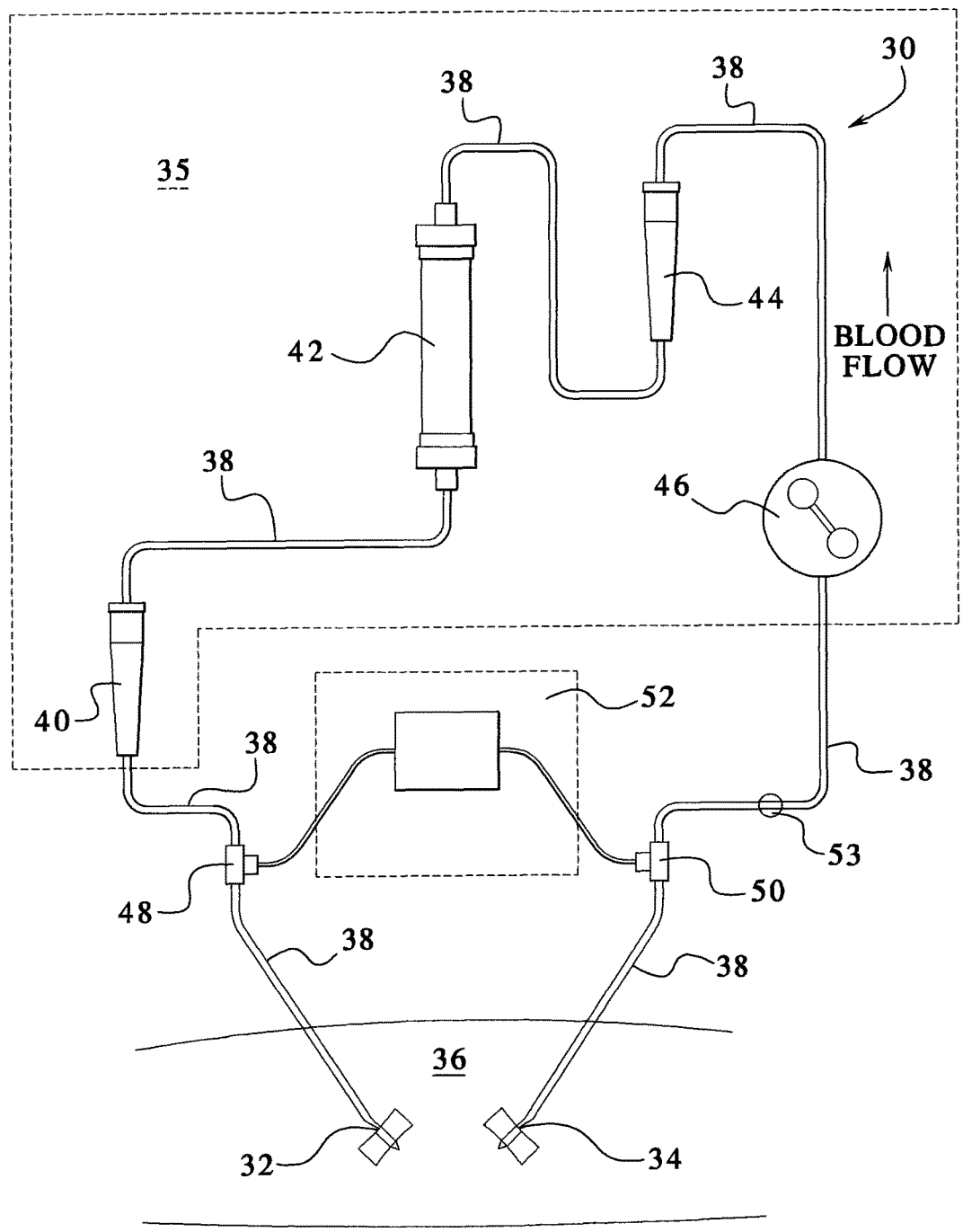
FIG. 1B illustrates a schematic view of an embodiment of the present disclosure capable of detecting needle dislodgment during dialysis therapy.

As illustrated in FIG. 1B, an embodiment of a system 30, such as a dialysis system, of the present disclosure is shown as applied during dialysis therapy. In an embodiment, the present disclosure includes a venous needle 32 and arterial needle 34 inserted within a patient access 36. The venous needle 32 and arterial needle 34 are connected to blood circuit 35 via venous line 26 and arterial line 28, respectively. Other tubes 38 connect various components of blood circuit 35 including, for example, a venous drip chamber 40, a dialyzer 42, an arterial drip chamber 44 and a blood pump 46. It should be appreciated that one or more of the components of the dialysis system can be provided within a dialysis machine coupled to the blood circuit.

As shown in FIG. 1B, a first electrical contact coupling device 48 and a second electrical contact coupling device 50 are positioned in blood circuit 35 between the venous needle 32/arterial needle 34 and the tubes 38 connecting venous drip chamber 40, dialyzer 42, arterial drip chamber 44 and a blood pump 46. As used herein, the term "electrical contact coupling device," "coupling device" or other like term can mean any suitable device that can be used to connect an electrical contact to the fluid circuit. In an embodiment, the electrical contact coupling device can be used to contact the electric contact to the fluid circuit allowing fluid contact and electrical connection with the fluid flowing through the fluid circuit as described below.

In an embodiment, the electrical contact pair is connected to a controller 52 or other suitable electronic device. The controller can be used to inject an electric signal via the electrode pair and into the blood and/or other fluid as it flows through the blood circuit. This provides a conductor loop along which changes in electrical parameters or values can be measured. Controller 52, which is coupled to the electrode pair, can also be used to measure this change. It should be appreciated that controller 52 can include a single electronic device or any suitable number of devices in electrical connection with the electrical contacts to input an electrical signal into the blood circuit to define a conductor loop, to measure a change in an electrical parameter or value associated with the conductor loop and/or perform any other suitable task, such as processing the detectable signal as discussed below.

The electrical signal is generated in one embodiment from a constant current that is supplied to the electrodes until dislodgment occurs. The voltage across an unknown impedance of the fluid (e.g., blood) circulating through the blood circuit can then be measured to detect a change in impedance due to changes in access conditions. However, it should be appreciated that any suitable electrical parameter and changes thereof can be monitored to detect needle drop-out or the like as previously discussed.

As demonstrated below, the detection capabilities of the present disclosure are highly sensitive, specific and virtually immediate in response to access disconnection, such as needle dislodgment. Further, the electronic circuit of the present disclosure is relatively simple in design, in which only one electrode pair is necessary to conduct direct conductivity measurement. This can reduce costs and effort as compared to known vascular access monitoring techniques that only employ non-invasive detection techniques, such as, capacitive couplers and induction coils as previously discussed.

Applicants have discovered that the total impedance measured ("Z") can be modeled as two lumped impedances in parallel with one impedance ("$Z_D$") being produced by the pump segment, the dialyzer, the drip chambers and/or other suitable components of the dialysis system and/or the like. The other impedance component ("$Z_P$") is formed by the patient's vascular access and associated tubing, which carries blood to and from the vascular access and/or the like. The total impedance measured can be characterized as a function of both $Z_D$ and $Z_P$ as follows:

$$Z=(1/Z_D+1/Z_P)^{-1}$$

Despite this parallel impedance, Applicants have discovered that the electrical contacts in connection with the controller can be used to measure a change in impedance along the conductor loop as blood flows through the blood circuit in response to access disconnection, such as needle dislodgment. If needle dislodgment occurs, the conductor loop along at least a portion of the fluid circuit changes from a closed circuit to an open circuit and thus $Z=Z_D$ where $Z_P$ approaches infinity. The direct conductive measurement capabilities of the present disclosure can be effectively used to detect access disconnection.

Applicants note that the $Z_D$ component can produce a level of electrical interference associated with the time-varying high impedance of the components of a medical system coupled to the fluid circuit, such as a dialysis system and its components including, for example, a blood pump, a drip chamber and/or the like. Applicants have discovered that the interference due to the $Z_D$ component can be effectively eliminated, or at least reduced, if necessary. In an embodiment, the signal associated with the detection of Z or the like can be further processed as discussed below. Alternatively, in an embodiment, the electrical circuit of the present disclosure can be designed to block or bypass one or more components of the dialysis system from the conductor loop or pathway defined along the blood circuit as described below. The accuracy, sensitivity and responsiveness with respect to the detection of access disconnection can be enhanced.

In an embodiment, a third electrical contact point 53 can be utilized to minimize or effectively eliminate the interferences with respect to the high impedance components coupled to the blood circuit, such as the blood pump and the like. The additional contact point can be made in any suitable way. For example, the third contact point can be an electrode or other suitable device through which electrical continuity can be established between it and one of the electrodes of the coupling devices. In an embodiment, the third electrical contact can be attached to a fluid circuit in fluid and electrical communication with fluid flowing through same.

The third contact point 53 can be positioned at any suitable position along the blood circuit. Third contact point 53 in the illustrated embodiment is positioned at any suitable location between the blood pump 46 and arterial coupling device 50 as shown in FIG. 1B. An equalization potential can then be applied between the third contact point 53 and the electrode of the coupling device 50. The potential is applied at a voltage that is equal to the potential applied between the electrodes of the first coupling device 48 and the second coupling device 50.

This effectively causes the electric current or the like, once injected into the blood circuit, to bypass one or more of the components of the dialysis system. In an embodiment, the third contact point 53 can be positioned such that the electric current or the like would effectively bypass all of the components of the dialysis system as shown in FIG. 1B. That is, the same voltage applied at contacts 50 and 53 creates a virtual open circuit between contacts 50 and 53, such that a current injected into tubes 38 by controller and associated electronics 52 at either coupler 48 or 50 virtually completely follows the path of least resistance though venous tube 26, arterial tube 28 and patient access 36, rather than splitting through those tubes/patient access 36 and the remainder of the extracorporeal circuit including venous drip chamber 40, dialyzer 42, arterial drip chamber 44 and a blood pump 46.

Single Access Disconnection

Figure 1C:
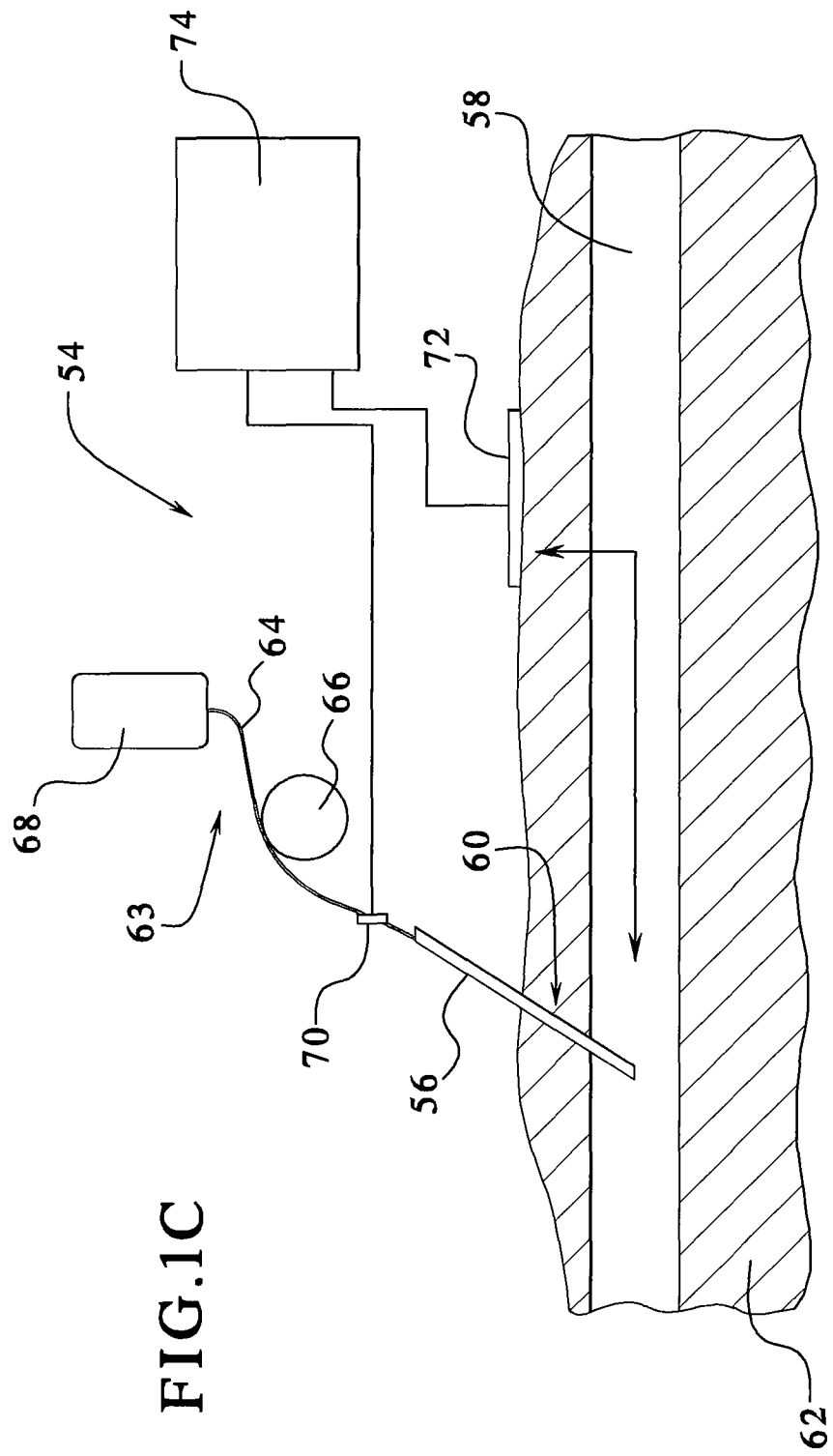
FIG. 1C illustrates a perspective view of an embodiment of the present disclosure showing access disconnection detection capabilities during medical therapies administered via a single needle.

The electrical contacts of the present disclosure can be positioned in any suitable location relative to the needle, needles or suitable access device inserted within the patient. As illustrated in FIG. 1C, an embodiment of the present disclosure as applied with respect to the detection of access detection, such as the dislodgment of a single access device inserted within the patient is shown. This type of application is applicable to a variety of different and suitable medical therapies administered via a single access device, such as a single needle, including intravenous infusion and dialysis therapy including hemodialysis, hemofiltration, hemodiafiltration and continuous renal replacement.

As applied, an electrically conductive fluid, such as blood, a blood product, a medical fluid or the like flows between the patient and a fluid system via a single access device. Dislodgment detection of a single access device can include, for example, the detection of needle dislodgment during the delivery of any suitable and electrically conductive fluid or fluids including, for example, blood or medical drug or solution (e.g., a medication contained in an electrically conductive fluid, such as saline), processed blood, blood products, intravenous solutions, the like or combinations thereof. The fluid delivery can be made between a suitable container, such as blood bags or like fluid delivery devices, and a patient. The systems of the present disclosure monitor and control the needle access so as to provide immediate and responsive detection of access disconnection of a blood or medical fluid access, such as a medication or drug, during medical therapy administered via a single needle.

As shown in FIG. 1C, an embodiment of the apparatus or device 54 of the present disclosure includes an access device 56; such as a needle, inserted into a blood vessel 58 within a needle insertion site 60 of the patient 62. The needle 56 is connected to the fluid system 63, such as a fluid infusion system, via a tube member 64. The infusion system includes, for example, an infusion pump 66 for transferring the blood or the like from a container 68 (e.g., blood bag) to the patient. A first electrical contact 70 is spaced apart from the needle 56 along the tube member 64 and a second electrical contact 72 is attached to the patient near the insertion site 60. The first electrical contact 70 is in fluid contact with the fluid as it flows from the delivery container 68 to the patient.

In this configuration, the first and second electrical contacts, e.g., electrodes, can be used to monitor changes in an electrical value, e.g., impedance, within a conductor loop formed by at least a portion of the fluid circuit as an electric signal passes therein. The electrical contact points can be coupled to an electronic device 74, which is capable of processing a detectable signal transmitted through the electrodes in response to a change in impedance or the like due to dislodgment of the single access device as described in detail below. The electrical signal in one embodiment is generated by a constant current supplied to the electrodes such that a direct conductivity measurement can be conducted to detect a change in impedance or the like in response to changes in vascular access conditions, such as dislodgment of the access needle.

It is believed that the measured impedance, in the single needle application, is a function of both the impedance of the fluid (i.e., blood) and the impedance as measured across the insertion site. The electronic device 74 can be adjusted to detect the impedance at the level equivalent to the combined impedance of all items of the electrical path (i.e., the conductive fluid in the tube, needle, blood stream of venous vessel, body tissue, impedance across the skin with respect to the sensing electrode 72 and the like).

Electrical Contacts

As previously discussed, the electrical contacts of the present disclosure are in fluid contact with the fluid as it flows through the fluid circuit. The electrical contacts allow for a direct conductivity measurement which is capable of immediately detecting, with high sensitivity and specificity, a change (e.g., an increase) in impedance or the like due to access disconnection, such as dislodgment of a venous needle (arterial needle or both) from the blood circuit during dialysis therapy.

The electrical contacts can be composed of any suitable conductive and biocompatible material, such as, any suitable electrode material including stainless steel, other suitable conductive materials or combinations thereof. It is essential that the electrode material is biocompatible.

It should be appreciated that the electrical contacts can be constructed in a variety of different shapes and sizes, illustrative examples of which are described below. For example, the electrical contacts can be configured or designed as a plaster electrode which includes an agent capable of expanding when in contact with moisture. The agent can include a variety of suitable materials including gels that are known to expand more than ten times in volume upon contact with moisture.

In an embodiment, the plaster electrode can be utilized to detect fluid (i.e., blood leakage) at an insertion site of an access device insertable within a patient during the administration of medical therapy via a single access device as previously discussed. Upon contact with the fluid, the plaster electrode would necessarily expand to such an extent that the electrode contact is broken, thus causing a detectable increase in impedance of the fluid as it flows from the fluid system to the patient via the needle.

In an embodiment, one or more electrodes (not shown), such as one or more plaster electrodes as previously discussed, can be used in combination with the electrical contact pair as shown, for example, in FIGS. 1A and 1B. For example, a plaster electrode can be attached to the patient near the insertion site of either or both of the arterial and venous needles. The plaster electrode(s) can be utilized to detect leakage of fluid, such as blood, from the insertion site of the access device(s).

In an embodiment, an electrode pair is coupled to the blood circuit in an invasive manner (illustrated in FIGS. 2A to 2C as discussed below) such that the electrodes contact the blood as previously discussed. An excitation source that includes a constant current source or the like can be applied to the electrodes to inject an electric signal into the blood circuit thereby defining a conductor loop along which direct conductivity measurements can be performed.

To ensure patient safety, the excitation source is typically isolated from the instrument power. The excitation source can produce a constant electrical current that passes through the blood via the electrodes. Any suitable amount of current can be generated for detection purposes. In an embodiment, the electrical current as it passes through the blood is maintained at a level of about ten microamperes or less, e.g., about five microamperes or less. It should be appreciated that the present disclosure can be operated at low levels of current (e.g., ten microamperes or less) such that the level of current has negligible, if any, effect on the health and safety of the patient.

It should be appreciated that the impedance or other suitable parameter can be measured and calculated in a variety of different and suitable ways. For example, the amplitude, phase and/or frequency of the constant current excitation source can be measured and varied during the detection of a change in impedance. Impedance levels can then be detected by measuring the voltage across the electrodes. The amplitude, frequency and/or phase of the voltage can then be measured and utilized in combination with the measured amplitude, frequency and/or phase of the excitation source to calculate blood impedance levels based on derivations or equations which are typically used to calculate impedance.

The electrical contacts can be connected to the blood circuit in a variety of different and suitable ways. For example, the electrical contacts can be an integral component of the extracorporeal system, a disposable component that can be connected and released from the tubing members of the blood circuit, a reusable component that can be autoclaved between uses, or the like.

Electrical Contact Coupling Device

In an embodiment, the apparatus of the present disclosure includes an electrical contact coupling device that can be utilized to secure the electrical contacts to the blood circuit such that the electrodes effectively contact the blood and, thus, can be used to effectively monitor changes in access conditions as previously discussed. The coupling device of the present disclosure can also be designed to facilitate the protection of the user against contact with potential electrical sources. In an embodiment, the device can include a conductive element connected to a tube, through which a medical fluid can flow wherein the conductive element has a first portion exposed to the medical fluid, such as blood, and a second portion external to the tube.

The coupling device of the present disclosure can include a variety of different and suitable configurations, components, material make-up or the like. In an embodiment, the present disclosure can include a device for connecting an electrical contact to a fluid conduit providing fluid and electrical communication between the electrical contact and fluid flowing through the fluid conduit. The device can include a first member including an annular portion capable of accommodating the electrical contact and a first stem portion connected to the annular member wherein the stem portion has an opening extending therethrough to the annular portion; a second member including a base portion with a groove region and a second stem portion with an opening extending therethrough to the groove region allowing the first member to be inserted and secured to the second member; and a contact member adapted to fit the first and second stem portions allowing the contact member to abut against at least a portion of the electrical contact member allowing an electrical connection to be made between the electrical contact and the contact member. Illustrative examples of the electrical contact coupling device of the present disclosure are described below.

Figure 2A:
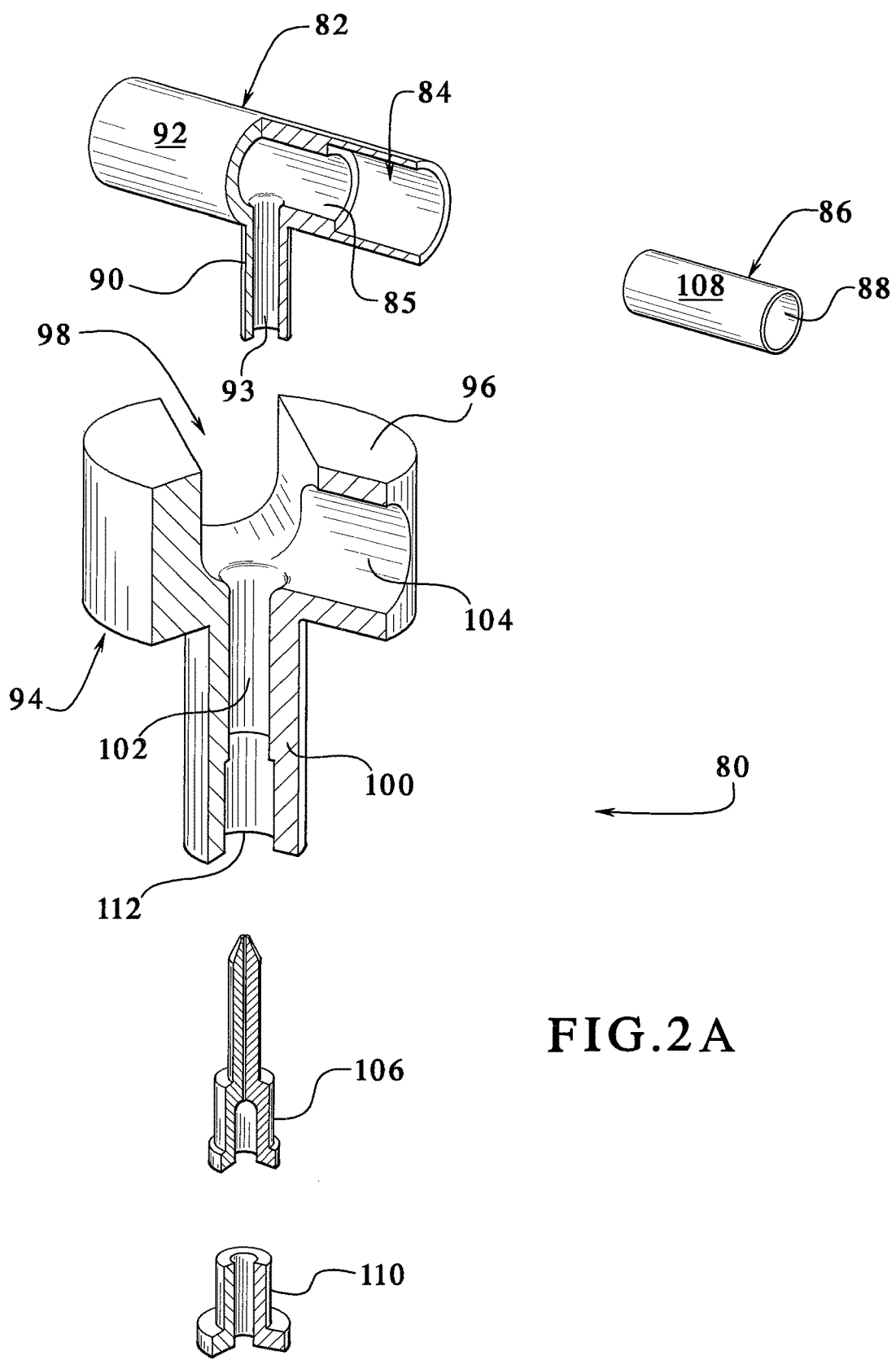
FIG. 2A illustrates an exploded view of an electrical contact coupling device in an embodiment of the present disclosure.
Figure 2B:
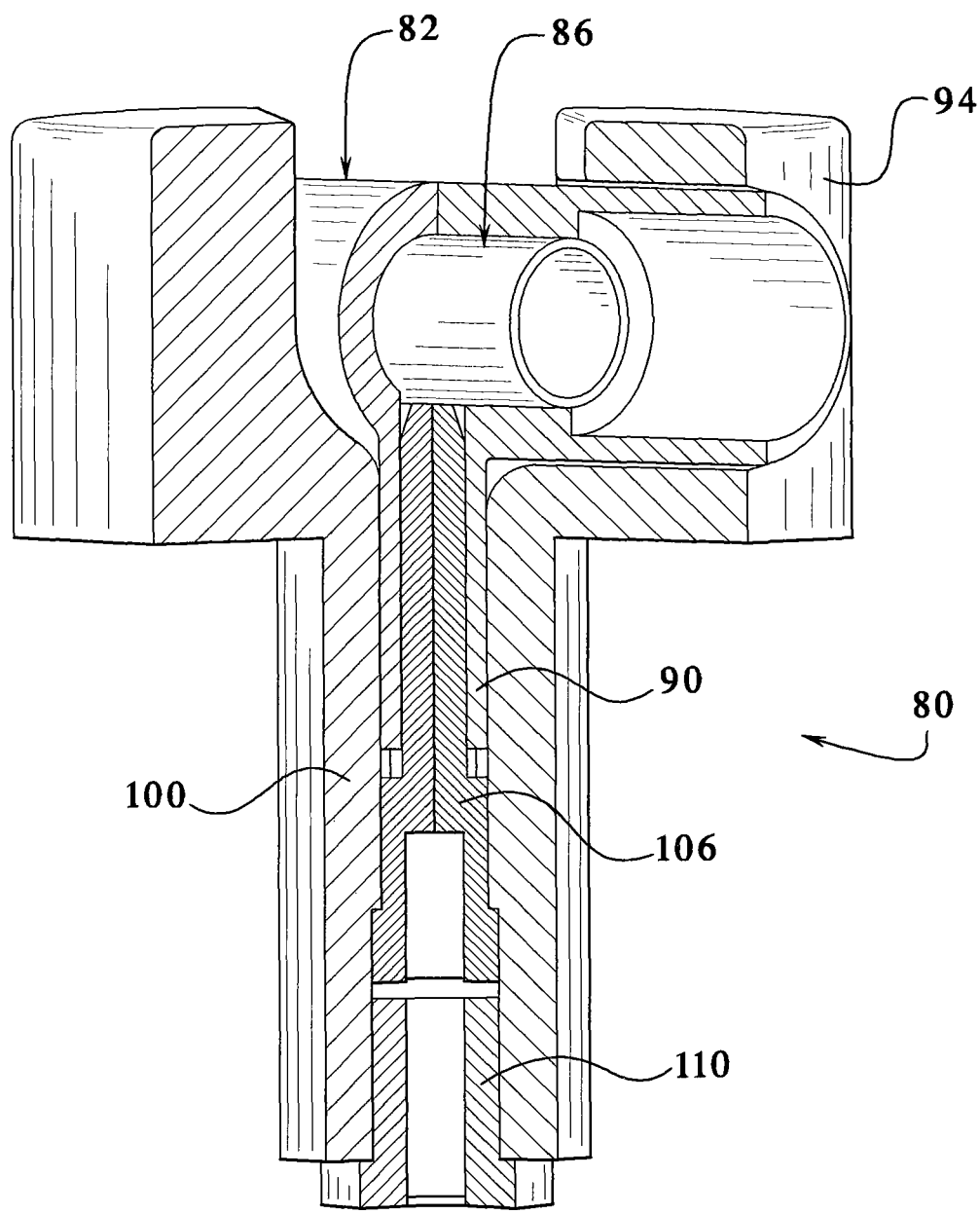
FIG. 2B illustrates a side sectional view of the coupling device of FIG. 2A in an embodiment of the present disclosure.

As illustrated in FIGS. 2A and 2B, the electrical contact coupling device 80 includes a probe member 82 that has a cylindrical shape with an opening 84 extending therethrough. An electrical contact, such as an electrode 86 having a cylindrical shape can be inserted into the opening 84 such that the electrode 86 is secure within the probe member 82. In an embodiment, the probe member 82 has a channel 85 extending along at least a portion of the opening 84 within which the electrode 86 can be inserted into the probe member 82. A tube member, for example, from a blood tubing set, connector tube member of a dialysis machine or the like, can be inserted into both ends of the opening 84 of the probe member 82 in contact with an outer portion of the channel 85 allowing blood or other suitable fluid to make fluid contact with the electrode 86 in any suitable manner. The electrode 86 has an opening 88 that extends therethrough within which blood (not shown) or other suitable fluid from the fluid circuit can flow. In an embodiment, the diameter of the opening 88 of the electrode 86 is sized to allow blood flow through the electrode 86 such that blood flow levels under typical operating conditions, such as during dialysis therapy, can be suitably maintained. The coupling device of the present disclosure can be readily and effectively attached to a fluid circuit, including a blood circuit or the like, for use during medical therapy including, for example, dialysis therapy. It should be appreciated that the coupling device 80 of the present disclosure can be attached to the fluid circuit in any suitable way such that electrical and fluid connection can be made with the fluid flowing through the fluid circuit.

The probe member 82 also includes a stem portion 90 that extends from a surface 92 of its cylindrical-shaped body. The stem portion 90 has an opening 93 that extends therethrough. In an embodiment, the stem portion 90 is positioned such that at least a portion of the electrode 86 is in contact with the opening 93 of the stem portion 90.

To secure the electrode 86 to the blood circuit, the coupling device 80 includes a socket member 94 that includes a body portion 96 with an opening 98 for accepting the probe member 82 and for accepting a blood tube member (not shown) of the blood circuit such that blood directly contacts the electrode as it circulates through the blood circuit during dialysis therapy. In an embodiment, the socket member 94 includes a stem portion 100 extending from the body member 96 wherein the stem portion 100 includes an opening 102 extending therethrough. As the probe member 82 is inserted through the opening 98 of the body member 96, the stem portion 90 of the probe member 82 can be inserted into the opening 102 of the stem portion 100 of the body 96 of the socket member 94.

In an embodiment, the socket member 94 includes a groove region 104 extending along at least a portion of the body 96 of the socket member 94. The probe member 82 can be inserted through the opening 98 and then moved or positioned into the groove region 104 to secure the probe member 82 within the body 96 of the socket member 94.

In an embodiment, the coupling device 80 includes an electrical contact member 106 that is inserted within the opening 102 of the stem portion 100 of the body 96 of the socket member 94 such that the electrical contact member 106 extends through the opening 93 of the stem portion 90 of the probe member 82 to contact at least a portion of a surface 108 of the electrode 86.

The electrical contact member 106 is utilized to connect the electronics (not shown) of, for example, the excitation source, a signal processing device, other like electronic devices suitable for use in monitoring and/or controlling changes in access conditions, such as needle dislodgment. The electrical contact member 106 can be made of any suitable material, such as any suitable conductive material including, stainless steel, other like conductive materials or combinations thereof. To secure the electrical contact member 106 in place, a contact retainer member 110 is inserted within the opening 102 of the stem portion 100 at an end region 112 thereof.

In an embodiment, the coupling device is mounted to a dialysis machine, device or system in any suitable manner. For example, the coupling device can be mounted as an integral component of the dialysis machine. The coupling device can also be mounted as a separate and/or stand alone component which can interface with any of the components of the apparatus and system of the present disclosure. In an embodiment, the coupling device 80 can be insertably mounted via the stem portion 100 of the socket member 94 to a dialysis machine or other suitable components.

Figure 2C:
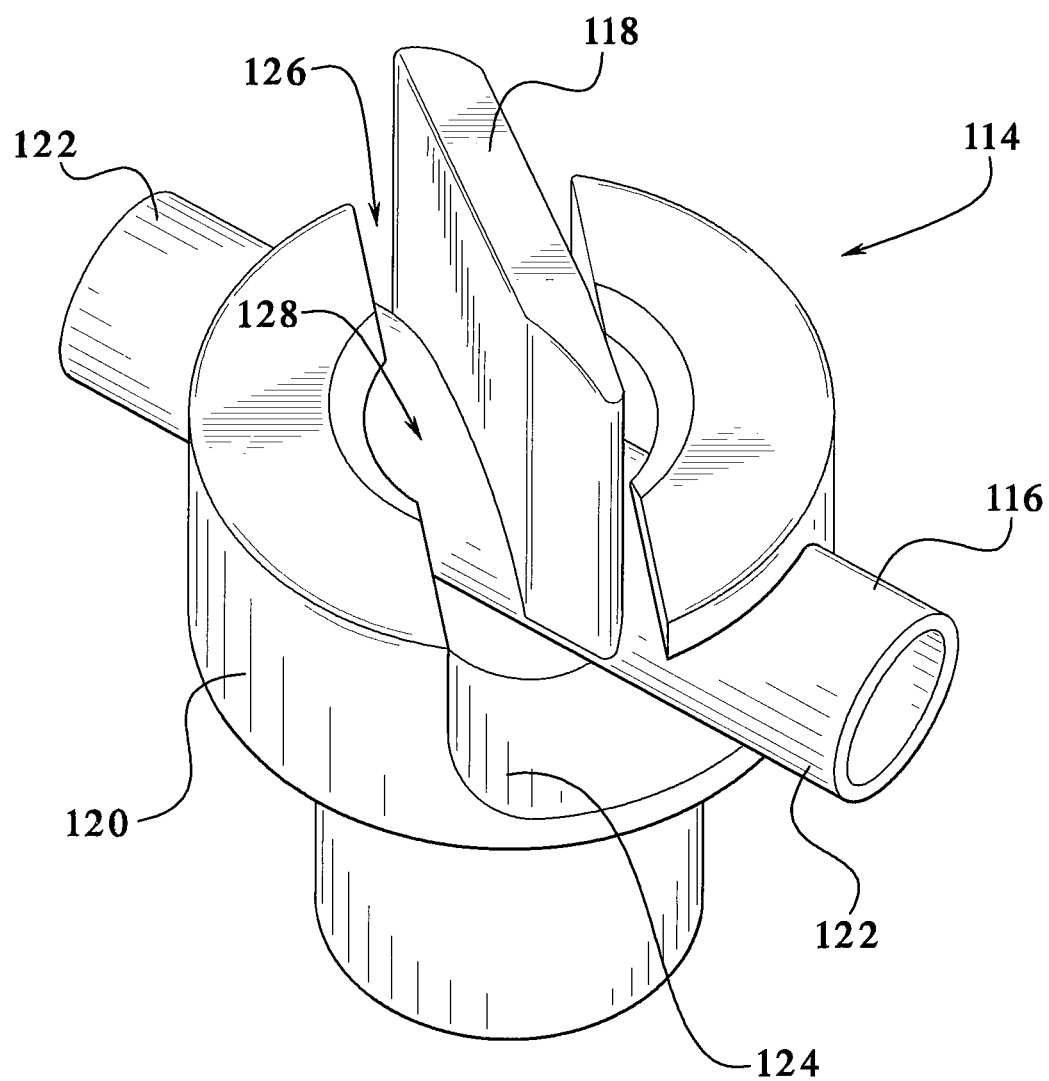
FIG. 2C illustrates another embodiment of the coupling device of the present disclosure.

It should be appreciated that the electrical contact coupling device can include a variety of different and suitable shapes, sizes and material components. For example, another embodiment of the coupling device is illustrated in FIG. 2C. The coupling device 114 in FIG. 2C is similar in construction to the coupling device as shown in FIGS. 2A and 2B. The coupling device 114 of FIG. 2C can include, for example, a cylindrical-shaped electrode or other suitable electrical contact, a probe member for accepting the electrode and securing it in place within a socket member of the sensing device. The probe member includes a stem portion that is insertable within a stem portion of the socket member. An electrical contact member is insertable within the stem portion such that it can contact the electrode. The coupling device of FIG. 2C can also include a contact retainer member to hold the electrical contact member in place similar to the coupling device as shown in FIGS. 2A and 2B.

As shown in FIG. 2C, the probe member 116 of the electrical contact coupling device 114 includes a handle 118 which can facilitate securing the probe member 116 within the socket member 120. The handle 118, as shown, has a solid shape which can facilitate the use and manufacture of the coupling device 114. In addition, the stem portion (not shown) of the probe member 116 is larger in diameter than the stem portion of the probe member as illustrated in FIG. 2A. By increasing the stem size, the probe member can be more easily and readily inserted within the socket member. Further, the probe member is greater in length as compared to the probe member as shown in FIGS. 2A and 2B such that the end regions 122 of the probe member 116 extend beyond a groove region 124 of the socket member 120. This can facilitate securing the probe member within the groove region 124 of the socket member 120.

In an embodiment, an opening 126 of the socket member 120 can include an additional opening portion 128 to accommodate the insertion of the stem portion of the probe member 116, having an increased size, therethrough. This can ensure proper alignment of the probe member with respect to the socket member before insertion of the probe member into the socket member thus facilitating the insertion process.

It should be appreciated that the probe member, socket member and contact retainer member can be composed of a variety of different and suitable materials including, for example, plastics, molded plastics, like materials or combinations thereof. The various components of the coupling device, such as the probe member, socket member and contact retainer member, can be fitted in any suitable way. For example, the components can be fitted in smooth engagement (as shown in FIGS. 2A and 2B), in threaded engagement (as shown in FIGS. 2D and 2E) and/or any suitable fitting engagement or arrangement to one another.

Figure 2D:
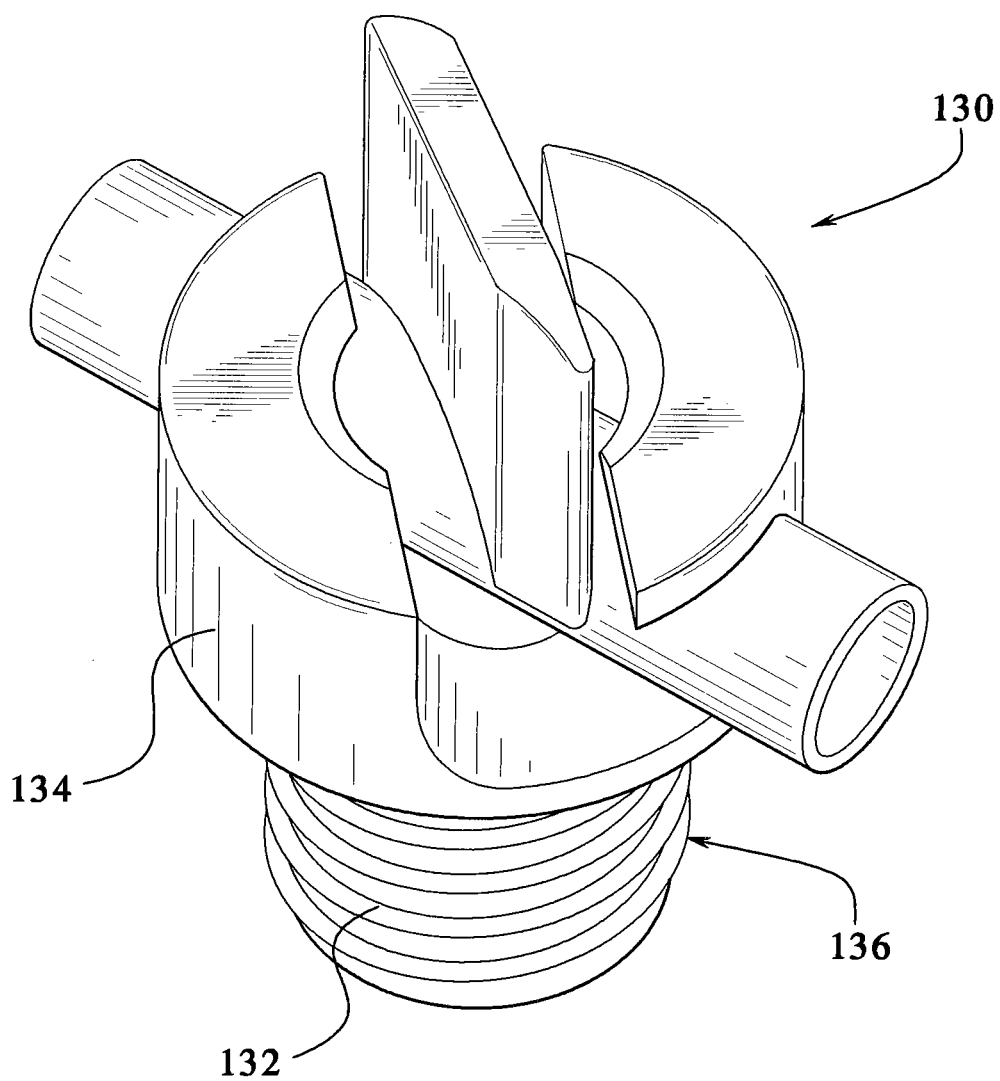
FIG. 2D illustrates another embodiment of the coupling device of the present disclosure showing a threaded engagement between the components of same.
Figure 2E:
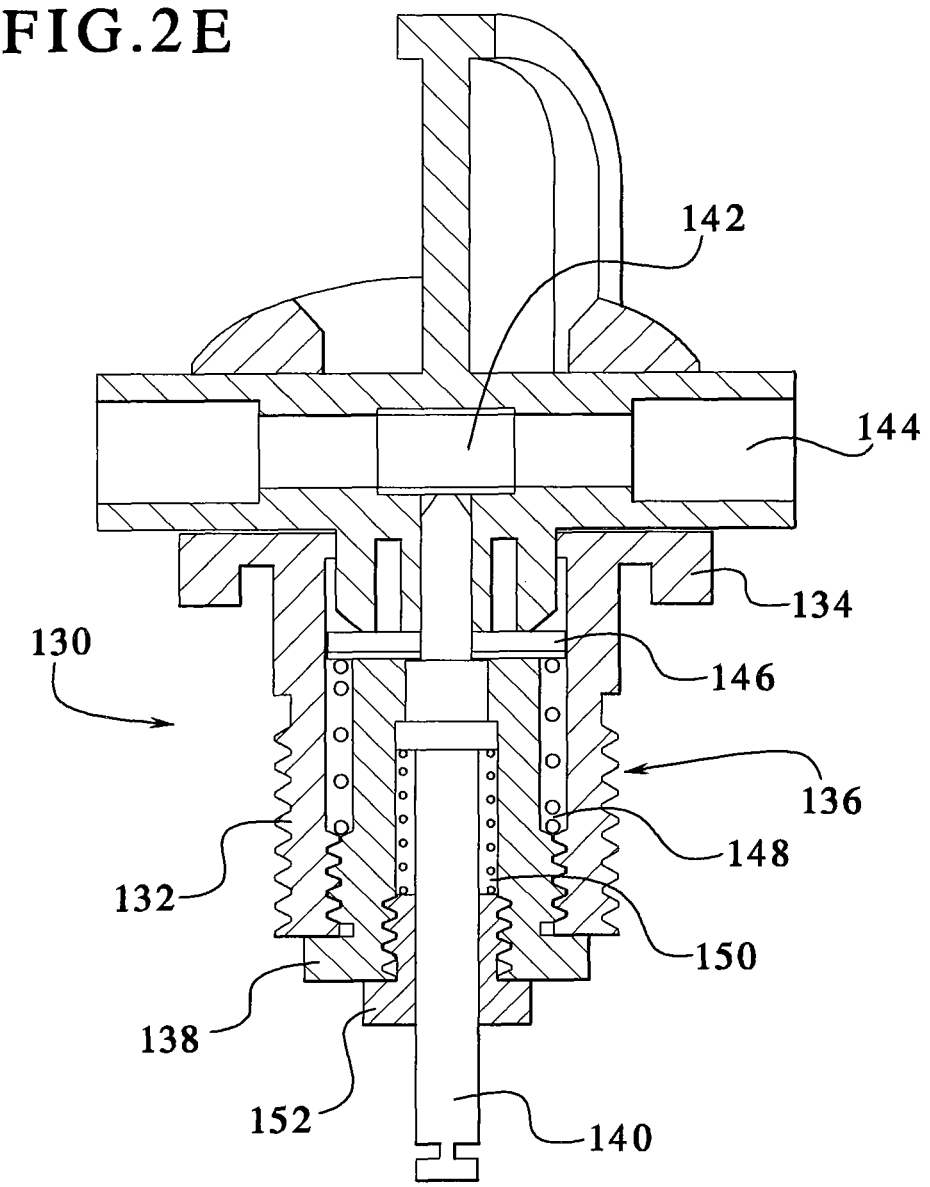
FIG. 2E illustrates a sectional view of FIG. 2D.

As shown in FIGS. 2D and 2E, the coupling device 130 of the present disclosure can be made of threaded parts, which are removably connected to one another to form the coupling device. The threaded parts can facilitate securing the electrode to the blood circuit as well as general use of same as described below.

In an embodiment, the stem portion 132 of the body 134 of the coupling device 130 has a threaded region 136, which can be insertably attached to a dialysis machine or other suitable mounting device in threaded engagement. This can facilitate the ease in which the coupling device is attached and detached from the mounting device.

As shown in FIG. 2E, the stem portion 132 is threaded on both sides allowing it to be in threaded engagement with an annular member 138. The annular member 138 provides direction and support allowing the electrical contact member 140 to abut against the electrode 142 housed in the probe member 144 as previously discussed.

In an embodiment, a plate member 146 made of any suitably conductive material can be depressed against a spring 148 as the probe member 144 is secured to the body 134. At the same time, another spring 150 can be displaced against the electrical contact member 140 in contact with the retainer 152, which is inserted within an annular region of the annular member 138 to secure the electrical contact member 140 to the body 134.

The spring mechanism in an embodiment of the present disclosure allows the parts of the coupling device 130 to remain in secure engagement during use. It can also facilitate use during detachment of the parts for cleaning, maintenance or other suitable purpose.

As previously discussed, the present disclosure can be effectively utilized to detect dislodgment of an access device, such as a needle, inserted within a patient through which fluid can pass between the patient and a fluid delivery and/or treatment system. The present disclosure can be applied in a number of different applications, such as medical therapies or treatments, particularly dialysis therapies. In dialysis therapies, access devices, such as needles, are inserted into a patient's arteries and veins to connect blood flow to and from the dialysis machine.

Under these circumstances, if the needle becomes dislodged or separated from the blood circuit, particularly the venous needle, the amount of blood loss from the patient can be significant and immediate. The systems of the present disclosure can control and effectively minimize blood loss from a patient due to dislodgment of the access device, such as during dialysis therapy including hemodialysis, hemofiltration, hemodiafiltration and continuous renal replacement.

Signal Detection and Processing

As previously discussed, the electrical contacts in connection with the controller can be used to detect a change in impedance or the like in response to needle drop-out or other like changes in access conditions. In an embodiment, the present disclosure can be adapted to correct for any variations in the baseline impedance over time. This can increase the level of sensitivity with respect to the detection capabilities of the present disclosure. If changes in the baseline impedance are too great and not adequately corrected for, changes in impedance due to needle dislodgment may not be as readily, if at all, detectable above baseline values.

From a practical standpoint, there are a number of different process conditions that may influence a change in the baseline impedance over time. For example, a gradual drift or change in the baseline can occur due to a change in the characteristics, such as the hematocrit, plasma protein, blood/water conductivity and/or the like, of the blood or other suitable fluid during treatment. This can arise due to changes in the level of electrolytes or other components during dialysis therapy.

Figure 3:
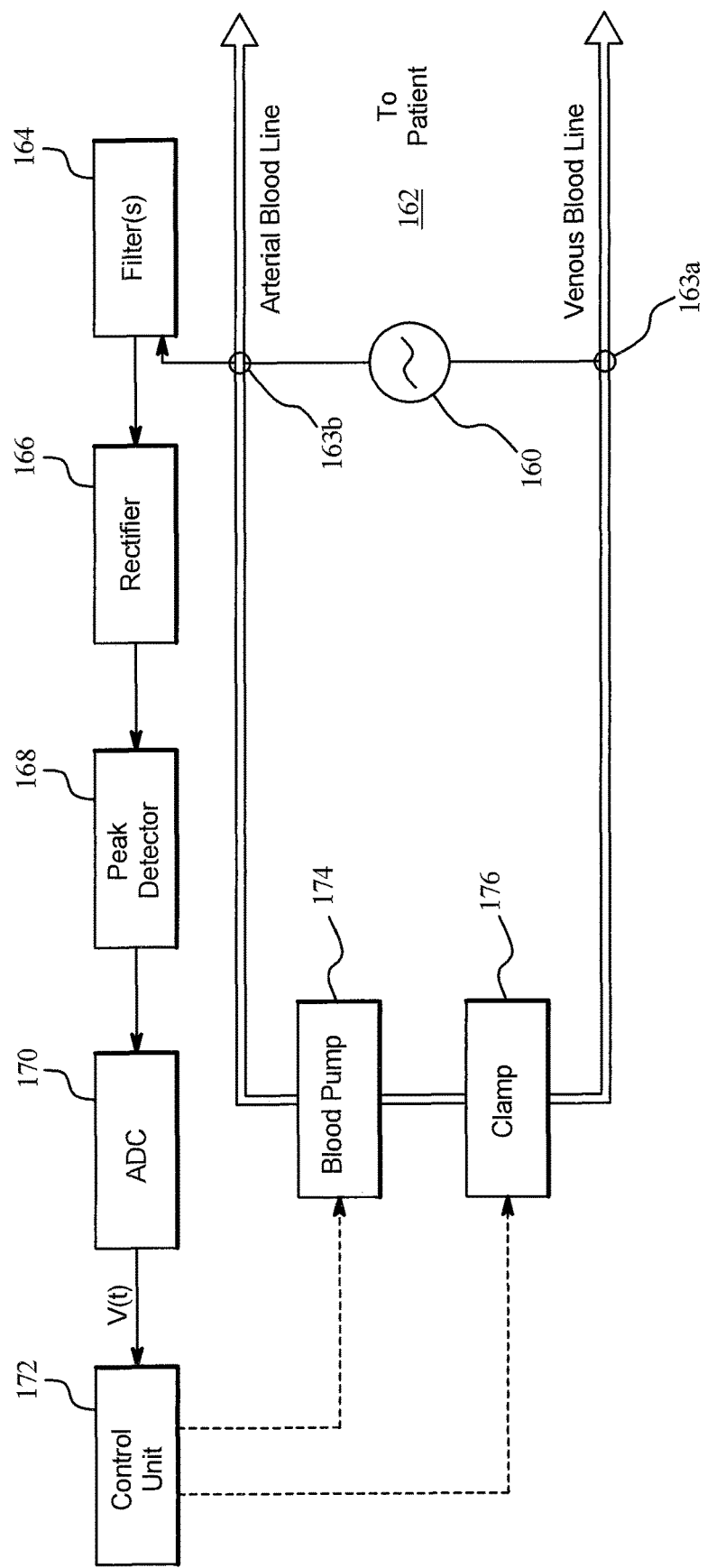
FIG. 3 schematically illustrates an embodiment of the present disclosure relating to processing of a measurable voltage signal to correct for changes in baseline impedance during treatment.

As illustrated in FIG. 3, the present disclosure can process a measurable voltage signal to correct for changes in baseline impedance over time. This can enhance the detection capabilities of the present disclosure as previously discussed. In an embodiment, a current source 160 or the like generates an electric current to pass through the blood as it circulates into, through and out of the patient along the extracorporeal blood circuit 162, which connects the patient via venous and arterial needles to the dialysis system including a variety of process components. The electric current is injected into the blood circuit via a first electrical contact 163a to define a conductor loop or pathway along the blood circuits. The current is maintained at a constant level until dislodgment occurs in one embodiment.

A second electrode 163b is used to sense voltage or the like along the conductor loop and then pass a signal indicative of same and/or changes thereof to an electronic device for detection and processing as previously discussed. The voltage signal can be measured and processed in any suitable manner.

In an embodiment, the signal is passed through a series of components including a filter or filters 164 which can act to filter noise from the signal, particularly noise derived from the rotation from the pump in order to minimize a false negative and/or positive detection of needle dislodgment, a rectifier 166, a peak detector 168 and an analog to digital converter ("ADC") 170 to digitize the signal. the digital signal can then be stored in a computer device (not shown) for further processing. The voltage signal is continually measured and processed over time. With each measurement, the digitized signals are compared to evaluate changes due to baseline changes associated with variations in process conditions over time, such as a change in the characteristics of blood as previously discussed. If a baseline change is determined, the digitized signal can be further processed to correct for the change in baseline.

The voltage data is continually sent to a control unit 172 coupled to the ADC. The control unit continually performs a calculation to determine whether a change in impedance or the like in response to needle dislodgment has occurred. In an embodiment, dislodgment of an access device is detected when $[V(t)-V(t-T)]>C1$, where t is time, where T is the period of blood pump revolution, where C1 is a constant and where $V(t)=I_o*Z$, where $I_o$ is current and where Z is the impedance of the bloodline which is a function of the impedance associated with patient's vascular access and the impedance associated with various components of the dialysis system, such as the dialyzer, as previously discussed.

If disconnection of the patient from the blood circuit is detected, the control unit 172 can be utilized to process the signal in order to minimize blood loss from the patient. In an embodiment, the controller is in communication with a dialysis system as applied to administer dialysis therapy including, for example, hemodialysis, hemofiltration, hemodiafiltration and continuous renal replacement. This communication can be either hard-wired (i.e., electrical communication cable), a wireless communication (i.e., wireless RF interface), a pneumatic interface or the like. The controller can process the signal to communicate with the dialysis system or device to shut off or stop the blood pump 174 associated with the hemodialysis machine and thus effectively minimize the amount of blood loss from the patient due to needle dislodgment during hemodialysis.

The controller can communicate with the dialysis system in a variety of other ways. For example, the controller and hemodialysis machine can communicate to activate a venous line clamp 176 for preventing further blood flow via the venous needle thus minimizing blood loss to the patient. In an embodiment, the venous line clamp is activated by the controller and attached to or positioned relative to the venous needle such that it can clamp off the venous line in close proximity to the needle. Once clamped, the dialysis system is capable of sensing an increase in pressure and can be programmed to shut-off the blood pump upon sensing pressure within the blood flow line which is above a predetermined level. Alternatively, the venous line clamp can be controllably attached to the dialysis system.

In an embodiment, an alarm can be activated upon detection of blood loss due to, for example, needle dislodgment during dialysis therapy. Once activated, the alarm (i.e., audio and/or visual or the like) is capable of alerting the patient, a medical care provider (i.e., doctor, registered nurse or the like) and/or a non-medical care provider (i.e., family member, friend or the like) of the blood loss due to, for example, needle dislodgment. The alarm function is particularly desirable during dialysis therapy in a non-medical facility, such as in a home setting or self care setting where dialysis therapy is typically administered by the patient and/or a non-medical care provider in a non-medical setting or environment excluding a hospital or other like medical facility.

The alarm activation, for example, prompts the patient to check that the blood pump has been automatically shut off, so that blood is minimized. Thus, the patient has the ability to act without the assistance of a third party (i.e., to act on his or her own) to ensure that responsive measures are taken to minimize blood loss. The alarm can thus function to ensure the patient's safety during the administration of dialysis therapy, particularly as applied to home hemodialysis treatments in which at least a portion of the dialysis therapy can be administered while the patient is sleeping.

Dialysis Machine

As previously discussed, the present disclosure can be adapted for use with any suitable fluid delivery system, treatment system or the like. In an embodiment, the present disclosure is adapted for use with a dialysis machine to detect access disconnection as blood flows between the patient and the dialysis machine along a blood circuit during treatment, including, for example hemodialysis, hemofiltration and hemodiafiltration.

Figure 4A:
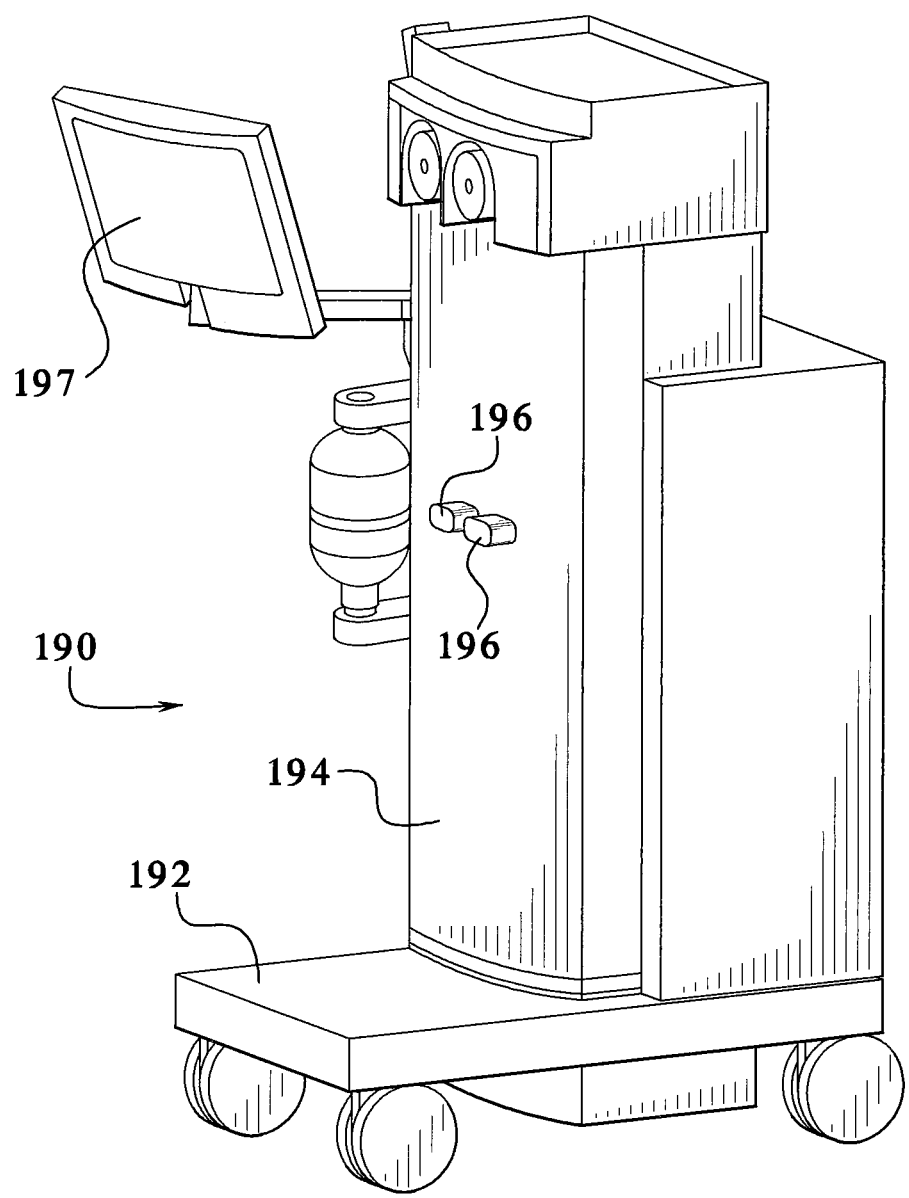
FIG. 4A schematically illustrates a hemodialysis machine in an embodiment of the present disclosure.
Figure 4B:
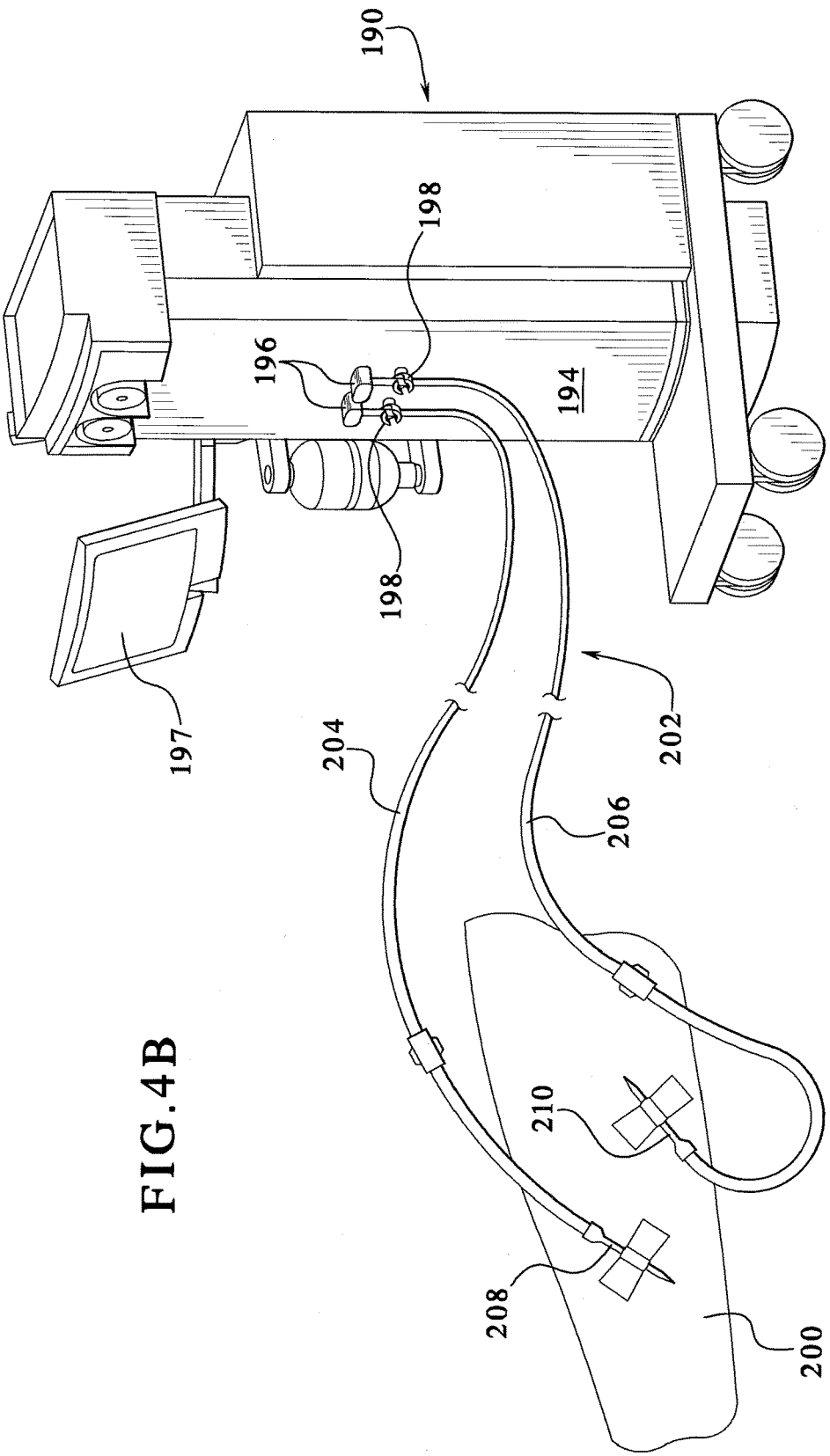
FIG. 4B schematically illustrates a hemodialysis machine coupled to a patient's access via a tubing set in an embodiment of the present disclosure.

The present disclosure can include any suitable dialysis machine for such purposes. An example, of a hemodialysis machine of the present disclosure is disclosed in U.S. Pat. No. 6,143,181 herein incorporated by reference. In an embodiment, the dialysis machine 190 comprises a mobile chassis 192 and it has at the front side 194 thereof with a common mechanism 196 for connecting tubing or the like by which a patient can be connected to the dialysis machine as shown in FIG. 4B. A flat touch screen 197, which can show several operational parameters and is provided with symbols and fields for adjustment of the dialysis machine. Touch screen 197 can be adjusted vertically and can be universally pivoted relative to chassis 192 of dialysis machine 190 and can be fixed in the desired adjusted position.

In an embodiment, dialysis machine 190 includes a chassis 192 having one or more connectors for connecting a patient to the dialysis machine via a blood circuit allowing blood to flow between the patient and the dialysis machine during dialysis therapy, wherein one or more electrical contact is connected to the blood circuit in fluid communication with the blood allowing detection of a change in an electrical value in response to access disconnection as the blood flows through the blood circuit having an electrical signal passing therein.

In an embodiment, dialysis machine 190 can be designed to accommodate one or more of the electrical contact coupling devices, such as a pair of coupling device, used to detect access disconnection as shown in FIG. 4B. For example, one or more coupling devices 198 can be attached to the front panel 194 of the dialysis machine 190. This can be done in any suitable way. In an embodiment, a stem portion of the coupling device is insertably mounted via a threaded fit, frictional fit or the like, as previously discussed. This connects the patient to the dialysis machine 190 via a blood tubing set 202. The blood tubing set includes a first blood line 204 and a second blood line 206. In an embodiment, the first blood line 204 is connected to the patient via an arterial needle 208 or the like through which blood can flow from the patient 200 to the dialysis machine 190. The second blood line 206 is then connected to the patient 200 via a venous needle 210 or the like through which fluid flows from the dialysis machine to the patient to define a blood circuit.

Alternatively, the first blood line and the second blood line can be coupled to the venous needle and the arterial needle, respectively. The blood lines are made from any suitable medical grade material. Access disconnection, such as dislodgment of an arterial needle and/or a venous needle can be detected as previously discussed. Alternatively, the coupling device can be attached to the blood tubing set which is then attached to the dialysis machine in any suitable way.

Dialysis Treatment Centers

As previously discussed, the present disclosure can be used during dialysis therapy conducted at home and in dialysis treatment centers. The dialysis treatment centers can provide dialysis therapy to a number of patients. The treatment centers include a number of dialysis machines to accommodate patient demands. The therapy sessions at dialysis treatment centers can be performed twenty-four hours a day, seven days a week depending on the locale and the patient demand for use.

In an embodiment, the dialysis treatment centers are provided with the capability to detect access disconnection during dialysis therapy pursuant to an embodiment of the present disclosure. For example, one or more of the dialysis machines can be adapted for use with an electrical contact coupling device along with the necessary other components to detect access disconnection as previously discussed.

In an embodiment, the electrical contact coupling device can be directly attached to one or more of the dialysis machines of the dialysis treatment center. It should be appreciated that the apparatuses, devices, methods and/or systems pursuant to an embodiment of the present disclosure can be applied for use during dialysis therapy administered to one or more patients in the dialysis treatment center in any suitable way. In an embodiment, the treatment center can have one or more patient stations at which dialysis therapy can be performed on one or more patients each coupled to a respective dialysis machine. Any suitable in-center therapy can be performed including, for example, hemodialysis, hemofiltration and hemodiafiltration and combinations thereof. As used herein, the term "patient station" or other like terms mean any suitably defined area of the dialysis treatment center dedicated for use during dialysis therapy. The patient station can include any number and type of suitable equipment necessary to administer dialysis therapy.

In an embodiment, the dialysis treatment center includes a number of patient stations each at which dialysis therapy can be administered to one or more patients; and one or more dialysis machines located at a respective patient station. One or more of the dialysis machines can include a chassis having one or more connectors for connecting a patient to the dialysis machine via a blood circuit allowing blood to flow between the patient and the dialysis machine during dialysis therapy wherein a pair of electrical contacts are connected to the blood circuit in fluid communication with the blood allowing detection of a change in an electrical value in response to access disconnection as the blood flows through the blood circuit having an electrical signal passing therein.

As previously discussed, the access disconnection detection capabilities of the present disclosure can be utilized to monitor and control a safe and effective dialysis therapy. Upon dislodgment of an access device, such as a needle, from the patient, the direct conductive measurement capabilities of the present disclosure can be used to provide a signal indicative of dislodgment that can be further processed for control and/or monitoring purposes. In an embodiment, the signal can be further processed to automatically terminate dialysis therapy to minimize blood loss due to dislodgment as previously discussed. Further, the signal can be processed to activate an alarm which can alert the patient and/or medical personnel to the dislodgment condition to ensure that responsive measures are taken. It should be appreciated that the present disclosure can be modified in a variety of suitable ways to facilitate the safe and effective administration of medical therapy, including dialysis therapy.

Applicants have found that the direct conductive measurement capabilities of the apparatus of the present disclosure can immediately detect blood loss or the like due to access disconnection, such as needle dislodgment, with high sensitivity and selectivity such that responsive measures can be taken to minimize blood loss due to same. The ability to act responsively and quickly to minimize blood loss upon detection thereof is particularly important with respect to needle dislodgment during hemodialysis. If not detected and responded to immediately, the amount of blood loss can be significant. In an embodiment, the present disclosure is capable of taking active or responsive measures, to minimize blood loss (i.e., shut-off blood pump, activate venous line clamp or the like) within about three seconds or less, e.g., within about two to about three seconds, upon immediate detection of needle dislodgment.

In addition, the controller can be utilized to monitor and/or control one or more treatment parameters during hemodialysis. These parameters can include, for example, the detection of blood due to blood loss upon needle dislodgment, the change in blood flow, the detection of air bubbles in the arterial line, detection of movement of the sensor during treatment, detection and/or monitoring of electrical continuity of the sensor or other like treatment parameters. In an embodiment, the controller includes a display (not shown) for monitoring one or more of the parameters.

As used herein "medical care provider" or other like terms including, for example, "medical care personnel", means an individual or individuals who are medically licensed, trained, experienced and/or otherwise qualified to practice and/or administer medical procedures including, for example, dialysis therapy, to a patient. Examples of a medical care provider include a doctor, a physician, a registered nurse or other like medical care personnel.

As used herein "non-medical care provider" or other like terms including, for example, "non-medical care personnel" means an individual or individuals who are not generally recognized as typical medical care providers, such as doctors, physicians, registered nurses or the like. Examples of non-medical care providers include patients, family members, friends or other like individuals.

As used herein "medical facility" or other like terms including, for example, "medical setting" means a facility or center where medical procedures or therapies, including dialysis therapies, are typically performed under the care of medical care personnel. Examples of medical facilities include hospitals, medical treatment facilities, such as dialysis treatment facilities, dialysis treatment centers, hemodialysis centers or the like.

As used herein "non-medical facility" or other like terms including, for example, "non-medical setting" means a facility, center, setting and/or environment that is not recognized as a typical medical facility, such as a hospital or the like. Examples of non-medical settings include a home, a residence or the like.

It should be appreciated that the electrode output signal can be combined with other less sensitive blood loss detection methods, such as venous pressure measurements, systemic blood pressure, the like or combinations thereof, to improve specificity to needle dislodgment.

Conductive Polymer

The present disclosure provides conductive polymer materials and devices, apparatuses, systems and methods that employ same. The conductive polymer material can be utilized in a number of different applications, such as to monitor patient therapy. For example, the conductive polymer materials can be utilized to monitor patient access conditions as discussed above and as further detailed below. Other types of monitoring applications include, for example, monitoring solution mixing or compounding as described in greater detail below. The present disclosure contemplates monitoring one or a combination of condition changes associated with patient therapy, such as monitoring patient access conditions and solution mixing conditions, alone or in combination.

In an embodiment, the conductive polymer material includes a polymer matrix and a conductive component that is incorporated in the polymer matrix. Alternatively, the conductive polymer material, in an embodiment, includes a conductive polymer component without a separate conductive component, such as stainless steel. It should be appreciated that the conductive polymer material can be made from any suitable types and amounts of materials and in any suitable way.

As discussed above, the conductive polymer can include a polymer matrix and a conductive component incorporated in the matrix. The polymer matrix can include a variety of different polymer-based materials that are suitable for use in a variety of applications, particularly including medical applications, such as dialysis therapy. In an embodiment, the polymer matrix includes polyvinyl chloride, acrylonitrile butadiene styrene, polycarbonate, acrylic, a cyclo olefin copolymer, a cyclo olefin copolymer blend, a metallocene-based polyethylene, like polymeric materials and suitable combinations thereof.

The conductive component can include any suitable material or combination of materials that have conductive properties applicable for a number of different applications including, for example, detecting patient access disconnection during medical therapy as previously discussed, monitoring the mixing or compounding of solution components to form a mixed solution, and/or other like applications. Preferably, the conductive component includes stainless steel, fillers, carbon black, fibers thereof and/or the like.

The conductive component can be sized and shaped in any suitable way such that it can be readily incorporated in the polymer matrix. For example, the conductive component can include conductive fibers made from any suitable material, such as stainless steel, a carbonaceous material and/or the like. The fibers, in an embodiment, have an aspect ratio that ranges from about 2:1 to about 30:1.

The conductive polymer material can include any suitable amount of the conductive polymer matrix and the conductive component. This can vary depending on the application of the conductive polymer material. In an embodiment, the conductive component includes greater than about 10% by weight of the conductive polymer material. Preferably, the conductive component ranges from about 10% to about 50% by weight of the conductive polymer material. It should be appreciated that more than about 50% by weight of the conductive component can be utilized but may provide minimal, if any, increase in performance of the conductive polymer material depending on the application. Preferably, the conductive component is uniformly dispersed throughout the polymer matrix.

As previously discussed, the conductive polymer material, in an embodiment, is composed of a conductive polymer component. This type of component has sufficient electrical conductivity properties such that an additional conductive component, such as stainless steel, is not required. Examples of conductive polymer material components include polyaniline, polypyrrole, polythiophenes, polyethylenedioxythiophene, poly(p-phenylene vinylene), the like and mixtures thereof.

As previously discussed, the conductive polymer material can be made in any suitable way. In general, the conductive component is mixed with the polymer component under suitable processing conditions including temperature and pressure, for example, to form a polymer matrix with the conductive component incorporated therein. The mixing should take place over a suitable period of time and with a sufficient amount of force such that the conductive component is uniformly distributed throughout the polymer matrix.

The polymer matrix incorporated with a conductive component is then shaped and formed into a final product in any suitable way. For example, the polymer matrix incorporated with the conductive component can be formed into a single piece part via an injection molding process, extrusion process or the like under suitable processing conditions. Thus, the conductive polymer material can be readily made with manufacturing techniques, such as injection molding and extrusion. This can effectively provide a cost savings to the manufacturing process that can be inevitably passed along to the consumer.

The conductive polymer material can be formed into any suitable shape and size depending on the application. In an embodiment, the conductive polymer material is formed into an electrode or other like electrical contact that can be utilized for a number of different applications, including, for example, monitoring patient access conditions and/or monitoring solution mixing or compounding as discussed above and described below in greater detail. The conductive polymer electrode can have a variety of different and suitable configurations depending on the application. For example, the conductive polymer electrode can be made into a coupler that can be used to join tubing to form a tubing joint as described below.

As shown in FIGS. 5A and 5B, the conductive polymer coupler has a generally cylindrical shape. With this configuration, the conductive polymer can be readily attached to a tube through which fluid flows, thus forming a tubing joint.

As shown in FIG. 5A, the coupler 220 has a member 222 that extends from an inner surface 224 of the coupler electrode 220. The member 222 acts as a stop for the tube 226 that is attached to the electrode such that a desired length of the tubing joint 228 can be preset. The coupler 220 as shown in FIG. 5A, in an embodiment, is made via an injection molding process.

As shown in FIG. 5A, a first tube member 230 is attached to a first end 232 of the coupler 220 and positioned or stopped by a first end 234 of the member 222. A second tube member 236 is attached to a second end 238 of the coupler 220 and stopped or positioned by a second end 240 of the member 222. This forms a tubing joint 228, such as a tubing joint that is integrated within a blood circuit and utilized during dialysis therapy as described in the present application.

As shown in FIG. 5B, the coupler 242 is formed without a member that allows the length of the tubing joint to be preset as discussed above. In this regard, the tubing joint length can be adjusted accordingly depending on the application. Further, the coupler 242 as shown in FIG. 5B can be made via an extrusion process instead of an injection molding process. This can provide a further cost savings with respect to manufacturing of the coupler as compared to an injection molding process as discussed above. As shown in FIG. 5B, a first tube member 244 is attached to a first end 246 of the coupler 242 and a second tube member 248 is attached to the second end 250 of the coupler 242, thus forming the tubing joint 252.

The tube member can be attached to the conductive polymer coupler in any suitable way. For example, the conductive polymer material can be solvent bonded, heat sealed, laser welded, radio frequency sealed, or the like to the tubing.

The tubing can be made of any suitable material depending on the application. For example, the tubing can be made from polyvinyl chloride ("PVC"). Preferably, the PVC tubing is attached to a conductive polymer material that is made with a polymer matrix composed of acrylonitrile butadiene styrene ("ABS") where the ABS-based conductive material is solvent bonded to the PVC tubing.

However, the tubing can be made of a variety of different materials depending on the application. In an embodiment, the tubing includes a non-PVC material, such as metallocene-based polyethylene polymers, cyclo olefin copolymers, cyclo olefin copolymer blends and the like. The non-PVC materials can include any suitable type and amount of constituents. Metallocene-based polyethylene polymers and the like illustrative of the present disclosure can be found, for example, in U.S. Pat. No. 6,372,848, the disclosure of which is herein incorporated by reference. These types of non-PVC polymers can include a polymer blend that has a first ethylene and α-olefin copolymer obtained using a single site catalyst present in an amount by weight of from about 0% to about 99% by weight of the blend and having a melt flow index from fractional, such as about 0.1 g/10 min to about 5 g/10 min, a second ethylene and α-olefin copolymer obtained using a single site catalyst and being present in an amount by weight of the blend from about 0% to about 99% and having a melt flow index from higher than about 5 g/10 min to about 20 g/10 min; and a third ethylene and α-olefin copolymer obtained using a single-site catalyst and being present in an amount by weight of the blend from about 0% to about 99% and having a melt flow index greater than about 20 g/10 min. In an embodiment, the α-olefin copolymer has a molecular weight distribution of less than about 3.

Cyclo olefin copolymers and blends thereof illustrative of the present disclosure can be found, for example, in U.S. Pat. No. 6,255,396, the disclosure of which is herein incorporated by reference. These types of non-PVC polymers can include as a component homopolymers or copolymers of cyclic olefins or bridged polycyclic hydrocarbons. For example, the polymer composition includes a first component obtained by copolymerizing a norbomene monomer and an ethylene monomer wherein the first component is in an amount from about 1-99% weight of the composition; and a second component of an ethylene and α-olefin copolymer that has six carbons wherein the second component is in an amount from about 99% to about 1% by weight of the composition. In an embodiment, the polymer composition can include an additional component, such as a second homopolymer or copolymer of a cyclic olefin or a bridged polycyclic hydrocarbon.

The non-PVC based tubing and the non-PVC based conductive coupler can be joined in any suitable way to form a tubing joint. In an embodiment, the non-PVC based tubing and coupler are joined via solvent bonding, such as disclosed in U.S. Pat. Nos. 6,255,396 and 6,372,848. As used herein the term solvent bonding or other like terms means that the tubing can be exposed to a solvent to melt, dissolve or swell the tubing and then be attached to another polymeric component to form a permanent bond. Suitable solvents typically include those having a solubility parameter of less than about 20 (Mpa)½. Suitable solvents can also have a molecular weight less than about 200 g/mole. The solvent can include, for example, aliphatic hydrocarbons, aromatic hydrocarbons, and mixtures thereof. As used herein, the terms aliphatic hydrocarbon and aromatic hydrocarbon are compounds containing only carbon and hydrogen atoms.

Suitable aliphatic hydrocarbons can include substituted and unsubstituted hexane, heptane, cyclohexane, cycloheptane, decalin and the like. Suitable aromatic hydrocarbons can include substituted and unsubstituted aromatic hydrocarbon solvents, such as xylene, tetralin, toluene, cumene and the like. Suitable hydrocarbon substituents can include aliphatic substituents that have from 1-12 carbons and include propyl, ethyl, butyl, hexyl, tertiary butyl, isobutyl, the like and combinations thereof.

Figure 6:
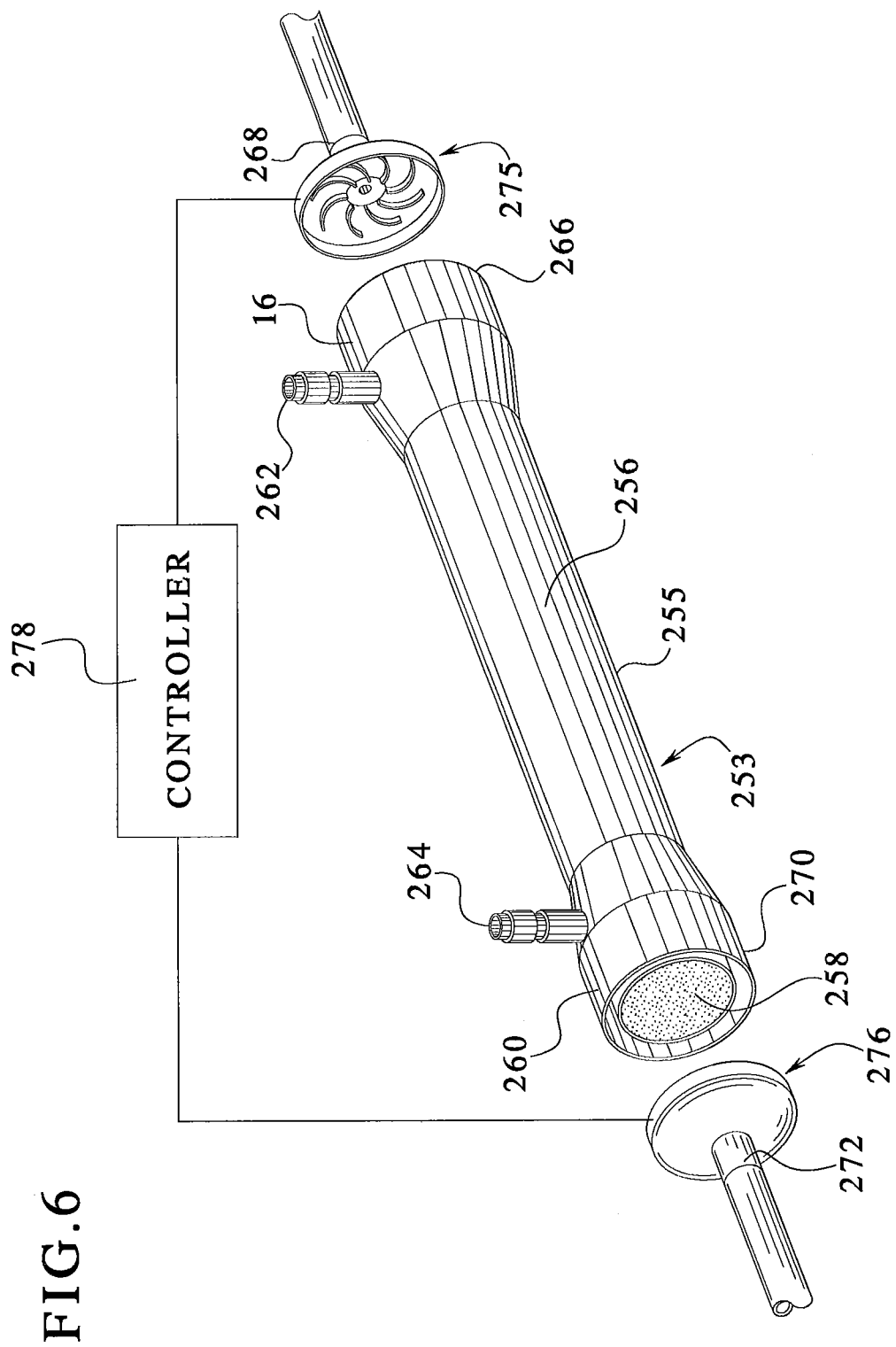
FIG. 6 illustrates a dialyzer according to an embodiment of the present disclosure.

As previously discussed, the conductive polymer of the present disclosure can be constructed and arranged into a variety of different configurations, such as a conductive polymer coupler as shown in FIGS. 5A and 5B and discussed above. Another example includes a dialyzer header that is made from the conductive polymer according to an embodiment. Referring to FIG. 6, a dialyzer 253 is generally illustrated. The dialyzer 253 includes a body member 255 that generally includes a casing 256. The casing 256 includes a core section as well as two bell members 260 located at each end of the dialyzer. Located within the core is a fiber bundle 258. The dialyzer also, includes a dialysate inlet 262 and a dialysate outlet 264.

Located at a first end 266 of the dialyzer 253 is a fluid inlet 268 and at a second end 270 is a fluid outlet 272 defined by a fluid inlet header 275 and a fluid outlet header 276, respectively. The dialyzer 253 is connected to a dialysis blood circuit in any suitable manner. In an embodiment, the inlet 275 and outlet 276 headers are made from the conductive polymer material of the present disclosure as discussed above. The inlet 275 and outlet 276 headers can be connected to a controller 278 such that the conductive polymer headers can be utilized to monitor patient access conditions as previously discussed.

A variety of different header and dialyzer designs can be utilized. For example, U.S. Pat. No. 6,623,638 and U.S. Patent Publication No. 2003/0075498 provide a number of different examples illustrative of the present disclosure. The disclosures of U.S. Pat. No. 6,623,638 and U.S. Patent Publication No. 2003/0075498 are herein incorporated by reference.

The conductive polymer of the present disclosure can be utilized in any suitable way and in a variety of different devices, apparatuses, systems and applications thereof. For example, the conductive polymer can be utilized to detect a change in impedance in response to dislodgement of an access device, to detect a change in conductivity in response to a change in solution composition and/or other suitable applications.

In an embodiment, the conductive polymer is part of a sensor assembly or apparatus that can be utilized, for example, for monitoring dialysis applications as discussed in the present application. The sensor apparatus of the present disclosure can include a number of different configurations and designs. Two examples of such designs illustrative of the present disclosure are described below in FIGS. 7A and 7B.

In FIG. 7A, the tubing joint 284 that includes the conductive polymer electrode 286 attached to a tube member 288 as described above, for example, is positioned in place by a holding device 290 or holder for purposes of detection capabilities associated with the sensor apparatus 291 in an embodiment. In general, the holder 290 as shown in FIG. 7A has a hub design. More specifically, the holder 290 includes a base member 292 onto which the tubing joint 284 can be placed. The base member 292 includes a first portion 294 that is made from a plastic or other suitable material. The first portion 294 defines an outer surface 296 of the base member 292. Along the outer surface 296, the first portion 294 includes two openings that are spaced apart as shown in FIG. 7A. The first opening 298 is located on a first edge 300 of the first portion of the base and the second opening 302 is located on a second edge 304 of the first portion of the base. The openings can be configured in any suitable way and be utilized for mounting purposes.

The second portion of the base member includes a conductive portion 306 as shown in FIG. 7A. In an embodiment, the conductive portion 306 includes a single piece part 308 that is made from any suitable conductive material, such as stainless steel and/or the like. As shown in FIG. 7A, the conductive polymer of the tubing joint is placed against a curved edge 310 of the second portion that substantially forms to an outer surface 312 of the conductive polymer electrode 286. The electrode is substantially cylindrical in shape.

The holder 290 further includes an arm member 314 that is pivotally attached to the base member 292 as shown in FIG. 7A. The arm member 314 includes a generally curved region such that the arm 314 can be positioned over the tubing joint 284 allowing it to substantially conform to the generally cylindrical surface of the tube joint and thus further securing the tubing joint 284 in place.

Another configuration of a hub design illustrative of the sensor apparatus of the present disclosure is shown in FIG. 7B. In general, this design provides a box-like holder 316 that encloses the tubing joint 318 wherein the tubing joint includes the conductive polymer electrode 320 in the form of a coupler that is attached to the tube member 322 as discussed above. The holder 316 includes a base member 324. The base member 324 includes side portions 326, a bottom portion 328 and an opening 330 at a top portion 332. As shown in FIG. 7B, the sensor apparatus 334 includes a conductive member 336 that is contained in the base member 324. The conductive member 336 can be made of any suitable material as described above. The conductive member 336 includes an annular-shaped surface 338 against which the tubing joint 318 can be placed. The sensor apparatus 334 further includes a lid 340 that is pivotally attached to the base member 324. The lid 340 has a member 342 that abuts against a portion of the tubing joint in a closed position. This secures the tubing joint in place for use.

As previously discussed, the sensor apparatus of the present application can be used in a number of suitable applications. For example, the sensor apparatus can be suitably coupled to a blood circuit and used for purposes of detecting disconnection of an access device as described in the present application. Another application includes the monitoring of solution compounding as described in greater detail below. In this regard, the sensor apparatus as shown in FIGS. 7A and 7B can be used in combination with or in place of the electrical coupling devices as illustrated in FIGS. 2A-2E and further described above. Thus, the present disclosure can be utilized to monitor one or a combination of conditions, such as patient access and solution mixing, during use. As applied, the sensor apparatus can be connected to a controller or other like device for detection purposes. The controller can include one or a number of different devices that are in electrical contact with the sensor apparatus in any suitable way.

In another embodiment, the sensor apparatus can include a single piece part that is made from the conductive polymer material. The single piece part can be made in any suitable way such as through injection molding as described above. A number of different and suitable shapes and sizes can be formed. One such example illustrative of the present disclosure of a single piece part conductive electrode 344 is shown in FIGS. 8A and 8B.

Figure 8A:
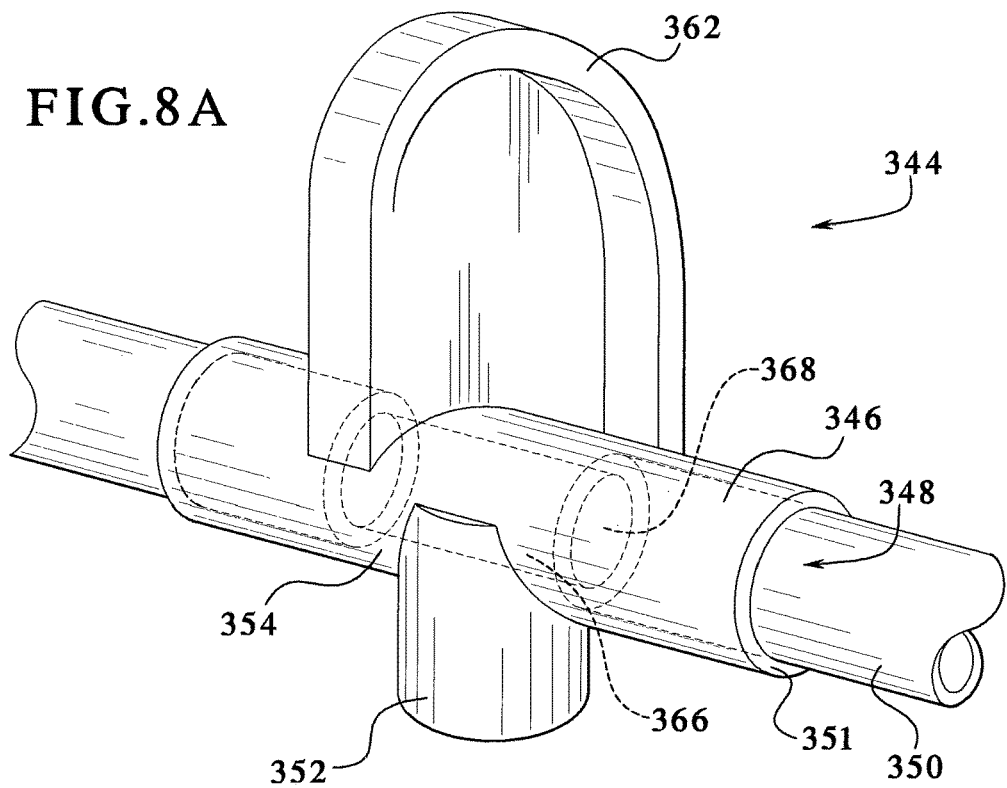
FIGS. 8A and 8B illustrate a single-piece sensor according to an embodiment of the present disclosure.
Figure 8B:
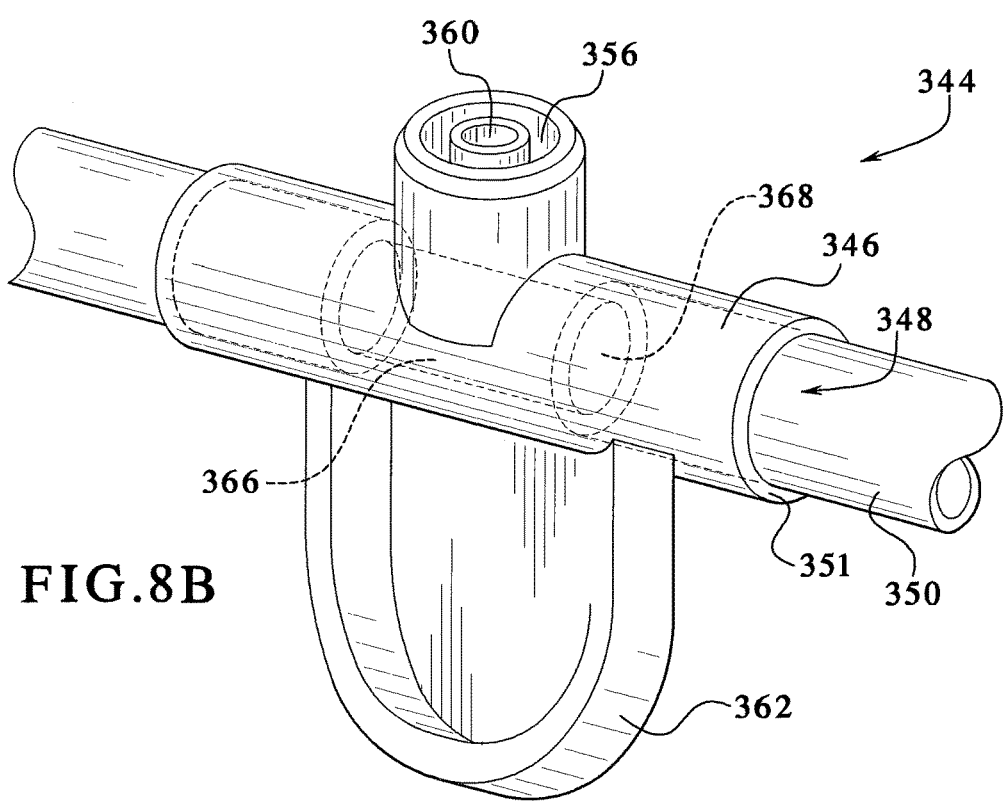

In general, the conductive polymer electrode 344 is configured as a coupler that can join tubing to form a tubing joint through which fluid can flow as shown in FIGS. 8A and 8B. The conductive polymer electrode 344 includes a base member 346 that has an annular opening 348 extending therethrough. A tube member 350 can be attached to the ends 351 of the annular opening 348 such that the tubing joint can be formed as described above. The base member 346 includes a stem portion 352 that extends from a portion of a surface 354 of the base member 346. This can be used to mount or attach the conductive polymer electrode 344 to a control panel or other suitable component, such as a hemodialysis machine as described above. The stem portion 352 defines an annular-shaped channel 356 that ends from the surface 354 of the base member 346. Within the annular-shaped channels, an inner annular-shaped channel 360 is also provided that extends from the surface 354 of the base 346, as shown in FIG. 8B. The stem portion can be utilized to provide a pathway through which the electrode can be in electrical contact with one or more other devices, such as a controller, in any suitable way. The base member further includes a top member 362 that extends from a portion of the surface 354 of the base member 346. The top member 362 can be used to secure the stem portion 352 of the base member 346 in place for use and/or to remove the electrode after use.

As shown in FIGS. 8A and 8B, the conductive polymer electrode 344 includes a member 366 that extends from an inner surface of the annular opening 348. The member 366 acts as a stop against which the tubing can be placed to form the tubing joint. The member 366 has a generally-cylindrical shape with an opening 368 through which fluid can flow.

As previously discussed, the conductive polymer material of the present disclosure can be utilized in a number of different applications. In an embodiment, the conductive polymer material can be utilized to monitor patient access conditions, such as to detect disconnection of an access device that is inserted in a patient through which fluid flows during medical therapy. Preferably, the disconnection detection application is applied during dialysis therapy, such as during hemodialysis therapy.

As applied to dialysis applications, the conductive polymer can be formed into an electrode and attached to a dialysis blood circuit in any suitable manner. As shown in FIGS. 1A and 2A and further described above, at least one of the sensors can include an electrode made with the conductive polymer material of the present disclosure. The sensors 22 and 24 are in electrical contact with a controller 29 and thus the conductive polymer electrode can be utilized for detection, monitoring and control purposes related to dialysis therapy as described above. As shown in FIGS. 4A and 4B and described in the present application, the sensors 198 can be attached directly to the hemodialysis machine wherein at least one of the sensors includes a conductive polymer electrode according to an embodiment of the present disclosure. The conductive polymer sensor can be configured in any suitable way, such as the coupler and hub design (See, FIGS. 5A, 5B, 7A and 7B), the single-piece part design (See, FIGS. 8A and 8B) and dialyzer header design (See, FIGS. 8A and 8B) as described above. It should be appreciated that the present disclosure contemplates the use of one or a combination of different sensors to monitor medical therapy, such as patient access and solution mixing conditions.

In an embodiment, the conductive polymer material of the present disclosure can be utilized for monitoring the mixing of solutions to form a mixed solution, such as a mixed solution used during medical therapy. One type of application illustrative of the present disclosure for such monitoring purposes is during dialysis therapy, particularly during peritoneal dialysis. In general, the conductive polymer material can be formed into an electrode or other sensing device that can effectively detect changes in conductivity associated with a dialysis solution that is administered to the patient during peritoneal dialysis.

The dialysis solution can be formed from a number of solution components that are mixed to form a mixed dialysis solution prior to administration. The dialysis solution components can have varying pH levels, such as ranging from about 1.8 to about 9.2. Once mixed, the pH of the mixed dialysis solution should be at a physiologically acceptable level, such as ranging from about 6.8 to about 7.5, prior to use. The pH level can be monitored in relation to changes in the conductivity level of the dialysis solution. In this regard, the conductive polymer of the present disclosure can be utilized to detect changes in conductivity level and thus can be utilized to determine whether the solution components are properly mixed to form the mixed dialysis solution at an acceptable pH level prior to use. A general description of peritoneal dialysis is provided below and is illustrative of the present disclosure.

Peritoneal dialysis utilizes a sterile dialysis solution, which is infused into a patient's peritoneal cavity and into contact with the patient's peritoneal membrane. Waste, toxins and excess water pass from the patient's bloodstream through the peritoneal membrane and into the dialysis solution. The transfer of waste, toxins, and excess water from the bloodstream into the dialysis solution occurs due to diffusion and osmosis during a dwell period as an osmotic agent in the dialysis solution creates an osmotic gradient across the membrane. The spent solution is later drained from the patient's peritoneal cavity to remove the waste, toxins and excess water from the patient.

There are various types of peritoneal dialysis therapies, including continuous ambulatory peritoneal dialysis ("CAPD") and automated peritoneal dialysis. CAPD is a manual dialysis treatment, in which the patient connects the catheter to a bag of fresh dialysis solution and manually infuses fresh dialysis solution through the catheter or other suitable access device and into the patient's peritoneal cavity. The patient disconnects the catheter from the fresh dialysis solution bag and allows the solution to dwell within the cavity to transfer waste, toxins and excess water from the patient's bloodstream to the dialysis solution. After a dwell period, the patient drains the spent dialysis solution and then repeats the manual dialysis procedure. Tubing sets with "Y" connectors for the solution and drain bags are available that can reduce the number of connections the patient must make. The tubing sets can include pre-attached bags including, for example, an empty bag and a bag filled with dialysis solution.

In CAPD, the patient performs several drain, fill, and dwell cycles during the day, for example, about four times per day. Each treatment cycle, which includes a drain, fill and dwell, takes about four hours.

Automated peritoneal dialysis is similar to continuous ambulatory peritoneal dialysis in that the dialysis treatment includes a drain, fill, and dwell cycle. However, a dialysis machine automatically performs three or more cycles of peritoneal dialysis treatment, typically overnight while the patient sleeps.

With automated peritoneal dialysis, an automated dialysis machine fluidly connects to an implanted catheter. The automated dialysis machine also fluidly connects to a source or bag of fresh dialysis solution and to a fluid drain. The dialysis machine pumps spent dialysis solution from the peritoneal cavity, through the catheter, to the drain. The dialysis machine then pumps fresh dialysis solution from the source, through the catheter, and into the patient's peritoneal cavity. The automated machine allows the dialysis solution to dwell within the cavity so that the transfer of waste, toxins and excess water from the patient's bloodstream to the dialysis solution can take place. A computer controls the automated dialysis machine so that the dialysis treatment occurs automatically when the patient is connected to the dialysis machine, for example, when the patient sleeps. That is, the dialysis system automatically and sequentially pumps fluid into the peritoneal cavity, allows for dwell, pumps fluid out of the peritoneal cavity, and repeats the procedure.

Several drain, fill, and dwell cycles will occur during the treatment. Also, a final volume "last fill" is typically used at the end of the automated dialysis treatment, which remains in the peritoneal cavity of the patient when the patient disconnects from the dialysis machine for the day. Automated peritoneal dialysis frees the patient from having to manually perform the drain, dwell, and fill steps during the day.

In general, the dialysis solution includes an osmotic agent, such as dextrose or other suitable constituent in any suitable amount, such as from about 1.5% to about 4.25% by weight. The dialysis solution further includes one or more electrolytes, such as sodium, calcium, potassium, magnesium chloride and/or the like in any suitable amount. The dialysis solution may also include other constituents, such as buffers including lactate and bicarbonate, or the like, and other constituents, such as stabilizers. The dialysis solution can be made from multiple solution components that can vary in the amounts and types of constituents thereof and have varying pH levels.

A variety of different and suitable types of multi-part dialysis solutions can be utilized. For example, a multi-part bicarbonate-based solution can be found in U.S. patent application Ser. No. 09/955,248, entitled "Biochemically Balanced Peritoneal Dialysis Solutions", filed on Sep. 17, 2001, the disclosure of which is incorporated herein by reference. An example of a multi-part lactate-based solution can be found in U.S. patent application Ser. No. 10/628,065, entitled "Dialysis Solutions With Reduced Levels Of Glucose Degradation Products", filed on Jul. 25, 2003 the disclosure of which is herein incorporated by reference.

Another example of a bicarbonate-based solution can be found in U.S. patent application Ser. No. 10/044,234, entitled "Bicarbonate-Based Solutions For Dialysis Therapies", filed on Jan. 11, 2002 and as further disclosed in U.S. Pat. No. 6,309,673, the disclosures of which are herein incorporated by reference. The bicarbonate-based solution can be made from solution components that have varying pH conditions, such as under moderate and extreme pH conditions. In an embodiment, the solution components can vary in pH from between about 1.0 to about 10.0. Once mixed, the desired pH of the mixed solution is a physiological acceptable level, such as between about 6.5 to about 7.6 (i.e., close to the pH of blood).

For example, under moderate pH conditions, the bicarbonate-based solution can be formulated by the mixing of a bicarbonate concentrate with a pH that ranges from about 7.2 to about 7.9, preferably from about 7.4 to about 7.6, and an electrolyte concentrate with a pH that ranges from about 3.0 to about 5.0. Under extreme pH conditions, for example, the bicarbonate concentrate has a pH that can range from about 8.6 to about 9.5 and is mixed with an electrolyte concentrate that has a pH from about 1.7 to about 2.2. A variety of different and suitable acidic and/or basic agents can be utilized to adjust the pH of the bicarbonate and/or electrolyte concentrates. For example, a variety of inorganic acids and bases can be utilized, such as hydrochloric acid, sulfuric acid, nitric acid, hydrogen bromide, hydrogen iodide, sodium hydroxide, the like or combinations thereof.

The solution components, such as the electrolyte concentrate and the dextrose concentrate, can then be mixed in the solution bag and then administered as a mixed solution to the patient during peritoneal dialysis. An illustrated example of a multi-chamber container that separately contains solution components of a dialysis solution according to embodiment of the present disclosure is shown in FIG. 9.

It should be appreciated that the components of the dialysis solutions of the present disclosure can be housed or contained in any suitable manner such that the dialysis solutions can be effectively prepared and administered. In an embodiment, the present disclosure includes a multi-part dialysis solution in which two or more parts are formulated and stored separately, and then mixed just prior to use. A variety of containers can be used to house the various parts of the dialysis solution, such as separate containers (i.e., flasks or bags) that are connected by a suitable fluid communication mechanism.

In an embodiment, a multi-chamber container or bag can be used to house the separate components of the solution including, for example, a dextrose concentrate and a buffer concentrate. In an embodiment, the separate components are mixed within the multi-chamber bag prior to use, such as applied during peritoneal dialysis.

Figure 9:
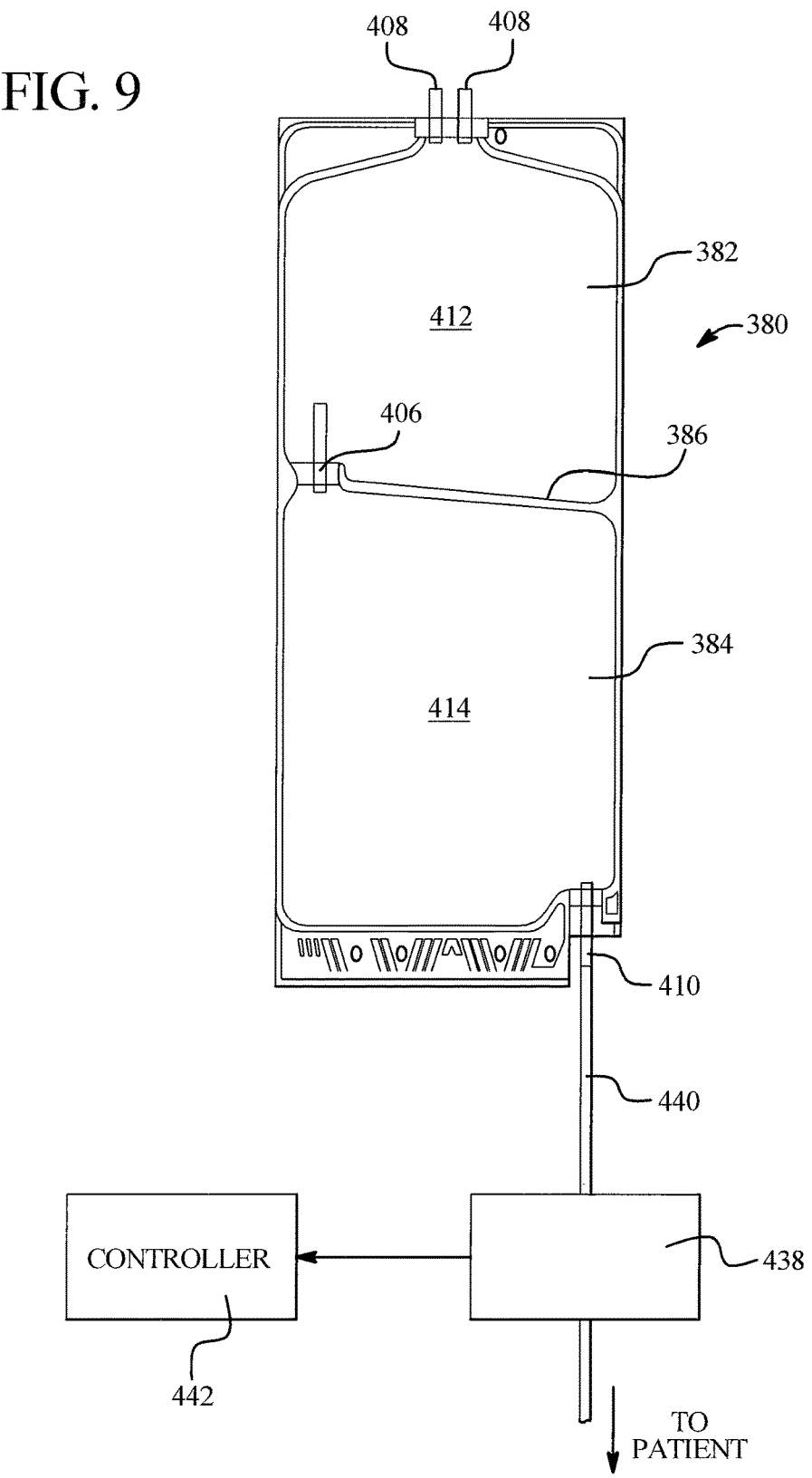
FIG. 9 illustrates a multi-chamber bag according to an embodiment of the present disclosure.

FIG. 9 illustrates a suitable container for storing, formulating, mixing and administering a dialysis solution, such as during continuous ambulatory peritoneal dialysis, according to an embodiment of the present disclosure. The multi-chamber bag 380 has a first chamber 382 and a second chamber 384. The interior of the container is divided by a heat seal 386 into the two chambers. It should be appreciated that the container can be divided into separate chambers by any suitable seal.

Figure 10:
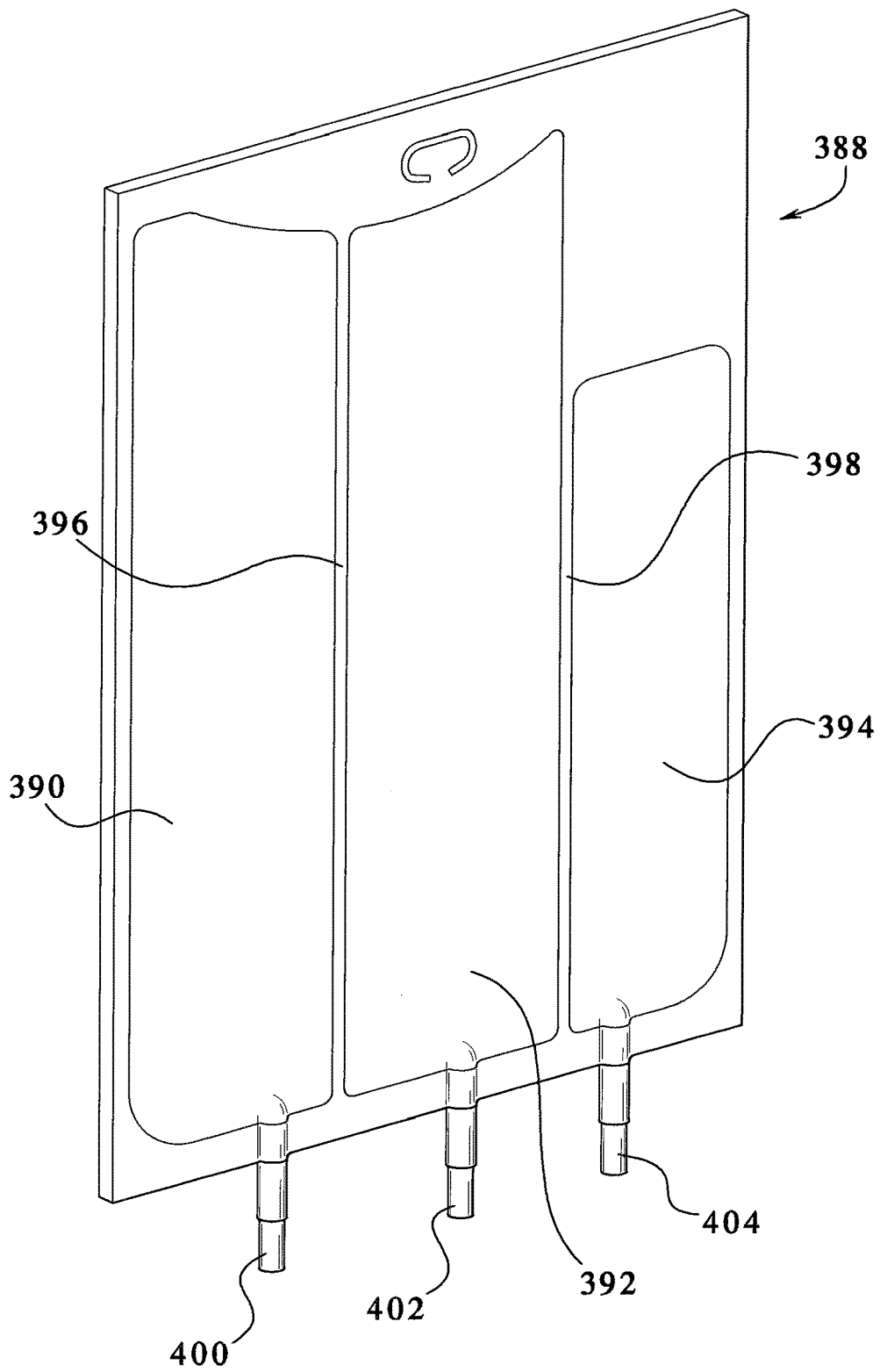
FIG. 10 illustrates a multi-chamber bag with a peelable seal according to an embodiment of the present disclosure.

In an embodiment, the container can be divided into separate chambers, such as two or more chambers, by a peel seal. With the use of a peel seal, a frangible connector or other suitable type of connector would not be required to mix the solution components within the multi-chamber bag. An example of a multi-chamber solution bag that includes a peel seal is disclosed in U.S. Pat. No. 6,319,243, the disclosure of which is herein incorporated by reference. As shown in FIG. 10, a container 388 includes at least three chambers 390, 392 and 394. The chambers 390, 392 and 394 are designed for the separate storage of liquids and/or solutions, that can be mixed within the container to form a mixed solution ready-for-use. It should be appreciated that more or less than three chambers can be utilized.

The peelable seals 396 and 398 are provided between the chambers 390, 392 and 394, respectively. Examples of peelable seals can be found in U.S. patent application Ser. No. 08/033,233 filed on Mar. 16, 1993 entitled "Peelable Seal And Container Having Same", the disclosure of which is herein incorporated by reference. The peelable seals allow for the selective opening of the chambers to allow for the selective mixing of the liquids contained therein.

The container 388 can also include tubular ports, such as tubular ports 400, 402 and 404 as shown in FIG. 10. The tubular ports are mounted to the container so as to allow fluid communication with the container and specifically with chambers 390, 392 and 394. To this end, the tubular ports 400, 402 and 404 can include a membrane that is pierced, for example, by a cannula or a spike or an administration set for delivery of the contents of the container to the patient. It should be appreciated that more or less than three ports can be utilized.

As shown in FIG. 9, the multi-chamber container 380 has a frangible connector 406 to sealingly couple the first chamber 382 to the second chamber 384 instead of a peelable seal. To mix the solution within the multi-chamber bag 380, the frangible connector 406 is broken.

The first container or chamber 382 includes two port tubes 408 of suitable sizes and lengths. It should be appreciated that more or less than two port tubes may be used. One of the port tubes, for example, can be utilized to add other constituents to the first chamber 382 during formulation of the solution of the present disclosure, if necessary. The remaining port tube, for example, can be utilized to adaptedly couple the first chamber 382 to the patient via a patient's administration line (not shown), be used to add additional other constituents or the like. The second container or chamber 384 has a single port tube 410 extending there from. In an embodiment, the port tube 410 is connected to a patient's administration line through which a solution can flow to the patient once the solution is mixed as described below.

In an embodiment, the transfer of product within the multi-chamber bag 380 can be initiated from the first chamber 382 to the second chamber 384 such that the components of each chamber can be properly mixed to form the dialysis solution of the present disclosure. In an embodiment, a dextrose concentrate 412 is contained in the first chamber 382 and a buffer concentrate 414 is contained in the second chamber 384. It should be appreciated that any suitable type or number of solution components can be separated with a multi-chamber bag and then mixed to form a mixed solution prior to administration to the patient. Illustrative examples of peritoneal dialysis solutions include those described in U.S. patent application Ser. Nos. 09/955,298 and 10/628,065 and U.S. Pat. No. 6,309,673 as described above.

The first chamber 382 is smaller in volume than the second chamber 384 such that the components of each chamber can be properly mixed once the transfer from the first chamber to the second chamber has occurred. Thus, the multi-chamber bag 380 can house at least two solution component parts that after mixture will result in a ready-to-use dialysis solution. An example of the multi-chamber container is set forth in U.S. Pat. No. 5,431,496, the disclosure of which is incorporated herein by reference. The multi-chamber bag can be made from a gas permeable material, such as polypropylene, polyvinyl chloride or the like.

It should be appreciated that the multi-chamber bag can be manufactured from a variety of different and suitable materials and configured in a number of suitable ways such that the dialysis solutions of the present disclosure can be effectively formulated and administered to the patient during medical therapy in any suitable manner. For example, the first chamber can be larger in volume than the second chamber and further adapted such that the dialysis solution of the present disclosure can be readily and effectively made and administered to the patient.

In an embodiment, the dialysis solution is contained and administered from a multi-chamber solution bag during peritoneal dialysis, such as during CAPD. The solution bag can include multiple chambers that each contain separate components of the dialysis solution prior to mixing as discussed above. This may be necessary to maintain separation of the non-compatible solution components prior to mixing for purposes of stability, sterility, effectiveness or the like associated with the dialysis solution prior to use.

Figure 11:
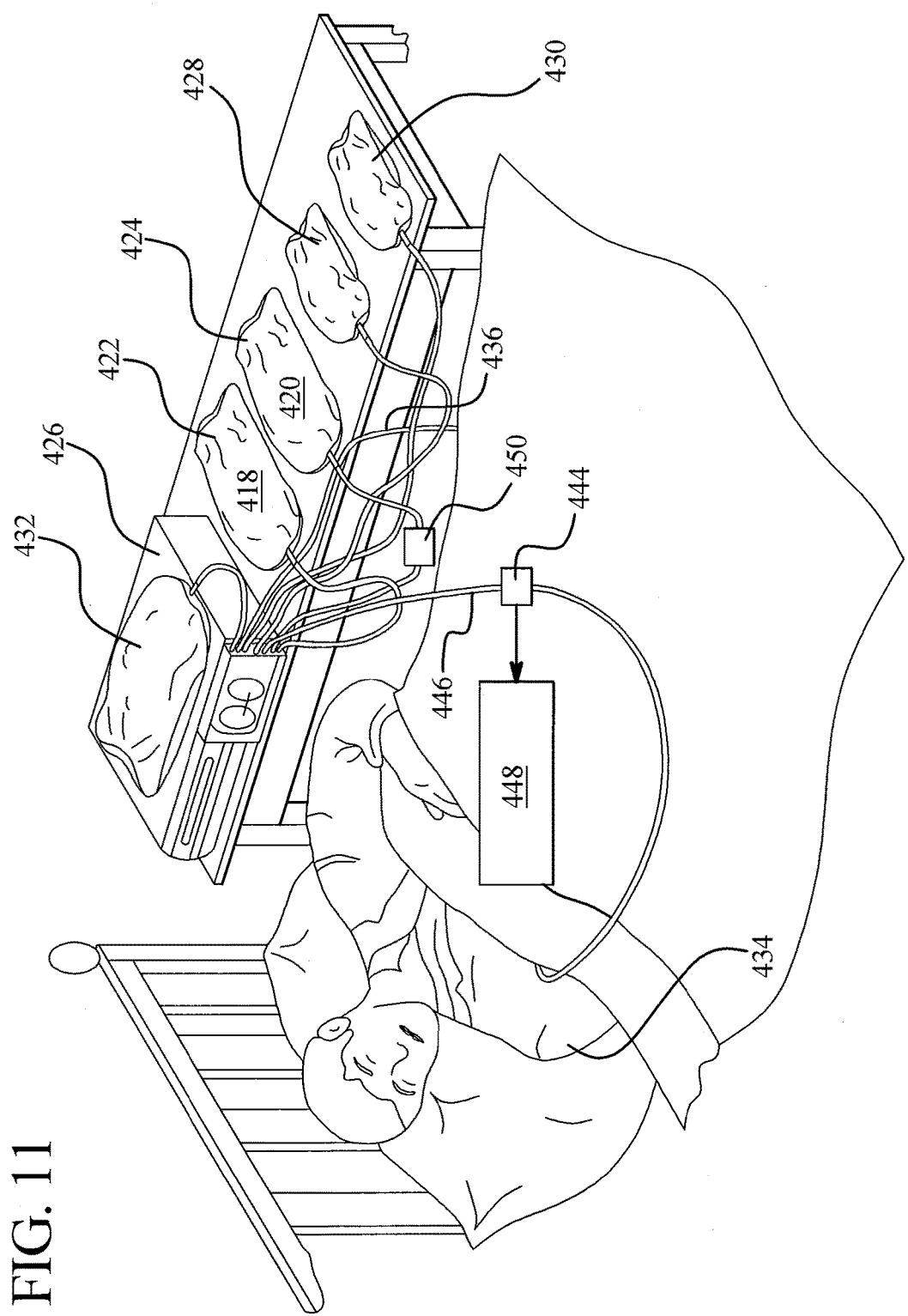
FIG. 11 illustrates an automated peritoneal dialysis system according to an embodiment of the present disclosure.

In another embodiment, the solution components can be prepared and stored in separate containers and then mixed via an admix device prior to use, such as applied during automated peritoneal dialysis. As shown in FIG. 11, a first solution component, such as a dextrose concentrate 416 and a second solution component, such as a buffer concentrate 420 are stored in the respective separate containers 422 and 424 or bags which are fluidly connected to an admix device 426 suitable for use during automated peritoneal dialysis. In addition to the first and second components, a first bag 428 and last bag 430 filled with a suitable solution can also be used during dialysis therapy as generally known.

In an embodiment, an effective amount of the first solution component 416 and the second solution component 420 are drawn from each respective container and into a heater bag 432 where the solution components (e.g., dextrose and buffer concentrates) can be mixed and heated prior to infusion into a patient 434 during dialysis therapy. As further shown in FIG. 11, a drain line 436 is coupled to the admix device 426 from which waste fluids can be removed from the patient during therapy.

According to an embodiment of the present disclosure, the conductive polymer material can be used as a sensor to monitor solution compounding, such as during peritoneal dialysis. For example, the conductive polymer sensor 438 can be attached to a tube 440 through which the mixed dialysis solution flows to the patient from the multi-chamber solution bag 380 as shown in FIG. 9. The conductive polymer sensor 438 is in electric contact with a controller 442 or other like device such that a change in conductivity of the mixed dialysis solution that is fed to the patient can be monitored. Based on the conductivity level, one can monitor the pH level of the mixed solution to determine whether the solution components (e.g., dextrose concentrate and buffer concentrate) have been properly and sufficiently mixed to form the dialysis solution prior to use. If the dialysis solution is not properly mixed, the conductivity level will exist above or below a baseline conductivity level that is generally associated with a desired pH level of a dialysis solution that is ready-for-use. As previously discussed, the desired pH of the mixed dialysis solution is maintained at a physiological acceptable level, such as between about 6.5 to about 7.6 prior to use. Based on this information, adjustments can be made to the process such that the solution chemistry of the dialysis solution is modified for proper use. This can facilitate the safe and effective use of the solution during use, such as during dialysis therapy.

As shown in FIG. 11, the conductive polymer sensor 444 of the present disclosure can be applied during automated peritoneal dialysis. More specifically, the conductive polymer sensor 444 of the present disclosure can be attached to the tube member 446 through which a dialysis solution flows to the patient. The dialysis solution is a product of the mixing of solution components that are stored in separate solution bags as previously discussed. The conductive polymer sensor 444 can be attached to a controller 448 or other like device in electrical contact such that the conductivity level and thus the pH level of the solution that is administered to the patient can be monitored as previously discussed. Optionally, at least one additional conductive polymer sensor 450 in an embodiment can also be utilized as shown in FIG. 11. In this regard, the additional sensor(s) can be utilized to monitor the conductivity level of the solution components prior to mixing. This can be utilized to evaluate whether the solution components are maintained at desired pH levels based on a conductivity measurement as discussed above.

Stand Alone Disconnection System and Method

Figure 12:
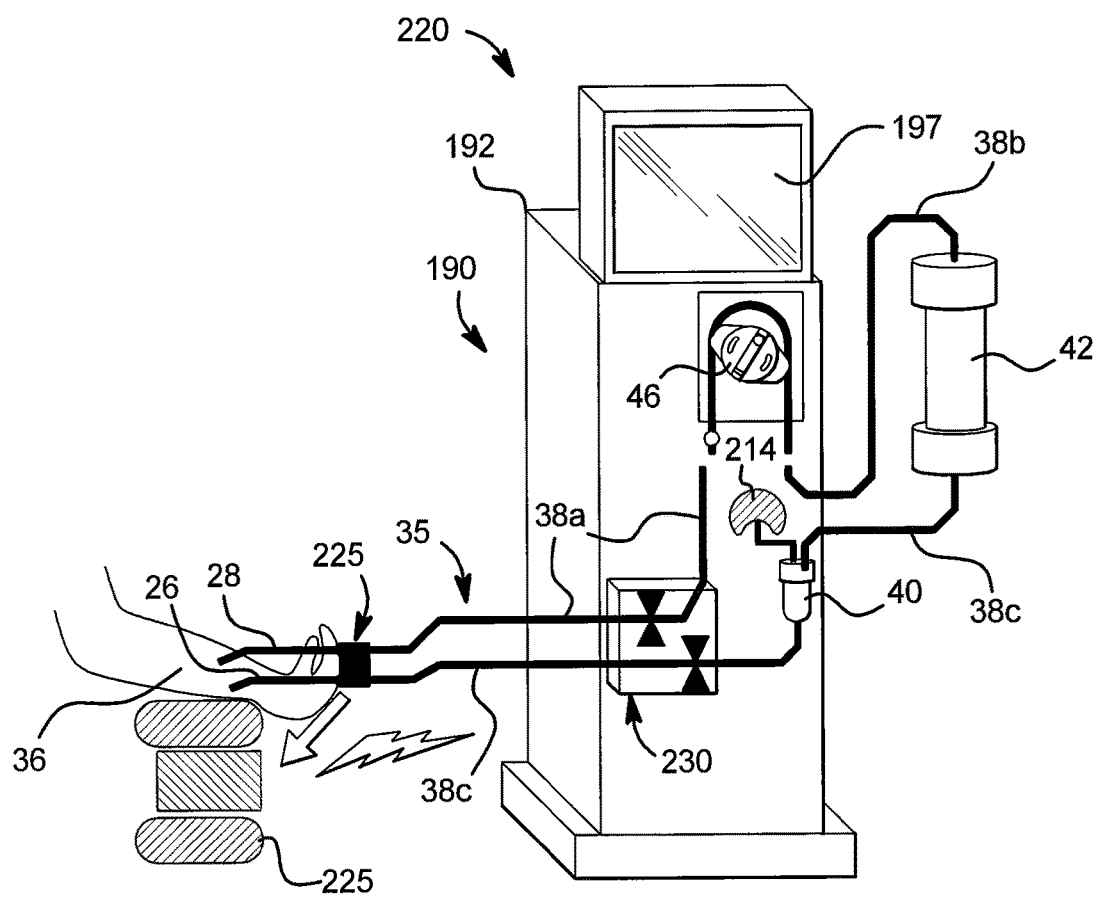
FIG. 12 is an isometric view of one embodiment of an access disconnection system employing the access disconnection methods herein, which can be retrofitted readily to an existing blood treatment machine.

Referring now to FIG. 12, an embodiment of a stand-alone access disconnection system 220 is illustrated. System 220 includes a dialysis machine 190, such as the one described above in connection with FIGS. 4A and 4B. For example, machine 190 includes a chassis 192 and a touch screen 197. Machine 190 includes a blood circuit 35 having a venous line 26 and an arterial line 28 connecting to venous needle 32 and arterial needle 34, respectively, forming patient access 36. Arterial line 28 extends from patient access 36 to a detector module 225, which is shown in more detail below in connection with FIG. 13. In general, detector module 225 includes electrodes that communicate electrically with contacts 22 and 24 (FIG. 1A) provided with venous and arterial lines 26 and 28, respectively. Alternatively, detector module 225 includes venous and arterial contact producing coupling devices 48 and 50, respectively, referenced above in connection with FIG. 1B, which contact blood directly, obviating the need for contacts 22 and 24 on the blood set. Detector module 225 also includes electronics capable of detecting an access disconnection and sending a remote or wireless signal to a protector module 230 described in more detail below in connection with FIG. 14.

A first tubing segment 38*a* of blood circuit 35 extends from detector module 225 to blood pump 46. A second tube segment 38*b* extends from segment 38*a* at blood pump 46 to dialyzer 42. A third tube segment 38*c* extends from dialyzer 42 to detector module 225. Venous line 26 extends from detector module 225 to patient access 36. As illustrated, detector module 225 is positioned to clamp one or more of tube segment 38*a* or 38*c* upon a sensing of a disconnection at patient access 36 by detector module 225. Venous drip chamber 40 is shown operating with tube segment 38*c*. Although not illustrated, an arterial drip chamber 44 can be placed additionally in tube segment 38*a*. Venous drip chamber 40 is shown operating with a pressure sensor 214.

It is expressly contemplated to provide system 220 including detector module 225 and protector module 230 as either an integrated part of machine 190, an option in ordering machine 190, or as a retrofit kit to an existing dialysis machine (or any other type of blood treatment or medical delivery machine described herein). Thus, in one embodiment, the electronics associated with detector module 225 and protector module 230 are independent from (except perhaps input power) the electronics of machine 190.

Figure 13:
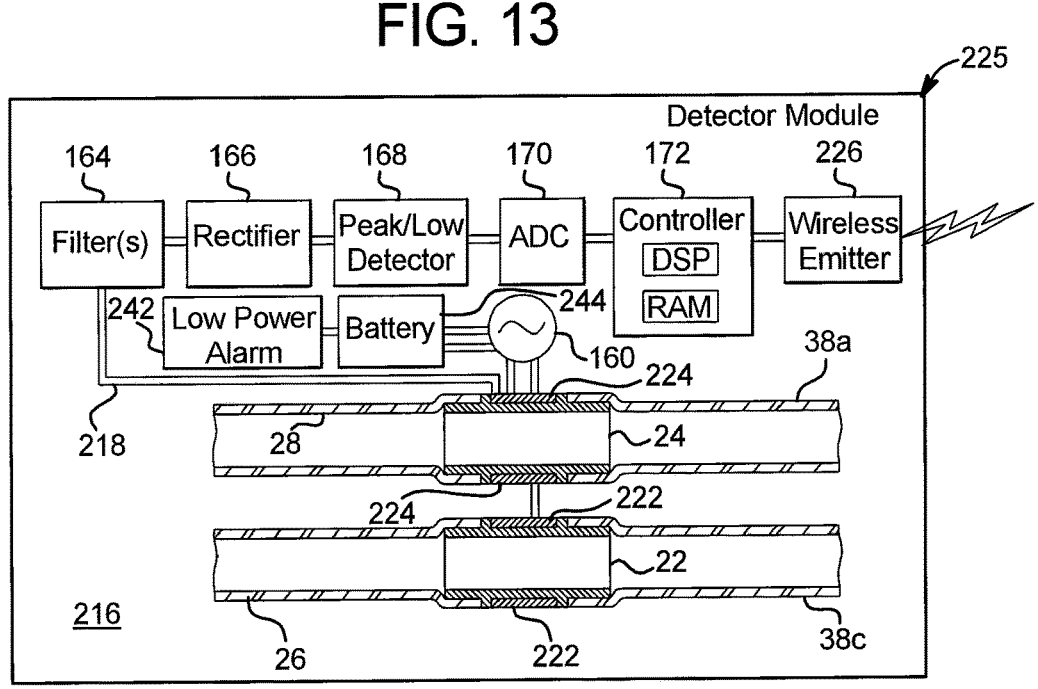
FIG. 13 schematically illustrates a detector module of the access disconnection system of FIG. 12.

Referring additionally to FIG. 13, detector module 225 in one embodiment monitors the electrical impedance of blood in the extracorporeal circuit, as described herein, and generates an alarm causing protector module 230 to clamp at least one of arterial tube segment 38*a* and venous tube segment 38*c* of blood circuit 35 should a venous or arterial dislodgement at patient access 36 occur.

Besides detector module 225 and protector module 230, system 220 also includes a disposable portion in one embodiment as shown in FIG. 13. The disposable portion operates with detector module 225 and includes two contacts 22 and 24 shown in FIG. 1A, which make electrical contact with flowing blood, or clamp over the blood-set tubing. In a retrofit embodiment, prior to treatment, disposable electrodes 22 and 24 are inserted into blood circuit 35. As shown, arterial tube 28 and tubing 38*a* are fitted sealingly over contact 24, while venous tube 26 and tubing 38*c* are fit sealingly over contact 22. Or, blood circuit 35 can be provided with contacts 22 and 24 preinstalled. In any case, contacts 22 and 24 can be metallic components or be made of a conductive polymer. When contacts 22 and 24 are provided with blood circuit 35, detector module 225 is provided with two electrodes 222 and 224, which make electrical contact with contacts 22 and 24 of blood circuit 35, respectively. Electrodes 222 and 224 in the illustrated embodiment are provided as spring clips that hold contacts 22 and 24 and associated tubes 26, 28, 38*a* and 38*b* of blood circuit 35 in place physically.

In an alternative embodiment, blood circuit 35 is not provided with contacts 22 and 24 (not illustrated) and instead detector module 225 is provided with a pair of one of the coupling devices 80, 114 and 130 described above in connection with FIGS. 2A to 2E. Coupling devices 80, 114 and 130 establish electrical connection with the blood, precluding the need for contacts 22 and 24 provided with blood circuit 35.

Detector module 225 senses a needle dislodgement by measuring the impedance between the electrodes as is described herein. To do so, detector module 225 injects an electrical current into the flowing blood. Current injection is performed either invasively (direct blood contact, e.g., from source 160, through electrode 222 or 224 to contacts 22 and 24) or non-invasively (with no contact as discussed below). In one embodiment, detector module 225 induces and measures impedance directly and invasively. Invasive measurement requires that disposable contacts 22 and 24 be placed in physical contact with the flowing blood in blood circuit 35.

Alternative to invasive measurement, detector module 225 can be configured to measure impedance non-invasively, for example by capacitive coupling, or via magnetic induction of current. To achieve capacitive current coupling, detector module 225 places capacitive electrodes (not illustrated) over blood circuit 35. Detector module 225 then applies an alternating voltage to the outer electrodes to induce an ionic current that travels from one electrode to the other. In an inductive embodiment, detector module 225 includes a magnetic coil (not illustrated), which is wrapped around the blood tubing. Detector module 225 induces an ionic current using the magnetic coil. The alternating current applied to the coil changes the magnetic flux in the coil and induces an ionic current in the blood.

Whether the current is introduced to the blood directly, capacitively, or inductively, detector module 225 includes electronics configured to measure a change in electrical impedance. Detector module 225 in an embodiment is a small, light-weight, battery-operated device that connects to disposable ADS electrodes 22 and 24 (FIG. 1A). Detector module 225 includes an excitation voltage source 160 (FIG. 3), which is converted to an electrical current that is induced into the blood. The returning current (which is indicative of an impedance of blood circuit 35) through one of the contacts 22 and 24 is converted to a voltage, measured and processed. Alternatively, detector module 225 measures a voltage across contacts 22 and 24, which is also indicative of an impedance of blood circuit 35.

As illustrated, detector module 225 includes any one or more of voltage source 160 (connected electrically to contacts 22 and 24 through electrodes 222 and 224 of module 25), filter(s) 164, rectifier 166, peak detector 168, analog to digital converter ("ADC") 170, control unit 172 (FIG. 3) and a wireless emitter 226, which is set to communicate with protector module 230. The electronics of detector module 225 in one embodiment are provided on a printed circuit board ("PCB") 216 and connected electrically to each other via traces 218.

Control unit 172 can include a memory, such as a random access memory ("RAM"), and a processor, such as a digital signal processor ("DSP"). RAM stores software and buffers the digital signals from ADC 170. Processor processes the buffered signals using the software. Upon an access disconnection, impedance of blood circuit 35 changes dramatically. Processor of control unit 170 senses this change and sends an output though emitter 226 to receiver 228 of protector module 230. Emitter 226 and receiver 228 in one embodiment operate via radio frequency ("RF"), but alternatively operate via microwave or other suitable frequency. Further alternatively, detector module 225 is hardwired to protector module 230.

Figure 14:
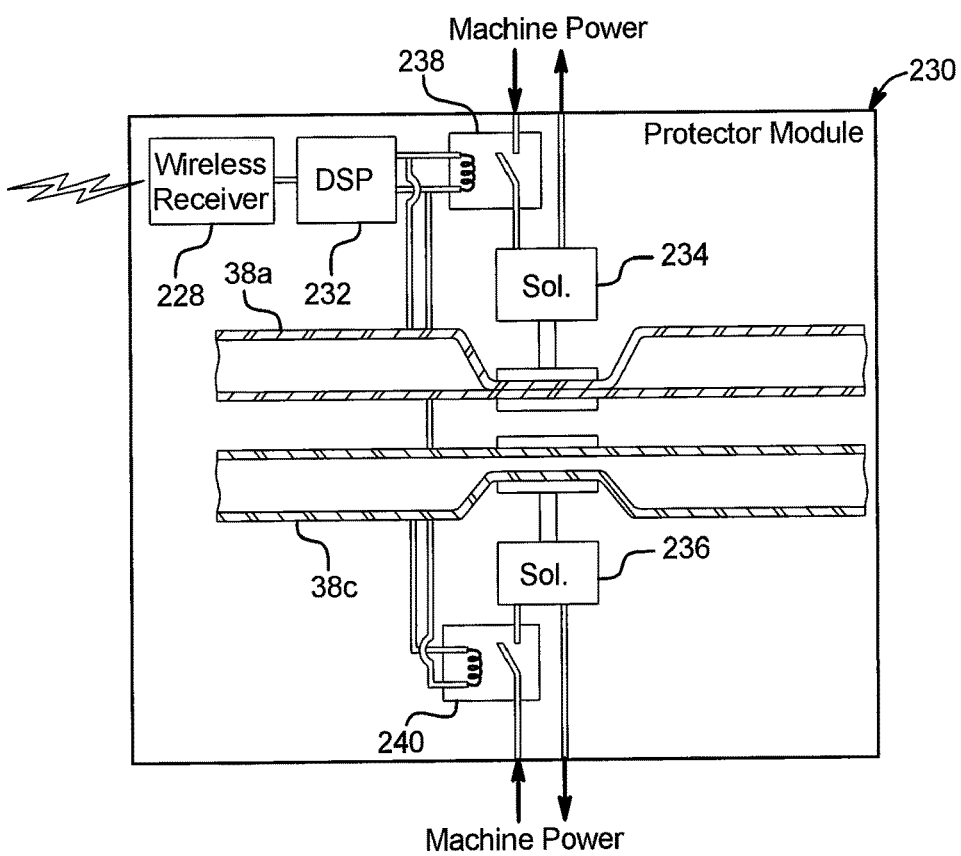
FIG. 14 schematically illustrates a protector module of the access disconnection system of FIG. 12.

Protector module 230 is shown in more detail in FIG. 14. Protector module 230 includes wireless receiver 228, which is set to look only for the particular transmission from its corresponding emitter 226 and detector module 225. In this manner, multiple machines 190 employing system 220 can be set side-by-side. In an embodiment, the signal received by receiver 228 is digitized or is otherwise conditioned by receiver 228 to be in a form suitable for a processor 232, such as a digital signal processor ("DSP") to accept. In an embodiment processor 232 is set to look for a signal from receiver 228 upon which processor 232 causes clamps or occluders 234 and 236 to close one or both of arterial tubing 38a and venous tubing 38c, fully or partially as described in more detail below. Clamps or occluders 234 and 236 in one embodiment are solenoid valves powered off of machine 190. Processor 232 operates with, e.g., solid state switches 238 and 240, which close when directed to allow operating power to reach solenoids 234 and 236, respectively.

Upon receiving an access disconnection signal, protector module 230 is configured to clamp at least venous tubing 38c and in one embodiment both venous tubing 38c and arterial tubing 38a. Clamping both venous tubing 38c and arterial tubing 38a, however, could cause a pressure spike to occur more quickly in venous tubing 38c, which in turn is sensed more quickly by pressure transducer 214 coupled to venous drip chamber 40. A pressure spike sensed by pressure transducer 214 causes circuitry, e.g., within machine 190, to shut down blood pump 46, in one embodiment, before the pressure can increase enough to damage venous tubing 38c. This circuitry can already be present within machine 190, so that it would not have to be added to system 220. Alternatively, protector module 230 can include the necessary circuitry.

In an alternative embodiment, if pressure transducer 214 is not provided or if the transducer is simply for reading out pressure rather than for control, both venous tubing 38c and arterial tubing 38a bloodlines are occluded. Arterial bloodline 38a is occluded completely to prevent any further blood from being lost (other than what is already in the extracorporeal circuit). Venous bloodline 38c is occluded partially to slow down loss of blood already in the extracorporeal circuit, while preventing damage to bloodline 38c due to an excess pressure.

Detector module 225 and protector module 230 are relatively simple, inexpensive devices. It is contemplated to mount protector module 230 to the front 194 of machine 190, however, protector module 230 can be mounted alternatively to any part of machine 190 to which venous tubing 38c and arterial tubing 38a can reach and still reach patient access 36. Protector module 230 in one embodiment is powered from machine 190. Detector module 225 as mentioned above can be battery powered. To that end, battery 244 of detector module 225 in one embodiment is rechargeable and protector module 230 in one embodiment includes an electrical socket to receive a power recharging connector of detector module 225 for recharging the battery 244 of and storing detector module 225 between uses.

Detector module 225 in one embodiment includes a low power alarm 242, which alerts a patient or caregiver when detector module 225 needs to have its battery 244 recharged or replaced. Battery 244 powers voltage source 160 and any one or more of filter(s) 164, rectifier 166, peak detector 168, ADC 170, control unit 172, alarm 242 and wireless emitter 226 needing power. Although not illustrated, alarm 242 can interface though emitter 226 to cause protector module 230 to clamp the blood lines 38a and 38c and potentially stop blood pump 46 until battery 244 of detector module 225 is recharged. To that end, detector module 225 is configured to accept AC power (not illustrated) in one embodiment, so that therapy can be resumed without having to recharge or replace a battery immediately.

Either one of detector module 225 and protector module 230 can include a small monitor and/or data port (not illustrated) to download stored information in real time or later for diagnostic purposes. In one embodiment such apparatus is provided on detector module 225, so that retrieved data does not have to be sent to protector module 230. Alternatively, e.g., for power or space reasons, monitor and/or data port are provided with protector module 230. In such case, necessary software and processing capability are added to protector module 230.

The data retrieved can include any one of peak impedance (e.g., low blood flowrate), low impedance (e.g., high blood flowrate), average impedance (e.g., average blood flowrate), frequency of impedance spikes, etc. For example, it is contemplated that the blood pump's cyclical occlusion of blood circuit 35 will create impedance spikes having a signature frequency. If the frequency changes it could be a sign of blood pump wear or improper functioning or signal that the patient is causing impedance spikes, e.g., by kinking a line. This data retrieval and analysis can be performed by any of the systems described herein.

The electronics of detector module 225 and protector module 230 in one embodiment are stand-alone and do not need to interface with those of machine 190, except perhaps for powering protector module 230 as discussed above. It is expressly contemplated however to incorporate detector module 225 and protector module 230 in a newly sold machine 190, for example as an option, which may or may not be sold with the new machine 190.

Maximizing Upper Branch Impedance and Minimizing Patient Grounding

It has been found that the above-described access disconnection ("ADS") systems using electrical impedance measurement to detect the dislodgement of an arterial or venous needle during hemodialysis to prevent undetected blood loss is effected by patient "grounding". Patient grounding is caused by the connection of the patient either directly, or through other devices, to earth ground. Patient grounding reduces the detection sensitivity of the ADS systems, at least in part, because the dialyzer, which is normally connected to earth ground for patient safety, provides an alternate impedance path in parallel with the measured impedance between the electrodes as shown below.

Figure 15:
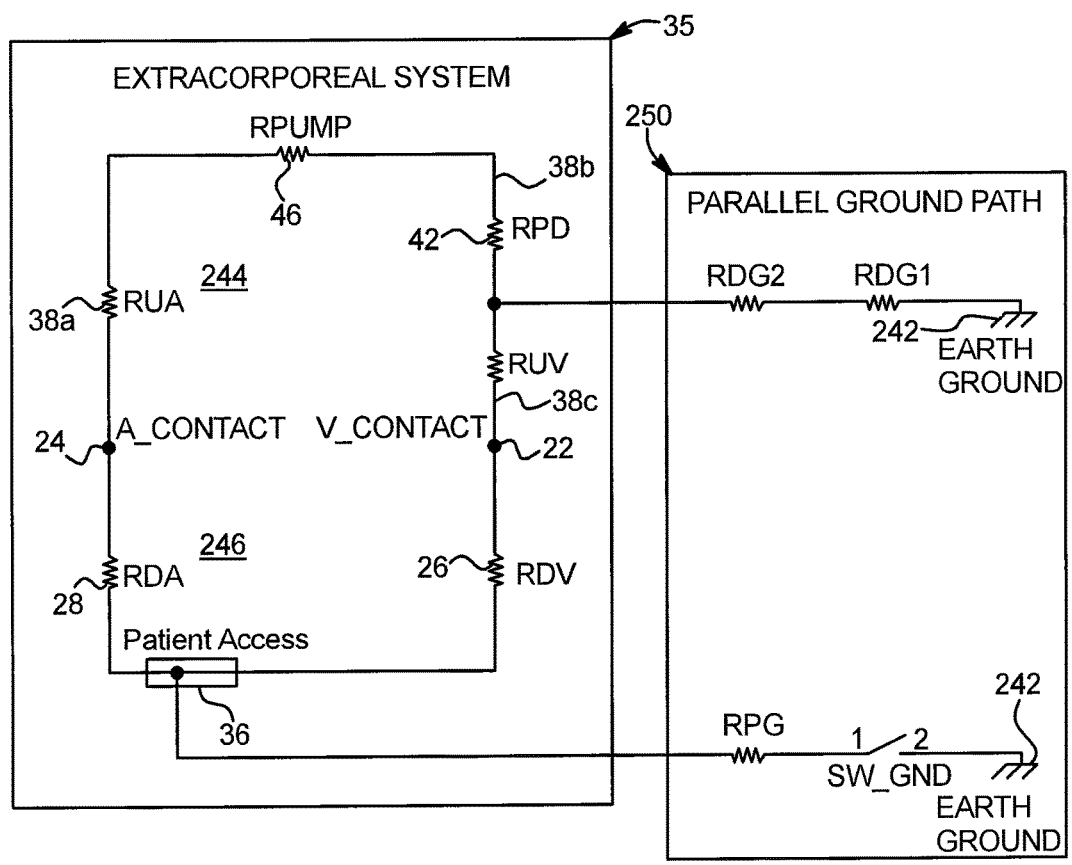
FIG. 15 is a schematic electrical diagram modeling a blood circuit and a parallel earth ground path.

In the following figures, the method and apparatus of the present disclosure for minimizing the effect of patient grounding on the ADS system is illustrated as an electrical lumped model for blood in blood circuit 35 in combination with a model 250 for the parallel path of earth ground 242 as shown in FIG. 15. Sections of tubing containing either blood, dialysate or both are modeled as impedances that, at low frequencies, are considered to be close to resistances. The impedances for blood circuit 35 are as follows:

RUA is the impedance of the blood in tubing section 38a from arterial contact 24 to the outlet of blood pump 46;

RPUMP is the impedance of the peristaltic pump (which varies during each revolution);

RPD is the impedance of blood in tubing section 38b connecting blood pump 46 to dialyzer 42;

RUV is the impedance of blood in the tubing 38c from dialyzer 42 to venous contact 22;

RDV is the impedance of the blood in the venous tubing 26 from venous contact 22 to patient access 36; and RDA is the impedance of the blood in the arterial tubing 28 from patient access 36 to arterial contact 24.

As discussed above, arterial contact 24 and venous contact 22 are two disposable items that connect the ADS system electrically to the arterial and venous branches of the extracorporeal blood circuit, respectively. The electrical circuit at arterial contact 24 node and venous contact 22 node divides two branches in parallel, an upper branch 244 and a disconnection branch 246, each branch 244 and 246 including different sets of lumped impedances.

Disconnection branch 246 includes impedances RDA and RDV in series, while upper branch 244 includes the combination of RUA, RPUMP, RPD and RUV (assuming the impedance of patient access 36 and dialyzer 42 is negligible compared to the rest of the impedances). Disconnection branch 246 includes impedances RDA and RDV and has a lower overall impedance than does upper branch 244, having RUA, RPUMP, RPD and RUV due to (i) the fundamentally different lengths of tubing in different sections of the extracorporeal system and (ii) tubing occlusion of peristaltic pump 46.

Figure 16:
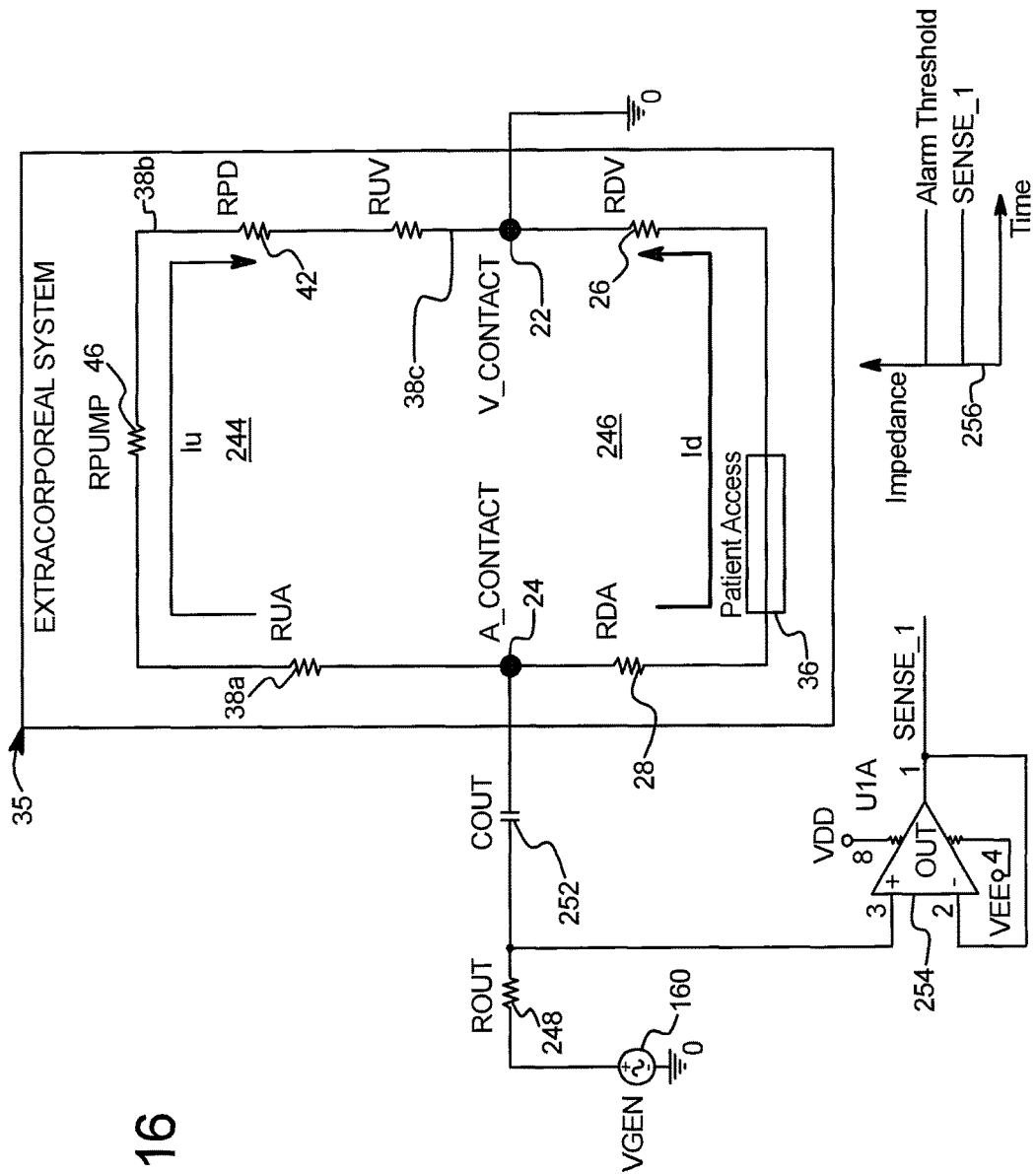
FIG. 16 is a schematic electrical diagram modeling a blood circuit and sensing circuitry without a parallel earth ground path showing both needles lodged.

FIG. 16 shows one electrical diagram for the systems described herein, which measure the impedance of blood in blood circuit 35 using a voltage source 160 and a high resistance resister 248 (e.g., one mOhms or more) to convert the voltage to a known current, injecting the known current between the arterial contact 24 and the venous contact 22 and monitoring the resulting voltage on the arterial contact 24. In the illustrated embodiment, a capacitor 252 is positioned to remove any direct current ("DC") component from the current signal. As illustrated, controller 172 (illustrated above) measures impedance by measuring a corresponding voltage measured at SENSE 1 of operational amplifier 254. The signal at SENSE 1 is conditioned, e.g., via an amplifier and an analog to digital converter.

Needle dislodgement increases impedance and reduces the current signal for the constant voltage applied by source 160 according to the principles of Ohm's Law. If the current signal changes enough, so that the corresponding impedance increases above a certain threshold, a corresponding controller 172 triggers an alarm. FIG. 16 illustrates normal operation in which both arterial and venous needles are lodged in patient access 36. Current induced by source 160 is split between upper current $I_u$ flowing through upper branch 244 and lower path current $I_d$ flowing though disconnection branch 246. Plot 256 in FIG. 16 shows that the outputted voltage signal SENSE 1 indicative of an impedance of blood circuit 35 is below an alarm threshold voltage.

Figure 17:
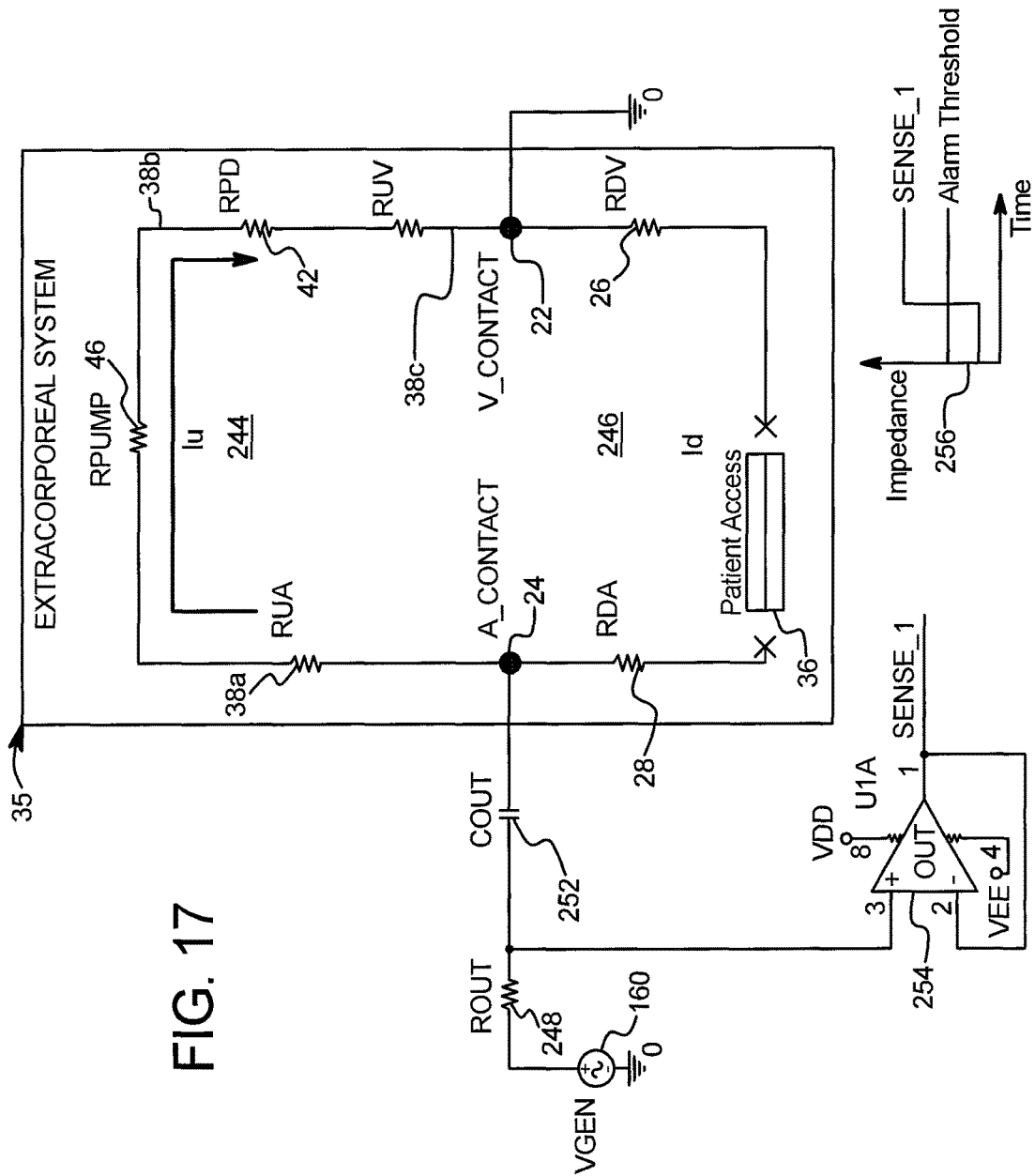
FIG. 17 is a schematic electrical diagram modeling a blood circuit and sensing circuitry without a parallel earth ground path showing at least one needle dislodged.

FIG. 17 illustrates the same ADS system as shown in FIG. 16 during a dislodgement of the arterial or venous needle of patient access 36. Here, impedance of disconnection branch 246 increase, causing current $I_d$ flowing though disconnection branch 246 to go to zero. This causes the amplitude of SENSE 1 as depicted on plot 256 to increase over the threshold impedance level. The change in SENSE 1 is a function of the impedance of the upper branch 244 and disconnection branch 246 of blood circuit 35. Impedance of the upper branch 244 is not constant. The rotation of blood pump rotor 46 on the tubing creates a modulation in impedance because it exerts different degrees of occlusion as it rotates. It should be appreciated that maximizing the impedance of the upper branch 244 under normal operation, thereby decreasing upper branch 244 current $I_u$ and maximizing disconnection branch 246 current $I_d$ would magnify the effect of increased amplitude at SENSE 1.

Figure 18:
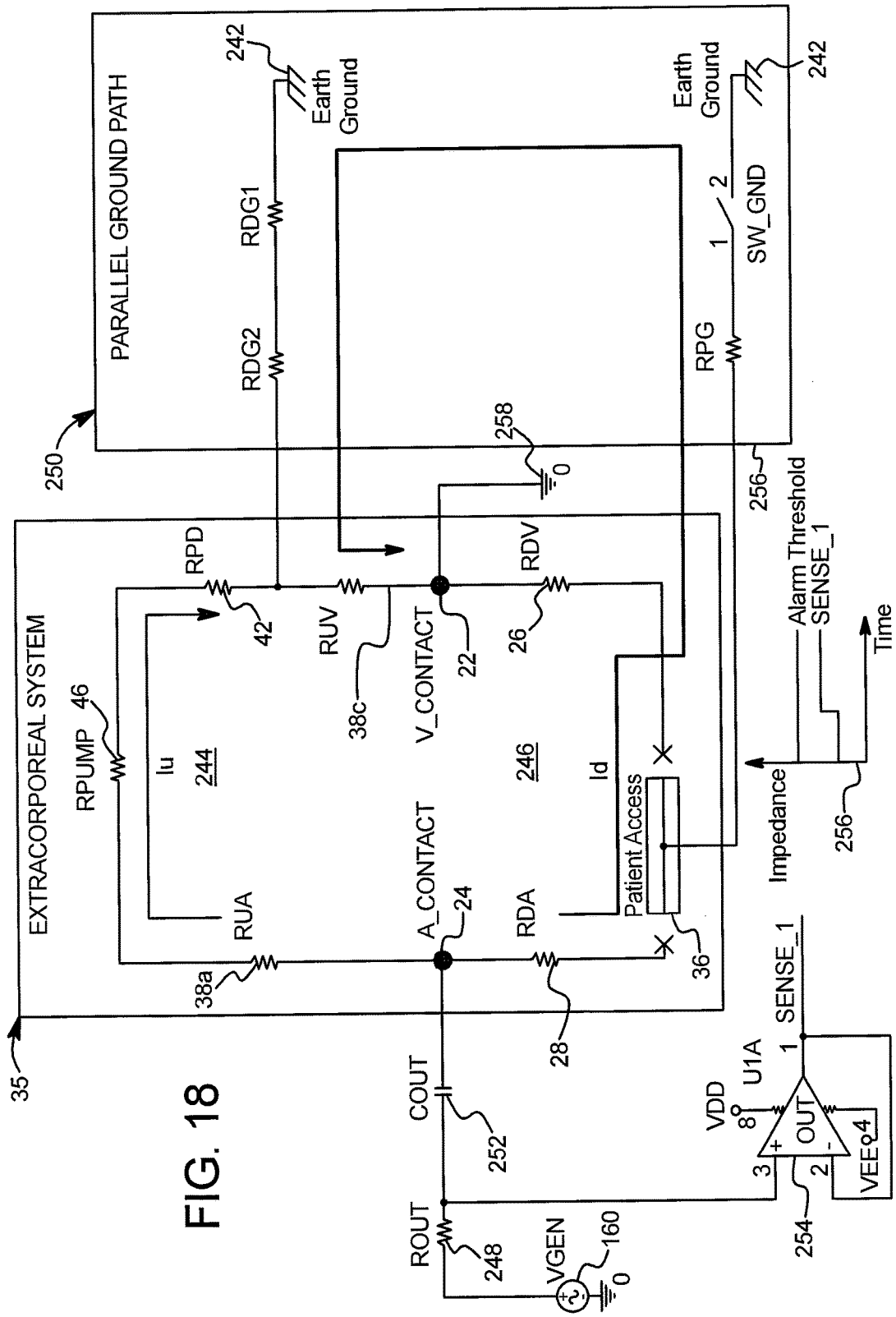
FIG. 18 is a schematic electrical diagram modeling a blood circuit and sensing circuitry with a parallel earth ground path showing at least one needle dislodged and a parallel current path to isolated ground through earth ground.

The electrical system of FIGS. 16 and 17 does not completely describe the electrical situation when dialyzer 42 is connected to earth ground 242 (as is generally required) as shown and described in FIG. 15. FIG. 18 illustrates the disconnection state of FIG. 10 when dialyzer 42 is connected to earth ground 242 of parallel ground path 250. Here, the system as shown includes a potential connection of the patient to earth ground 242. When the patient is connected to earth ground 242, another return path exists for the injected current $I_d$, as seen in bold in FIG. 18. In FIG. 18:

RPG represents the patient's body impedance to ground; and

RDG1 and RDG2 represent dialysate impedances.

The problem of patient grounding exists despite electrical isolation (e.g., through an isolation transformer) of the excitation voltage from earth ground 242. The effect of patient grounding is to significantly reduce the measured change in impedance due to dislodgement as depicted in plot 256 of FIG. 18. Here, an alternative current path is made allowing disconnection current $I_d$ upon an access disconnection to flow from earth ground 242 to a system ground 258, which is connected to venous contact 22. Instead of stopping upon an access disconnection, disconnection branch 246 current $I_d$ continues to flow. As a result, the impedance of the parallel ground return path 250 reduces the change in impedance measured at SENSE 1 to such a degree that it does not rise above the threshold. Here, an alarm will not be sounded nor a blood pump stopped, etc.

Figure 19:
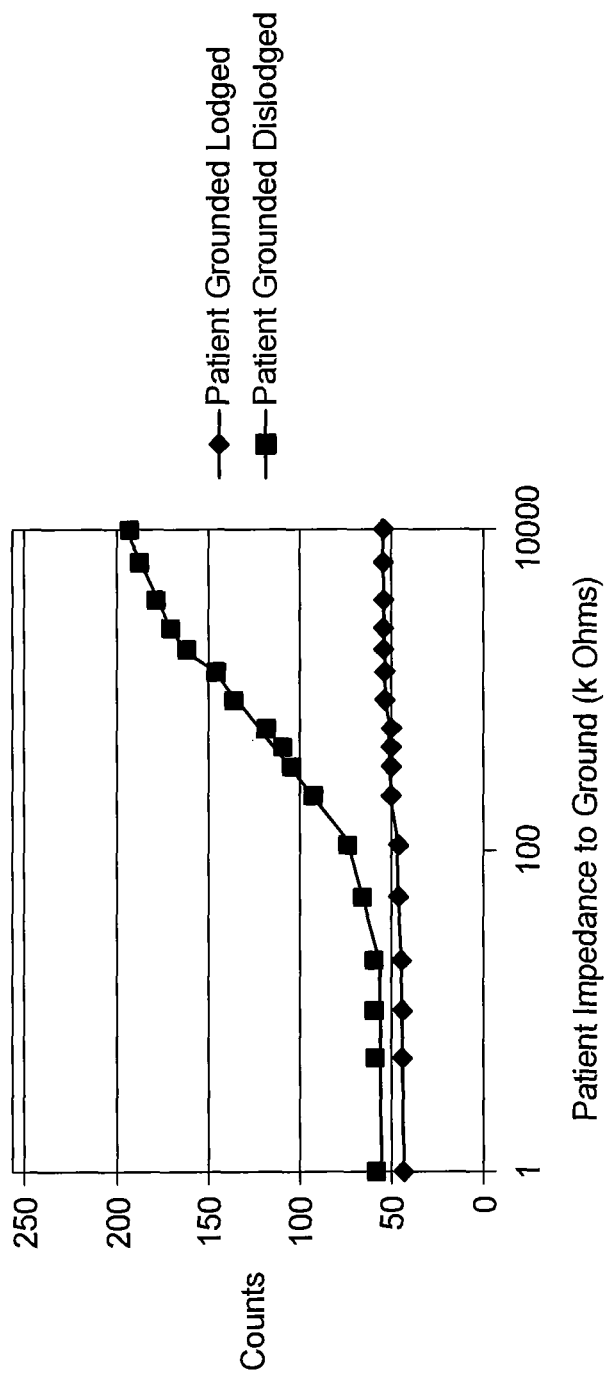
FIG. 19 is a plot of digitized sensed patient grounded lodged versus patient grounded dislodged impedance signals versus kOhms for the system of FIG. 18.

FIG. 19 shows a simulation of the change in measured voltage due to dislodgement as a function of the patient impedance to ground from a resistive model based on blood measurements for the system of FIG. 18. The y-axis is a linear scale proportional to measured voltage (at SENSE 1, in which output voltage is fed through an analog to digital converter, which scales the voltage into counts per time, e.g., zero counts corresponding to no voltage and 256 counts corresponding to a maximum voltage). The x-axis is a logarithmic scale showing changes in patient impedance to earth ground (RPG). The data show voltages for the conditions of needle lodged (diamonds) and dislodged (squares). As can be seen by comparing the two plots, if the impedance change threshold (in plot 256) is set at forty counts, the system will not detect a dislodgement when patient impedance to ground is less than about 100 kOhm. Since in practice the patient can be connected to ground through a varying impedance, this can cause large variations in measured impedance compared to the detection threshold. The effect of patient grounding should therefore be minimized for effective detection of needle dislodgement using impedance.

Maximizing Upper Branch Impedance

Figure 20:
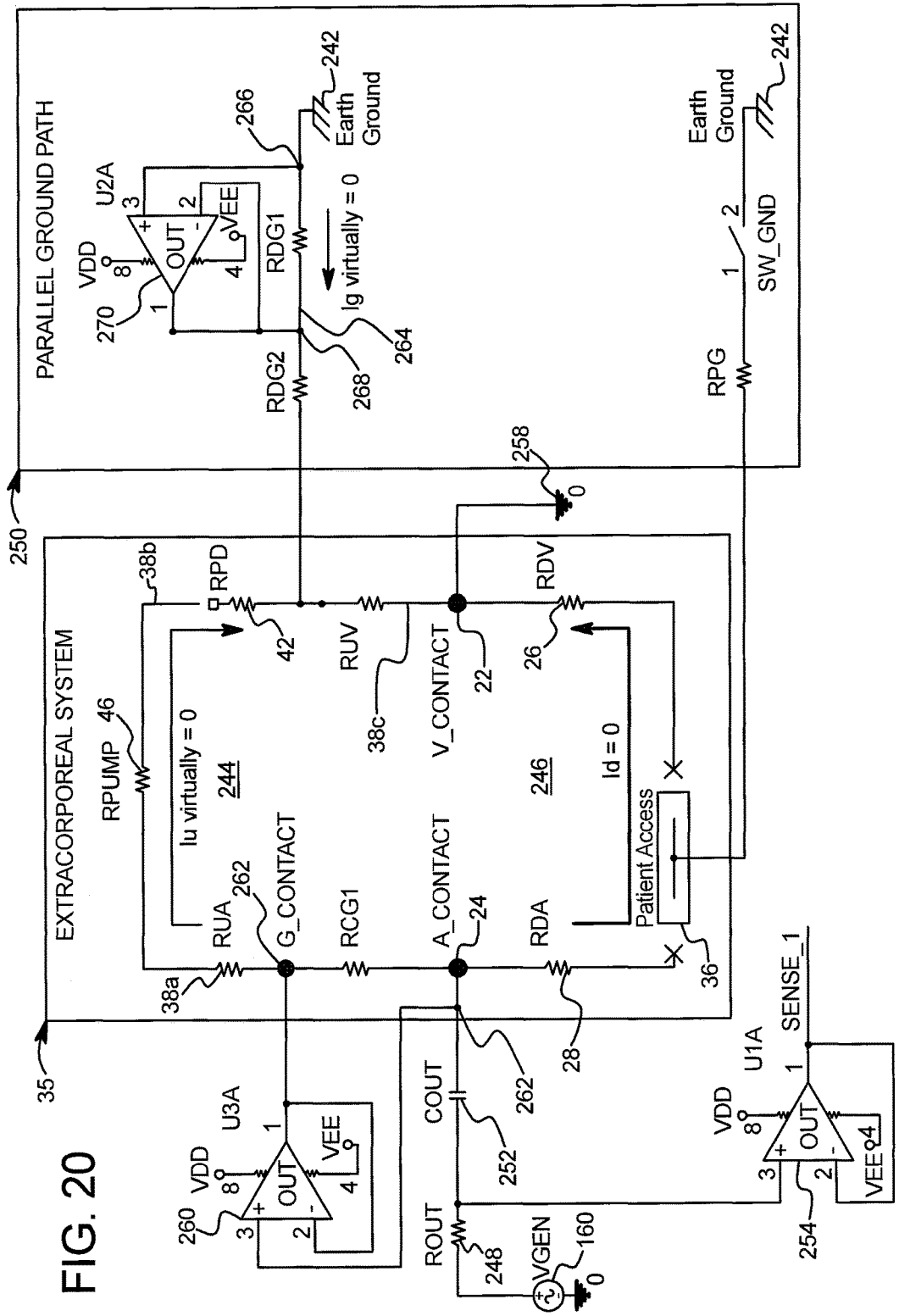
FIG. 20 is a schematic electrical diagram showing one system for combating the effects of patient grounding and for increasing the impedance through the blood tubing operating with the peristaltic pump.

FIG. 20 illustrates an apparatus and method for maximizing the impedance of the upper branch 244 under normal operation, thereby decreasing upper branch 244 current $I_u$ and maximizing disconnection branch 246 current $I_d$ under normal operation. In FIG. 20, a signal producing source 260, such as an operational amplifier, is placed across a portion of upper branch 244. Here, voltage source 160 in combination with resistor 248 induces a current from node 262 into operational amplifier 260, which amplifies the current by one and outputs a voltage which is at the same potential as node 262 at G CONTACT 262. In this manner a same potential exists at node 262 and G CONTACT 262, at opposite ends of a tubing segment having an impedance RCG1, which simulates an open circuit, driving upper branch 244 current $I_u$ effectively to zero as seen in FIG. 20 and forcing the current though lower path 246, which enhances the signal at SENSE 1.

Ground Current Reduction Circuitry

FIG. 20 also illustrates an apparatus and method for minimizing the effect of patient grounding using the same approach described above for maximizing the impedance of the upper branch 244. Again, the method is based on the principle of counteracting current flow by creating a virtual open circuit, which is achieved using electronic feedback to dynamically create two contact points 266 and 268 of equal potential across a section of tubing, here a dialysate path 264 leading to or from dialyzer 42. It should be appreciated that in contrast to blood side contacts 22 and 24, contacts 266 and 268 are reusable and do not add to disposable cost.

A signal producing source 270, such as an operational amplifier, is placed across a portion of dialysate path 264. The voltage potential at contact 266 is fed to operational amplifier 270, which amplifies the signal by one and outputs a voltage which is at the same potential as contact 266 at second contact 268. The electronics operating with parallel ground path 250 monitor the electrical potential on earth ground 242 with respect to isolated system ground 258, and generate the same potential at contact 268 between RDG1 and RDG2. In this manner a same potential exists at opposite ends of a tubing segment of dialysate path 264 having an impedance RDG1, which simulates an open circuit, driving ground current Ig effectively to zero as seen in FIG. 20.

Figure 21:
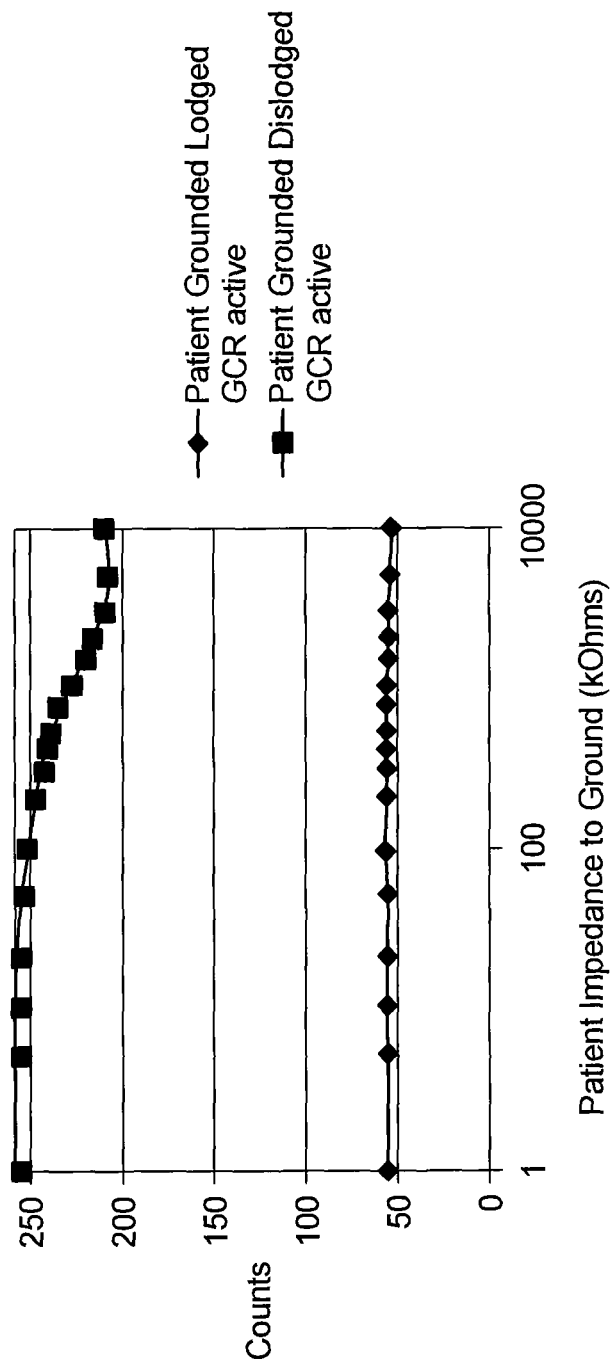
FIG. 21 is a plot of digitized sensed patient grounded lodged versus patient grounded dislodged impedance signals versus kOhms for the system of FIG. 20.

Experimental results obtained on a laboratory implementation of the ADS system of FIG. 20 are plotted on FIG. 21. FIG. 21 shows the same type of simulation as FIG. 19. Here, a measured voltage due to dislodgement as a function of the patient impedance to ground for the system of FIG. 20 is illustrated. The y-axis is a linear scale proportional to measured voltage (at SENSE 1, in which output voltage is fed through analog to digital converter, which scales the voltage into counts per time as discussed above). The x-axis is again a logarithmic scale showing changes in patient impedance to earth ground (RPG). The data show voltages for the conditions of needle lodged (diamonds) and dislodged (squares).

As can be seen by comparing the two plots, the effect of the ground current reduction circuitry is very noticeable when this graph is compared to the one in FIG. 19. Indeed it is believed that even without circuitry 260 used to drive upper path 244 current $I_u$ to zero, circuitry 270 used to drive ground current Ig to zero alone is adequate to provide an accurate and repeatable ADS system.

Movement of Measurement Electrodes to Combat Patient Grounding

A mathematical analysis of the ADS system of FIG. 18 shows that the ratio between the measured impedance when the patient is dislodged to that measured when the patient is lodged, is especially sensitive to the ratio between RUV, the impedance between dialyzer 42 and venous contact 22, and RDV, the impedance between venous access contact 22 and patient access 36. As the ratio of RUV to RDV increases, so increases the difference between dislodged and lodged measurements of impedance. Accordingly, the ADS system of FIG. 18 can be made more immune to the effect of patient grounding by increasing impedance RUV with respect to impedance RDV.

Mathematical analysis also shows that lower values of impedance RDA, the impedance between patient access 36 and arterial contact 24, also increase the difference between dislodged and lodged measurements. Reducing impedance RDA and impedance RDV while simultaneously increasing impedance RUV is desirable. Placing venous contact 22 and arterial contact 24 as close to the patient as possible reduces impedances RDA and RDV while increasing impedance RUV.

Figure 22:
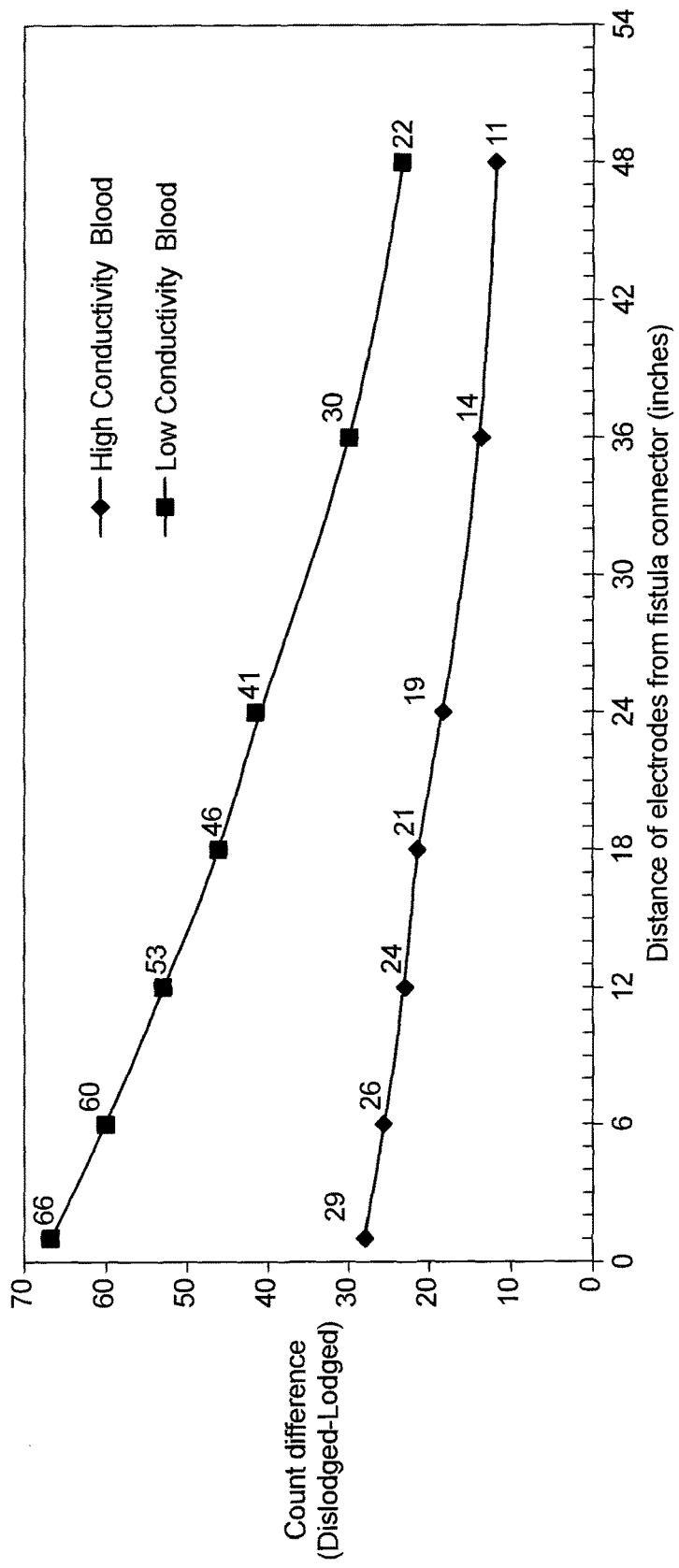
FIG. 22 is a plot for another system for combating the effects of patient grounding showing digitized sensed impedance signals for high and low conductivity blood for different blood contact spacings from patient access.

The effect of moving venous contact 22 and arterial contact 24 closer to the patient is shown in FIG. 22. The y-axis is the digitized measured voltage (dependent on the impedance and the same as in FIGS. 19 and 21) and the abscissa is the distance of venous contact 22 and arterial contact 24 from the patient's fistula set connector at patient access 36. For both low conductivity blood (diamonds) and high conductivity blood (squares), impedance for a given input signal and blood circuit 35 is higher at SENSE 1 when venous contact 22 and arterial contact 24 are moved closer to the patient.

Moving venous contact 22 and arterial contact 24 closer to the patient may be used alone or in combination with one or more of the other methods for reducing the effects or patient grounding and increasing the impedance measured at SENSE 1.

Dual Sense Circuitry to Combat Patient Grounding

Figure 23:
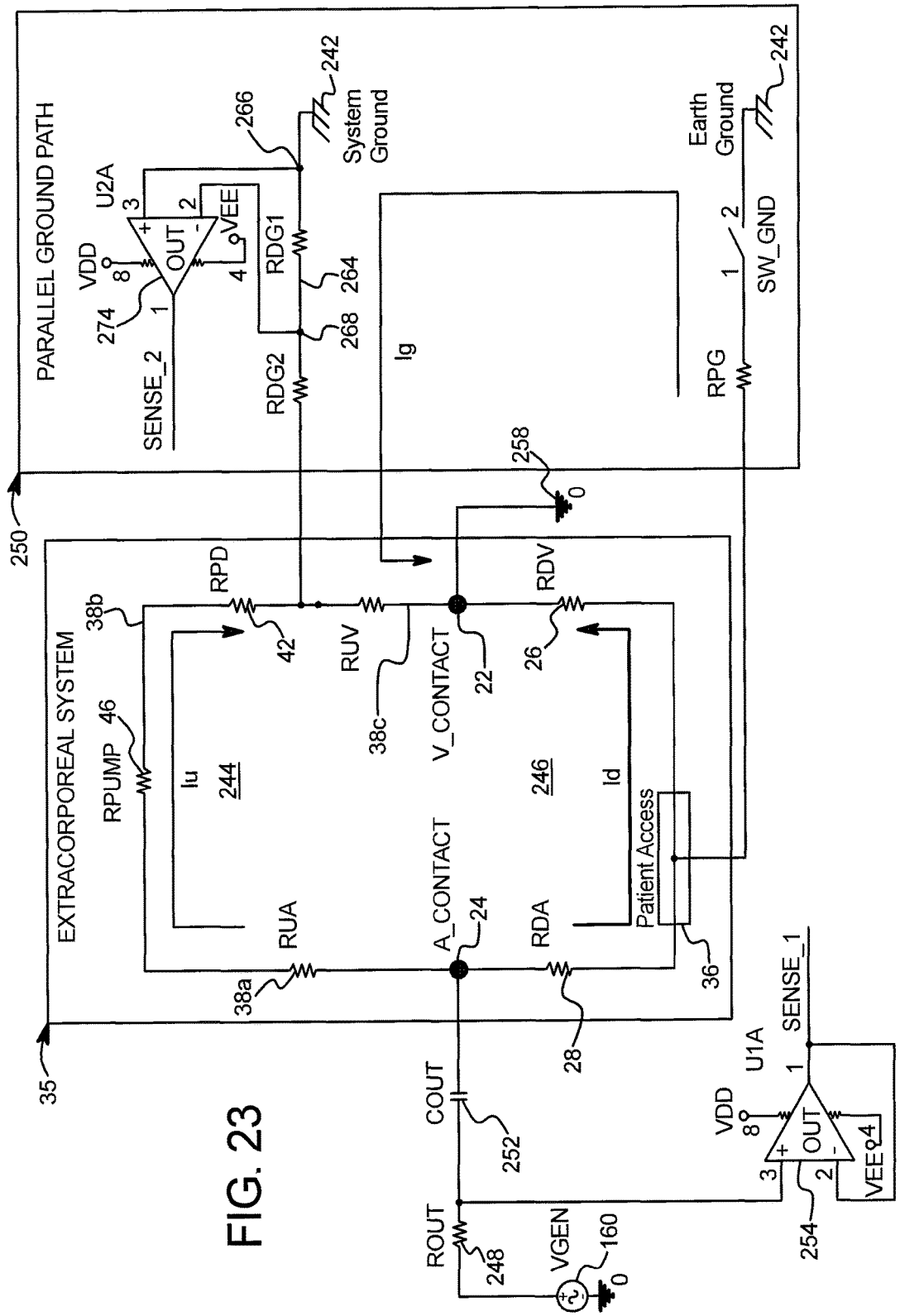
FIG. 23 is a schematic electrical diagram showing a further system for combating the effects of patient grounding using dual sensing circuitry, a first circuitry sensing impedance in the blood path, the second circuitry sensing impedance in the ground path.

Referring now to FIG. 23, another apparatus and method for combating the effects of patient grounding relies on the fact that connection between the patient and earth ground 242 forces a portion of the excitation current $I_g$ to flow in the ground return path and reduce the signal $I_d$ on SENSE 1 to levels below the detection threshold. In the system of FIG. 23, a second sensing circuitry 274 is placed in dialysate path 264 at contacts 266 and 268. As with sensing circuitry 254, controller 172 (illustrated above) measures a ground impedance by measuring a corresponding voltage measured at SENSE 2 of operational amplifier 274. The signal at SENSE 2 is conditioned, e.g., via an amplifier and an analog to digital converter.

Monitoring the excitation current Ig in the parallel ground path 264 not only indicates whether the patient is grounded or not, it is also used to enhance the detection of a dislodgement from patient access 36 when the patient is grounded. In such a case, the current Ig flowing in the ground return path 264 would increase dramatically upon a dislodgement.

The ADS system of FIG. 23 accordingly uses both signals SENSE 1 and SENSE 2. The combination of SENSE 1 and SENSE 2 covers the entire range of impedances between the patient and earth ground 242. That is, if the patient is isolated from earth ground 242, SENSE 1 is adequate to detect dislodgement. When the patient's impedance to earth ground 242 is very low, e.g., the patient is at earth ground, controller 172 is caused to use SENSE 2 as the monitoring source. At intermediate stages of patient connection to earth ground, a combination of both signals is used for reliable dislodgement detection.

In one embodiment, controller 172 is configured to choose between one of the three signal scenarios: (i) SENSE 1 only, (ii) SENSE 2 only, and (iii) SENSE 1 plus SENSE 2 to determine (i) when SENSE 1 is high enough to trigger an alarm, (ii) when SENSE 2 is high enough to trigger an alarm, and (iii) pick when SENSE 1 or SENSE 2 must both be used to trigger an alarm.

Alternatively, controller 172 is configured to always use the third scenario SENSE 1 plus SENSE 2. Here, controller 172 can also look to SENSE 2 to indicate whether the patient is grounded or not.

Figure 24:
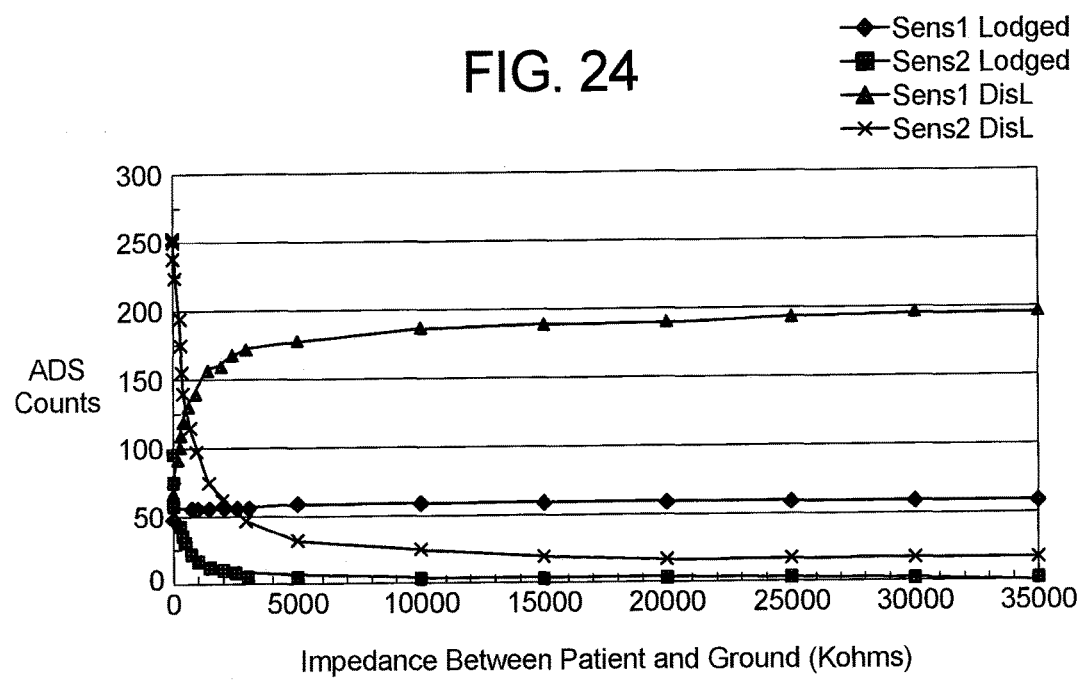
Figure 25:
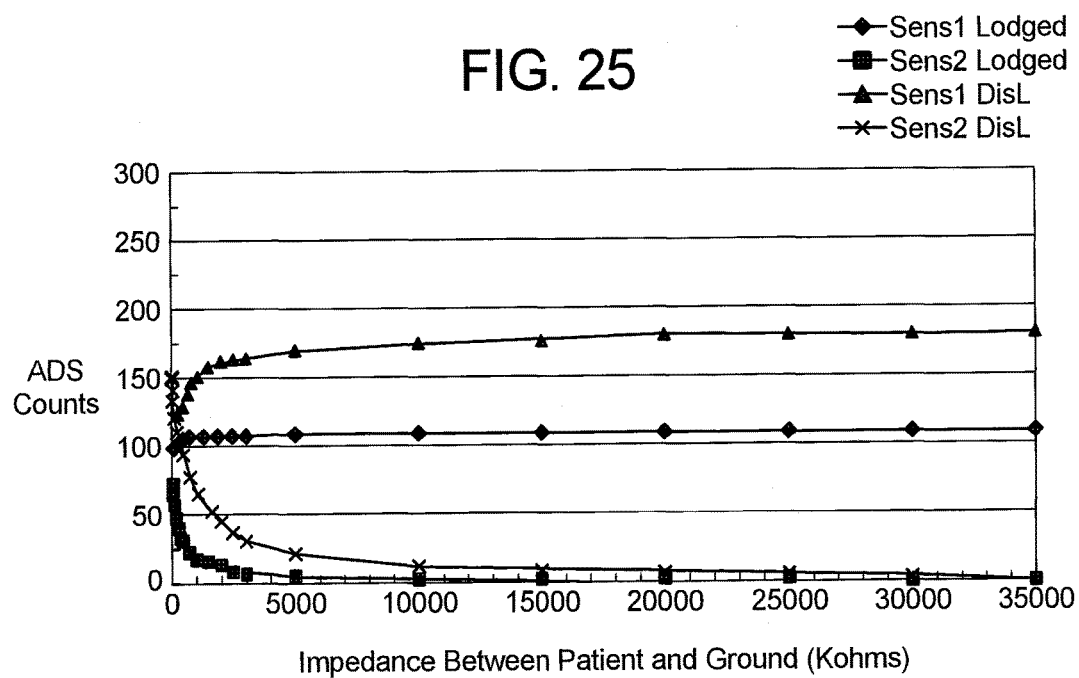

Experimental Results obtained on a laboratory implementation of the resistive high-conductivity blood model of the system of FIG. 23 are plotted in FIG. 24. The equivalent graph for low-conductivity blood is plotted in FIG. 25. Laboratory measurements performed on bovine blood are plotted on FIG. 26, for high conductivity blood, and on FIG. 27, for low conductivity blood. In each case, using SENSE 2 appears to be an effective way to detect an access disconnection up to at least about 3000 to 5000 kOhms of impedance above ground.

Using the Dialysate Path to Eliminate Disposable Contacts in ADS Devices

Referring to 28, a dialysate sensing system is illustrated in which dialyzer 42 provides an electrical path from the blood in the extracorporeal circuit, through the dialysate fluid in path 264, to earth ground 242. Noticeably, blood circuit 35 does not include contacts 22 and 24. The contacts are provided instead in the dialysate path 264 as shown in more detail below. This is advantageous because the contacts are not part of the disposable of the system, saving cost.

A signal injected in the dialysate fluid will circulate through the blood in the extracorporeal circuit and the patient's body as long as a return path, from the patient to either earth ground or the signal's isolated ground 258, is provided. In one embodiment, a return path to earth ground 242 or isolated ground 258 is facilitated by a grounding strap 280 fixed to the cuff of the blood pressure monitor that is attached to the patient's arm (FIG. 33) during blood treatment, e.g., hemodialysis treatment.

Figure 28:
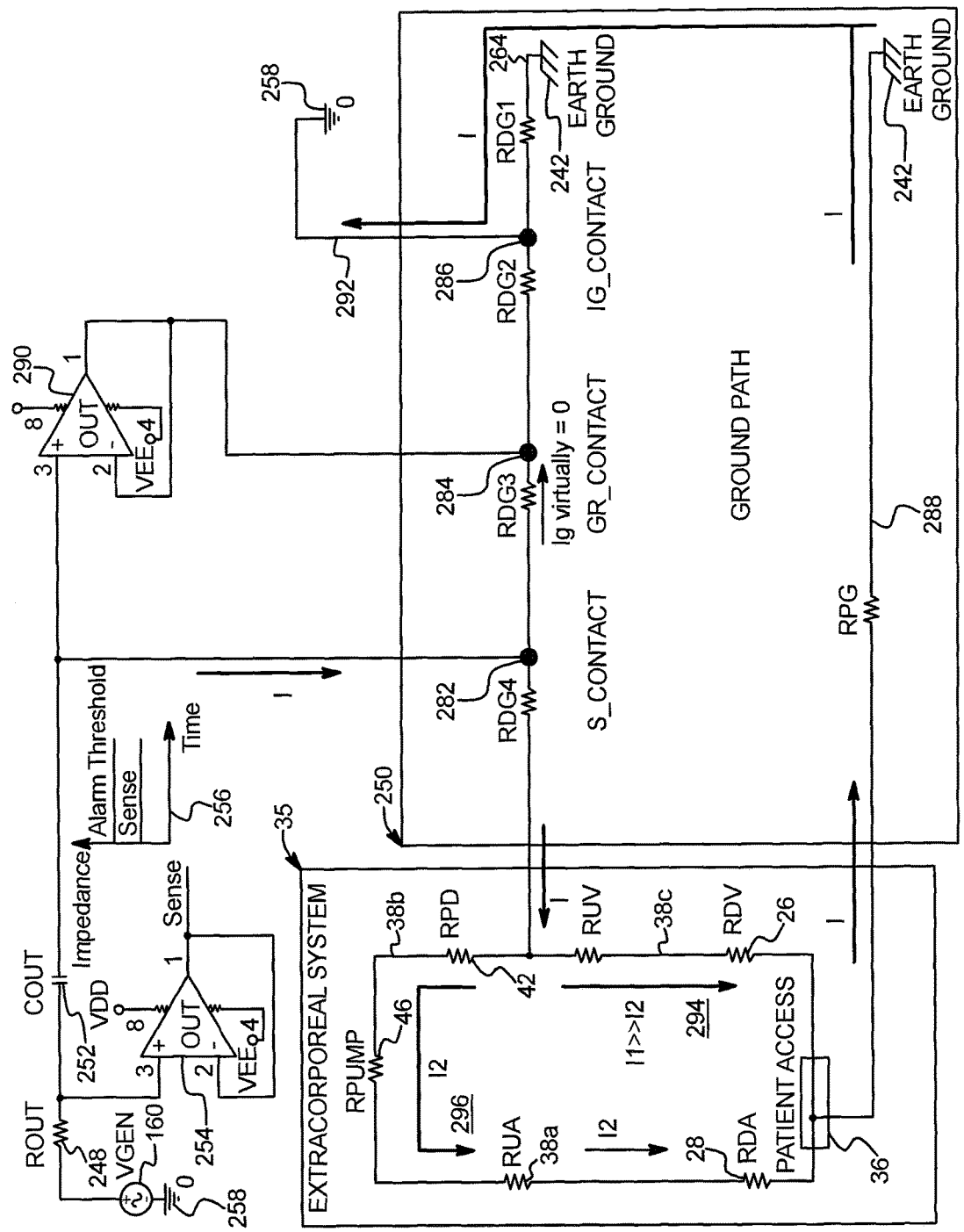
FIG. 28 is a schematic electrical diagram showing a further system for combating the effects of patient grounding and using the dialyste path for sensing impedance with both needles lodged.

In the dialysate sensing system of FIG. 28, the method proposed is illustrated by an electrical lumped model for blood in the blood circuit 35 in conjunction with a model for the parallel earth ground path 250. In FIG. 28, S CONTACT 282, GR CONTACT 284 and IG CONTACT 286 are three non-disposable contacts that connect the dialysate sensing system to dialysate path 264 inside the, e.g., hemodialysis instrument. These contacts divide:

RDG1 (between IG CONTACT 286 and earth ground 242), the first section of the impedance between earth ground 242 and dialyzer 42;

RDG2 (between GR CONTACT 284 and IG CONTACT 286), the second section of the impedance between earth ground 242 and dialyzer 42;

RDG3 (between S CONTACT 282 and GR CONTACT 284), the third section of the impedance between earth ground 242 and dialyzer 42; and RDG4 (between dialyzer 42 and S CONTACT 282), the forth section of the impedance between earth ground 242 and dialyzer 42.

In FIG. 28, a signal producing source 290, such as an operational amplifier, is placed across portion RDG3 of dialysate path 264. Here, voltage source 160 in combination with resistor 248 induces a current into operational amplifier 290, which amplifies the current by one and outputs a potential at GR CONTACT 284, which is at the same potential as a potential that it outputs at S CONTACT 282. In this manner a same potential exists at S CONTACT 282 and GR CONTACT 284, at opposite ends of a tubing segment having an impedance RDG3, which simulates an open circuit, driving ground current current $I_g$ effectively to zero as seen in FIG. 28. The guard signal injected at GR CONTACT 284 prevents current from circulating through RDG3.

Voltage source 160 and resister 248 also injects a current at S CONTACT 282, which the open circuit forces through RDG4 and then to split into first branch 294 current $I_1$, and second branch 296 current $I_2$, which are electrically in parallel. First branch 294 includes impedance RUV in series with impedance RDV, while second branch 296 includes series impedances RPD, RPUMP, RUA and RDA. First branch 294 (RUV and RDV) has a much lower impedance than does second branch 296 (RPD, RPUMP, RUA and RDA) due to the fundamentally different lengths of tubing in different sections of the extracorporeal system and tubing occlusion by peristaltic pump 46. Accordingly, current $I_1$ though branch 294 is much greater than current $I_2$ though branch 296. The currents circulate through patient access 36 into earth ground 242 and, finally, through RDG1 to $I_G$ CONTACT 286 connected to isolated ground 258 through the patient's connection 288 to earth ground 242 and isolation return path 292. In an alternative embodiment, the patient ground path 288 is connected directly to isolation ground 258.

The dialysate sensing system of FIG. 28 measures impedance at SENSE using operational amplifier 254 as described above. The signal at SENSE is conditioned, e.g., via an amplifier and an analog to digital converter. The dialysate sensing system measures the impedance between S CONTACT 282 and IG CONTACT 286 by monitoring the resulting voltage on the S CONTACT 282. Venous needle dislodgement increases the measured impedance measured at SENSE. The dialysate sensing system triggers an alarm if the impedance change exceeds a threshold level.

In FIG. 28, the dialysate sensing system is depicted in normal operation with both needles lodged at patient access 36. As seen in plot 256, the measured impedance at SENSE is normally below the threshold amount.

Figure 29:
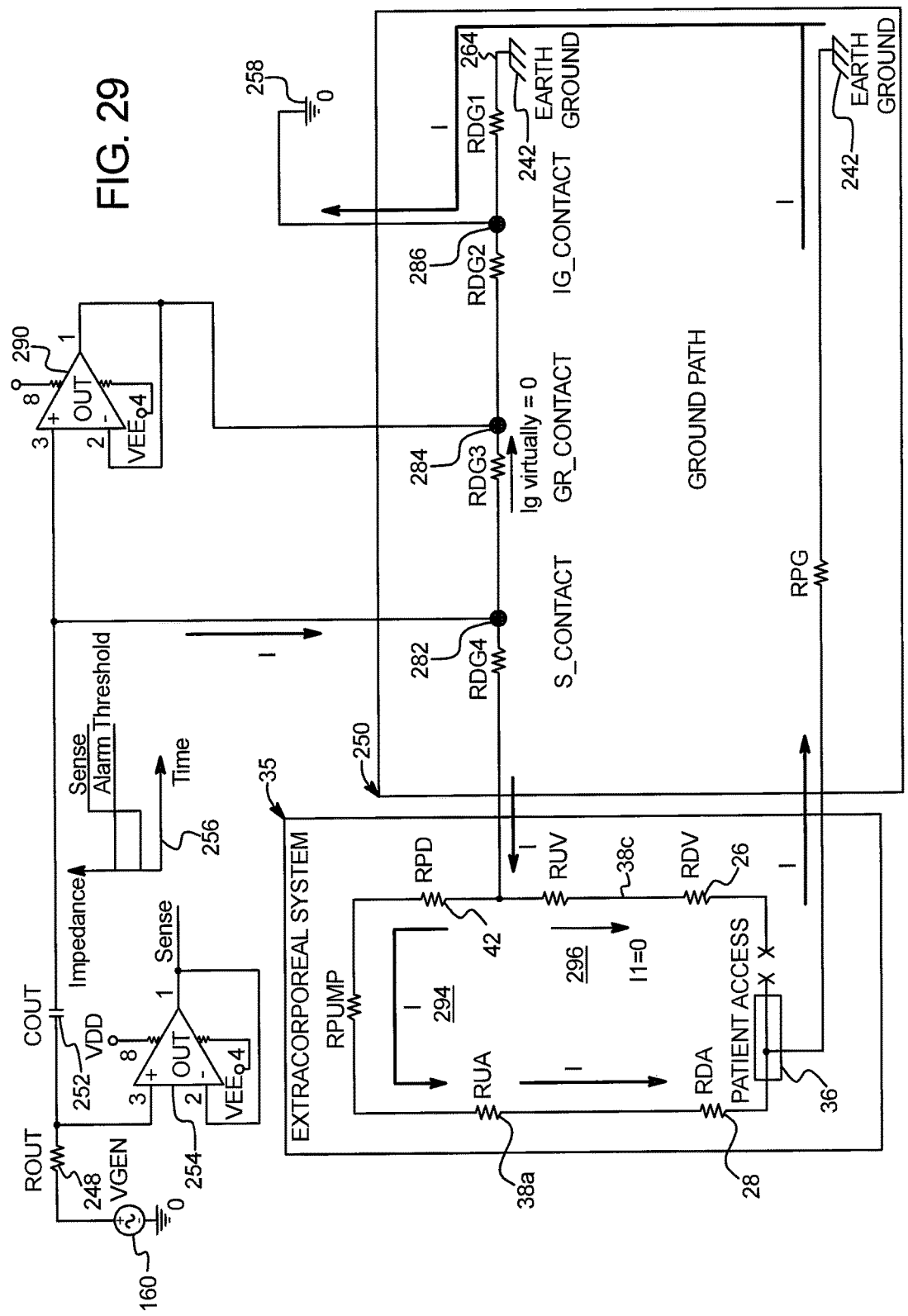
FIG. 29 is a schematic electrical diagram for the system of FIG. 28 with the venous needle dislodged.

In FIG. 29, the dialysate sensing system is shown during a needle dislodgment, e.g., a venous needle dislodgement at patient access 36. Here, current $I_1$, through path 294 goes to zero and all current $I_2$ is forced through high impedance path 296. The effect of increased amplitude of SENSE is depicted at plot 256. The change in impedance is due to the fact that only high impedance (RPD, RPUMP, RUA and RDA) branch 294 of blood circuit 35 is connected. Detecting a venous needle (return path) dislodgement is more important because damage from an arterial path dislodgement (pre-pump) is inherently mitigated.

Figure 30:
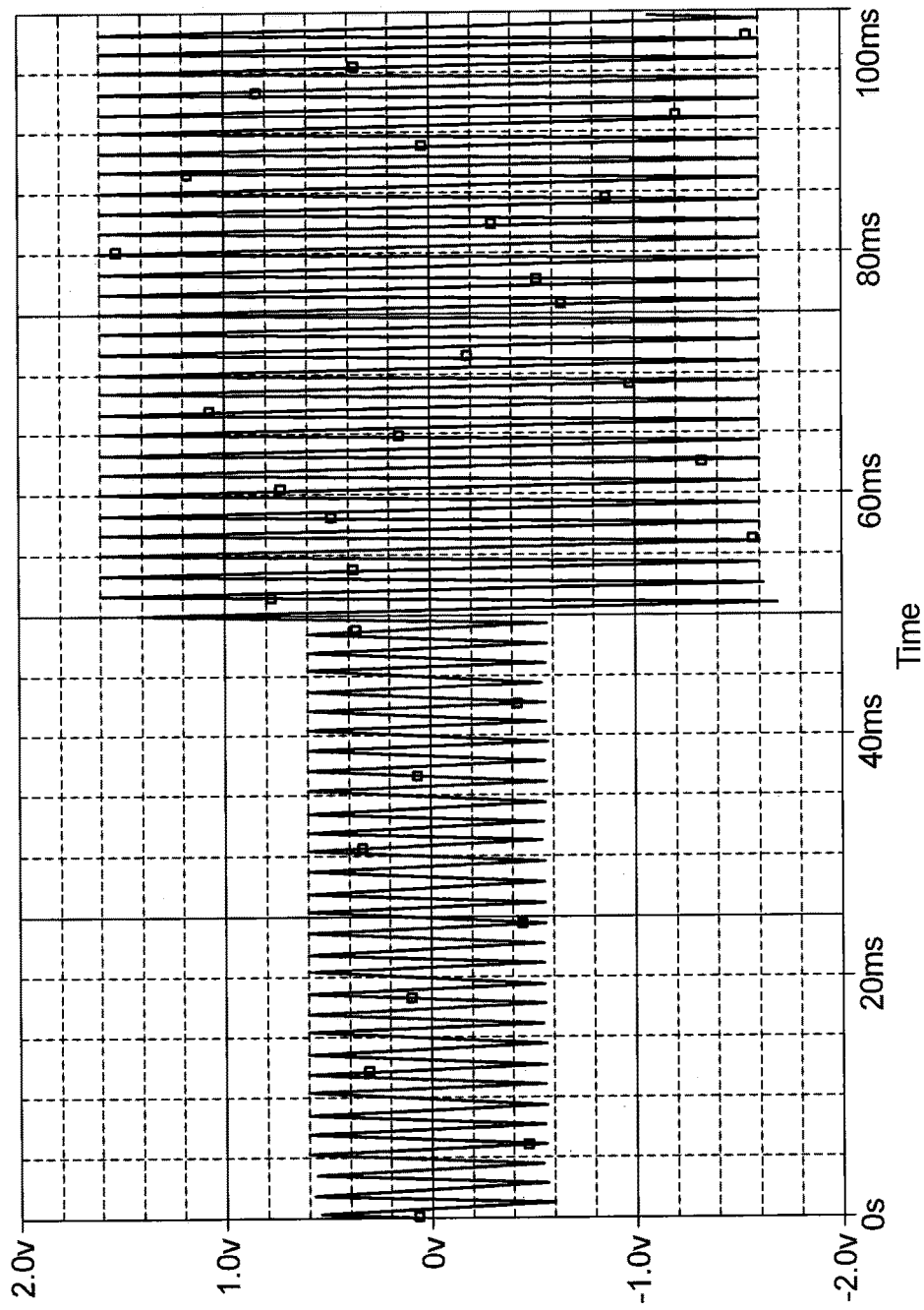
FIGS. 30 to 32 are various plots of output voltage or digitized impedance signal versus time for the dialysate sensing system of FIGS. 28 and 29.

FIG. 30 shows a simulation of the SENSE voltage signal on a model of a patient, here, with low hematocrit. The y-axis shows voltage. The x-axis shows time. The section between zero and fifty milliseconds is the SENSE signal with both needles lodged at patient access 36, while the section between fifty and one-hundred milliseconds is the signal during venous dislodgement. The voltage output at SENSE more than doubles upon a needle dislodgment. These results are similar for a patient with high hematocrit.

Figure 31:
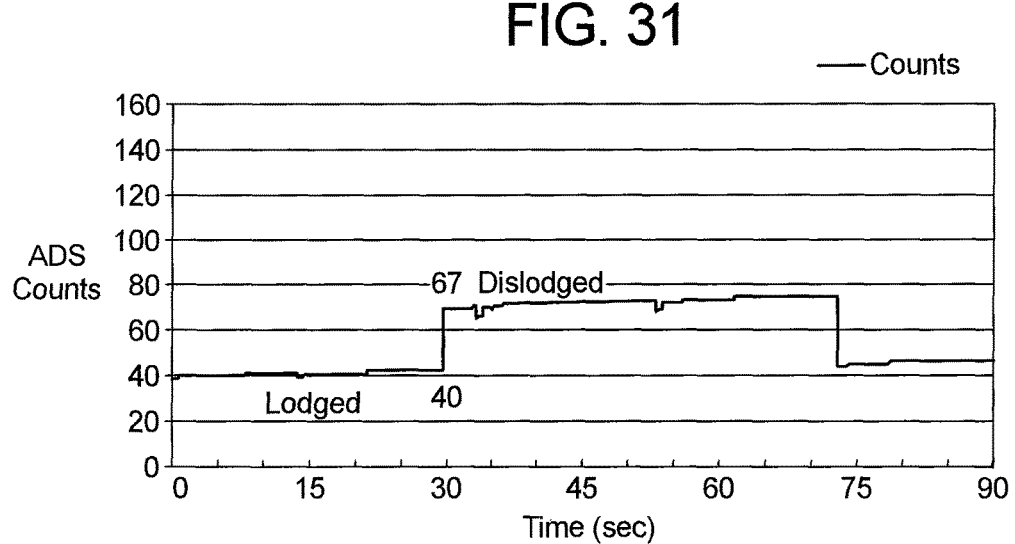
Figure 32:
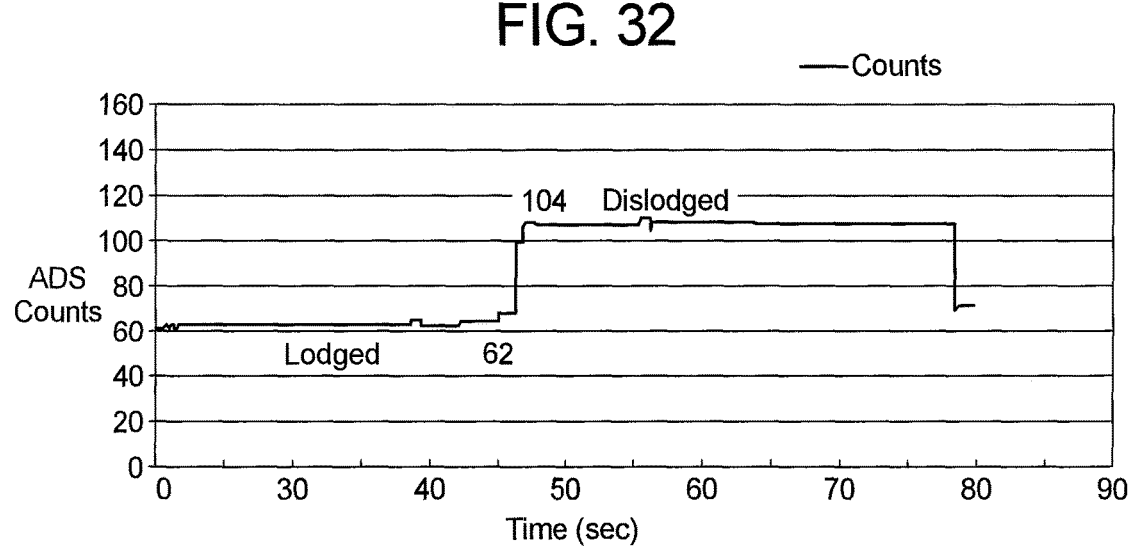

FIGS. 31 and 32 show the SENSE signal digitized into counts (less counts corresponding to lower impedance, more counts corresponding to higher impedance) over time for low and high hematocrit bovine blood, respectively. FIGS. 31 and 32 each include a lodged, dislodged and back to lodged sequence. Impedance at SENSE increases measurably in both cases. When patient access 36 is re-lodged, impedance at SENSE returns to the initial level, showing that the system is repeatable.

Figure 33:
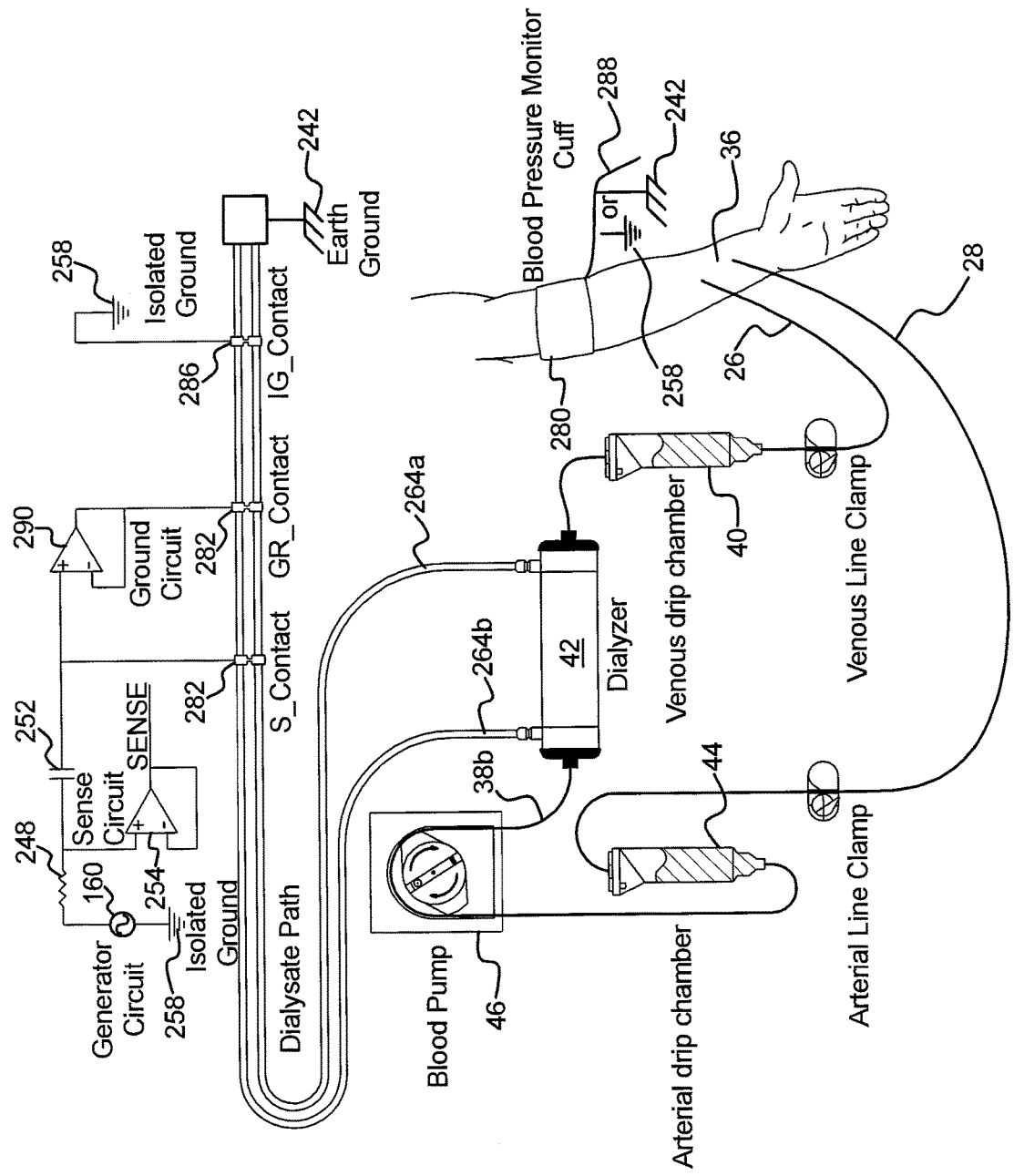
FIG. 33 shows the hardware associated with the dialysate sensing system of FIGS. 28 and 29.

FIG. 33 shows hardware associated with the dialysate sensing system. Dialysate path 264 is split into to-dialyzer path 264a and from-dialyzer path 264b to produce counter-current flow. S CONTACT 282, GR CONTACT 284 and IG CONTACT 286 are in electrical communication with the dialysate in both to-dialyzer path 264a and from-dialyzer path 264b. Circuitry 160, 248, 252, 254 and 280 are shown as described above. Blood pump 46 pumps blood from patient access 36, through arterial line 28, arterial drip chamber 44, dialyzer 42, venous drip chamber 40, venous line 26, back to patient access 36.

In FIG. 33, the dialysate sensing system is shown in two configurations. Both configurations connect return path 288 to the patient via a grounding strap 280 fixed to the blood pressure cuff attached for example to the patient's arm. In one implementation, return path 288 is made to isolated ground 242. In a second implementation, return path 288 is made to earth ground 242. It is believed that both grounding implementations provide an effective and repeatable impedance measuring access disconnection system. Again, the dialysate sensing system of FIGS. 21 to 26 is advantageous because it does not include disposable metal contacts.

It should be understood that various changes and modifications to the presently preferred embodiments described herein will be apparent to those skilled in the art. Such changes and modifications can be made without departing from the spirit and scope of the present disclosure and without diminishing its intended advantages. It is therefore intended that such changes and modifications be covered by the appended claims.

The invention is claimed as follows:

1. An access disconnection system comprising: an extracorporeal circuit; a dialysate circuit; a first sensing apparatus configured to sense a first signal indicative of a first electrical impedance produced by fluid flowing through the extracorporeal circuit; and a second sensing apparatus configured to sense, in a parallel ground path, a second signal indicative of a second electrical impedance produced by a respective fluid flowing through the dialysate circuit and a portion of the extracorporeal circuit.

2. The access disconnection system of claim 1, which includes first and second contacts provided in the extracorporeal circuit and a signal source communicating with at least one of the first and second contacts and configured to generate a signal within fluid flowing through the extracorporeal circuit.

3. The access disconnection system of claim 2, wherein the signal generated by the signal source is split into the first and second signals.

4. The access disconnection system of claim 3, wherein the second signal has at least one characteristic selected from the group consisting of: (i) being in parallel with the first signal; and (ii) being indicative of a patient's electrical potential relative to ground.

5. The access disconnection system of claim 1, which includes a controller in communication with the first and second sensing apparatuses, the controller configured to monitor the first signal only for an access disconnection if the second signal is below a threshold.

6. The access disconnection system of claim 1, which includes a controller in communication with the first and second sensing apparatuses, the controller configured to monitor the second signal only for an access disconnection if the second signal is above a threshold.

7. The access disconnection system of claim 1, which includes a controller in communication with the first and second sensing apparatuses, the controller configured to monitor the first and second signals for an access disconnection.

8. The access disconnection system of claim 1, wherein at least one of the first and second electrical impedances is a lumped electrical impedance.

9. The access disconnection system of claim 1, wherein the fluid flowing through the extracorporeal circuit is at least substantially blood and the fluid flowing through the dialysis circuit is at least substantially dialysate.

10. An access disconnection system comprising:
an extracorporeal circuit;
a dialysate circuit;
an electrical path extending from the dialysate circuit to the extracorporeal circuit;
a signal source configured to induce a signal into the electrical path from the signal source;

a sensing apparatus configured to sense the signal, the signal indicative of an electrical impedance of the electrical path, including sensing the electrical impedance (i) in a parallel ground path or (ii) in the extracorporeal circuit and in the parallel ground path; and an apparatus positioned at multiple points along the electrical path, and configured to create a virtual open circuit that prevents the signal induced into the electrical path by the signal source from flowing between the multiple points.

11. The access disconnection system of claim 10, which includes a grounding device configured to bring a patient to ground, such that when the patient is connected to the extracorporeal circuit and to the grounding device, the electrical path extends from the extracorporeal circuit to ground.

12. The access disconnection system of claim 10, which includes electronics configured to cause an alarm when the sensing apparatus senses an increase of electrical impedance due to a disconnection of a patient from the extracorporeal circuit.

13. The access disconnection system of claim 12, wherein the increase of electrical impedance is due to the signal being shunted through a larger electrical impedance path of the extracorporeal circuit upon the access disconnection.

14. The access disconnection system of claim 10, wherein the virtual open circuit is in the dialysate circuit.

15. The access disconnection system of claim 14, wherein at least one of the signal source and sensing apparatus communicates with the electrical path at the dialysate circuit between the multiple points and the extracorporeal circuit.

16. An access disconnection system comprising: an extracorporeal circuit; a dialysate circuit; a signal source configured to initiate, at the dialysate circuit, a signal into the dialysate circuit; and a single sensing apparatus configured to sense the signal, the signal indicative of at least one electrical impedance in the extracorporeal circuit, at least one electrical impedance in a ground path between the extracorporeal circuit and the dialysate circuit, and at least one electrical impedance in the dialysate circuit.

17. The access disconnection system of claim 16, which includes an apparatus positioned to apply a potential at multiple points along the dialysate circuit, the applied potential creating a virtual open circuit between the multiple points.

18. The access disconnection system of claim 17, which includes an electrical path extending from the signal source located at one side of the multiple points, through the extracorporeal circuit, through a path to earth ground, through the dialysate circuit located at a second side of the multiple points, to isolated ground.

* * * * *